United States Patent
Shibuya et al.

(10) Patent No.: US 8,961,946 B2
(45) Date of Patent: Feb. 24, 2015

(54) HAIR PROCESSING AGENT AND METHOD FOR PERMANENT WAVING HAIR

(75) Inventors: Akira Shibuya, Kawasaki (JP); Hidemasa Aoki, Kawasaki (JP); Makoto Saito, Kawasaki (JP); Motoaki Kamachi, Kawasaki (JP); Atsushi Tsuchiya, Toshima-ku (JP); Akio Okamura, Toshima-ku (JP)

(73) Assignee: Showa Denko K.K., Tokyo (JP)

( * ) Notice: Subject to any disclaimer, the term of this patent is extended or adjusted under 35 U.S.C. 154(b) by 1803 days.

(21) Appl. No.: 11/792,828

(22) PCT Filed: Dec. 20, 2005

(86) PCT No.: PCT/JP2005/023834
§ 371 (c)(1),
(2), (4) Date: Jun. 12, 2007

(87) PCT Pub. No.: WO2006/068276
PCT Pub. Date: Jun. 29, 2006

(65) Prior Publication Data
US 2008/0085251 A1    Apr. 10, 2008

Related U.S. Application Data

(60) Provisional application No. 60/639,807, filed on Dec. 29, 2004, provisional application No. 60/668,093, filed on Apr. 5, 2005, provisional application No. 60/668,090, filed on Apr. 5, 2005, provisional application No. 60/668,612, filed on Apr. 6, 2005.

(30) Foreign Application Priority Data

| Dec. 20, 2004 | (JP) | 2004-368373 |
| Mar. 24, 2005 | (JP) | 2005-086089 |
| Mar. 24, 2005 | (JP) | 2005-087141 |
| Mar. 28, 2005 | (JP) | 2005-092178 |

(51) Int. Cl.
*A61K 8/46* (2006.01)
*A61Q 5/04* (2006.01)
*A61K 8/49* (2006.01)

(52) U.S. Cl.
CPC ........... *A61K 8/4933* (2013.01); *A61Q 5/04* (2013.01)
USPC ........................................... 424/70.5

(58) Field of Classification Search
CPC ............ A61Q 5/06; A61Q 5/08; A61Q 5/10; A61Q 5/12; A61Q 5/04; A61K 8/4933; C07D 207/273; C07D 333/34; C07D 307/30; C07D 223/10
See application file for complete search history.

(56) References Cited

U.S. PATENT DOCUMENTS

| 2,577,710 | A | * | 12/1951 | McDonough | 132/206 |
| 3,328,415 | A | * | 6/1967 | Surrey et al. | 548/186 |
| 3,345,381 | A | * | 10/1967 | Campbell | 549/52 |
| 3,758,513 | A | * | 9/1973 | Ahmadi et al. | 549/299 |
| 3,966,903 | A | * | 6/1976 | Torii et al. | 424/70.4 |
| 4,870,010 | A | * | 9/1989 | Hayes | 424/114 |
| 5,190,937 | A | * | 3/1993 | Markwell et al. | 514/183 |
| 5,332,570 | A | * | 7/1994 | Bergstrom et al. | 424/70.51 |
| 5,461,158 | A | | 10/1995 | Mita et al. | |
| 5,824,751 | A | * | 10/1998 | Hori et al. | 525/450 |
| 6,143,286 | A | * | 11/2000 | Bhambhani et al. | 424/70.1 |
| 2003/0180241 | A1 | * | 9/2003 | Sakurai et al. | 424/70.2 |

FOREIGN PATENT DOCUMENTS

| DE | 199 02 246 A1 | 12/1999 |
| EP | 0 639 566 A | 2/1995 |
| JP | 3-271214 A | 12/1991 |
| JP | 5-97800 A | 4/1993 |
| JP | 8-291031 A | 11/1996 |
| JP | 2000-507272 A | 6/2000 |
| JP | 2003-528901 A | 9/2003 |
| WO | WO 98/30197 A1 | 7/1998 |
| WO | WO 01/74318 A2 | 10/2001 |

* cited by examiner

*Primary Examiner* — Suzanne Ziska
*Assistant Examiner* — Thurman Wheeler
(74) *Attorney, Agent, or Firm* — Sughrue Mion, PLLC

(57) ABSTRACT

Provided are hair processing agents capable of permanent waving hair even at a neutral to weakly acidic pH range that causes less irritation to the skin, and hair processing agents in which an unpleasant odor is masked. Hair processing agents contain at least one compound represented by the formula (2). Hair processing agents contain a compound of the formula (2) and at least one compound (ii) selected from thioglycolic acid, thiolactic acid, cysteine, acetylcysteine, cysteamine, acylcysteamine, salts thereof and ester derivatives thereof. Hair processing agents contain a compound of the formula (2), a surfactant and water, and are emulsified. Hair processing agents contain a compound of the formula (2) and a specific perfume. wherein X is a structure selected from —O—, —S—, —NH— and —NR$^1$—; R$^1$ is an alkyl group of 1 to 6 carbon atoms; Y is an oxygen atom or a sulfur atom; in the formula (1), Z is a divalent organic residue having at least one mercapto group; in the formula (2), R is a divalent organic residue optionally having a mercapto group; and R$^2$ is a hydrogen atom or an alkyl group of 1 to 6 carbon atoms.

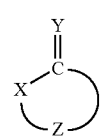

(1)

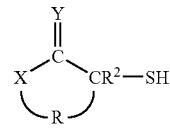

(2)

19 Claims, 1 Drawing Sheet

HAIR PROCESSING AGENT AND METHOD FOR PERMANENT WAVING HAIR

CROSS REFERENCE TO RELATED APPLICATION

This application is an application filed under 35 U.S.C. §111 (a) claiming benefit pursuant to 35 U.S.C. §119 (e) of the filing dates of Provisional Application Nos. 60/639,807, 60/668,093, 60/668,090 and 60/668,612 filed Dec. 29, 2004, Apr. 5, 2005, Apr. 5, 2005 and Apr. 6, 2005, respectively, pursuant to U.S.C. §111(b).

FIELD OF THE INVENTION

The present invention relates to a novel hair processing agent containing a cyclic mercapto compound, and a method for the permanent waving of hair.

BACKGROUND OF THE INVENTION

It is known that permanent waves are created through two steps, i.e., reductive splitting of cystine (disulfide) bonds of hair by the action of a reducing agent, and subsequent neutralization or fixing with an oxidizing agent, whereby the cystine bonds are restored.

The permanent processing of hair has generally used the so-called keratin reducing substances such as thioglycolic acid, cysteine, acetylcysteine and salts thereof. These keratin reducing substances exhibit a practical performance for permanent hair processing under alkaline conditions, and therefore most permanent solutions are rendered alkaline with a pH of approximately 9.5. However, the alkaline permanent solutions are known to damage the hair and scalp. To solve such problems, keratin reducing substances usable at a neutral to weakly acidic pH range (pH: 3-7.5 at 25° C.) have been developed.

For example, monoglycerol esters of thioglycolic acid have been studied as the keratin reducing substances usable at the above pH range (for example, Patent Document 1). To solve skin problems caused by thioglycolic acid esters, mercaptoglycolic acid amide derivatives and mercaptolactic acid amide derivatives are studied (for example, Patent Documents 2 and 3). Further, cysteamines, which are believed to produce effects under weakly acidic conditions, are also studied (for example, Patent Document 4).

[Patent Document 1] JP-A-H08-291031
[Patent Document 2] JP-A-2000-507272
[Patent Document 3] JP-A-2003-528901
[Patent Document 4] JP-A-H03-271214

DISCLOSURE OF THE INVENTION

The monoglycerol esters of thioglycolic acid proposed in Patent Document 1 are liquid to permit excellent handling properties and have specific odor, but have not been in practical use because there have been reports of sensitizing potential probably attributed to the hydroxyl groups in the structure thereof.

The mercaptocarboxylic acid amides proposed in Patent Document 2 are already known to cause skin irritation. Further, there are concerns that the mercaptocarboxylic acid amide derivatives proposed in Patent Document 3 possess a similar sensitizing potential and that sensitizing and skin irritating potentials are caused by insufficient purification or raw-material amine released during storage.

The cysteamines proposed in Patent Document 4 have many problems such as insufficient perming performance under weakly acidic to acidic conditions, and a distinctive odor on permed hair.

As described hereinabove, the keratin reducing substances proposed so far cannot always provide desired hair processing agents.

Although such conventional hair processing agents exhibit a desired perming performance when used at a weakly alkaline pH range, permanent wave processing under weakly alkaline conditions adversely affects the scalp and hair, often resulting in, for example, discolored hair and dryness of hair.

When the traditional hair processing agents are used at a gentle pH in a neutral to weakly acidic range, they cannot always show a satisfactory perming performance in such a pH range. Excessive use to ensure the perming performance can invite other problems such as persistent odor and damage to the skin by the reducing substances. Thus, there has been no hair processing agent capable of desired perming performance.

It is therefore an object of the invention to provide a hair processing agent capable of permanent waving hair even in a neutral to weakly acidic pH range that causes less irritation to the skin.

To solve the aforesaid problems, the present applicant provides a hair processing agent that contains a cyclic mercapto compound according to the invention as a keratin reducing substance. However, it has been newly found that when the hair processing agent contains water, the cyclic mercapto compound is hydrolyzed and consequently the concentration of the cyclic mercapto compound in the agent is reduced with time and the decomposition results in coloring and precipitation to deteriorate the appearance.

Therefore, the present invention has an object of providing a hair processing agent in which the cyclic mercapto compound has improved stability in the presence of water to prevent the over-time reduction of the concentration of the cyclic mercapto compound in the agent and to prevent the coloring and precipitation of the agent, thereby achieving a stable performance and good appearance over a long term.

In the traditional permanent waving of hair with permanent waving agents, a first agent containing a reducing agent (hereinafter, also referred to as the permanent waving first agent) and a second agent containing an oxidizing agent (hereinafter, also referred to as the permanent waving second agent) are used. The reducing agent in the first agent contains a mercapto compound as a main component, as described in the above patent documents, so that the permanent wave processing involves an unpleasant odor.

Accordingly, it is another object of the invention to provide a hair processing agent which is capable of permanent waving hair even at a neutral to weakly acidic pH range that causes less irritation to the skin and in which an unpleasant odor is masked.

The present inventors studied diligently and have found that the use of a specific cyclic mercapto compound as a keratin reducing substance in a permanent waving first agent enables a higher perming performance in a neutral to weakly acidic pH range than is achieved by the known compounds.

The cyclic mercapto compound has been found to possess a higher perming performance in a neutral to acidic pH range than the known compounds. Further studies have found that the use of the cyclic mercapto compound in combination with other keratin reducing substances achieves a high perming performance over a wider pH range.

It has also been found that an emulsified hair processing agent containing the specific cyclic mercapto compound, a surfactant and water exhibits improved stability of the cyclic mercapto compound in the agent.

Furthermore, it has been found that the use of the cyclic mercapto compound as a keratin reducing substance in combination with a specific perfume leads to a hair processing agent which has a higher perming performance in a neutral to weakly acidic pH range than the known compounds and in which an unpleasant odor attributed to the mercapto groups is masked.

The present invention has been completed based on these findings.

The first to fourth aspects of the present invention concern the following (1A) to (10A), (1B) to (12B), (1C) to (15C), and (1D) to (1D), respectively.

(1A) A hair processing agent comprising at least one compound represented by the following formula (1):

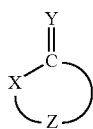

wherein X is a structure selected from the group consisting of —O—, —S—, —NH— and —NR$^1$—; R$^1$ is an alkyl group of 1 to 6 carbon atoms; Y is an oxygen atom or a sulfur atom; and Z is a divalent organic residue having at least one mercapto group.

(2A) The hair processing agent as described in (1A), wherein the compound represented by the formula (1) is a compound represented by the following formula (2):

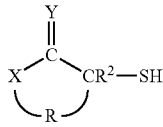

wherein X is a structure selected from the group consisting of —O—, —S—, —NH— and —NR$^1$—; R$^1$ is an alkyl group of 1 to 6 carbon atoms; R$^2$ is a hydrogen atom or an alkyl group of 1 to 6 carbon atoms; Y is an oxygen atom or a sulfur atom; and R is a divalent organic residue optionally having a mercapto group.

(3A) The hair processing agent as described in (1A) or (2A), wherein X in the formula (1) or (2) is —O—, —NH—, —NCH$_3$— or —S—.

(4A) The hair processing agent as described in any one of (1A) to (3A), wherein Y in the formula (1) or (2) is an oxygen atom.

(5A) The hair processing agent as described in any one of (2A) to (4A), wherein R in the formula (2) is an alkylene group.

(6A) The hair processing agent as described in any one of (2A) to (4A), wherein R in the formula (2) is an alkylene group having one or more mercapto groups.

(7A) The hair processing agent as described in (1A) or (2A), wherein the compound represented by the formula (1) or (2) is at least one compound selected from the group consisting of 2-mercapto-4-butyrolactone (another name; 2-mercapto-4-butanolide), 2-mercapto-4-butyrothiolactone, 2-mercapto-4-butyrolactam, N-methyl-2-mercapto-4-butyrolactam, N-ethyl-2-mercapto-4-butyrolactam, N-(2-methoxy)ethyl-2-mercapto-4-butyrolactam, N-(2-ethoxy)ethyl-2-mercapto-4-butyrolactam, 2-mercapto-4-methyl-4-butyrolactone, 2-mercapto-4-ethyl-4-butyrolactone, 2-mercapto-5-valerolactone, 2-mercapto-5-valerolactam, N-methyl-2-mercapto-5-valerolactam, N-ethyl-2-mercapto-5-valerolactam, N-(2-methoxy)ethyl-2-mercapto-5-valerolactam, N-(2-ethoxy)ethyl-2-mercapto-5-valerolactam and 2-mercapto-6-hexanolactam.

(8A) The hair processing agent as described in any one of (1A) to (7A), wherein the content of the compound represented by the formula (1) or (2) is 0.2 to 30% by mass in terms of reducing substance (:thioglycolic acid).

(9A) The hair processing agent as described in any one of (1A) to (8A), wherein the pH of the hair processing agent is in the range of 2.5 to 8.7.

(10A) A method for permanent waving hair, using the hair processing agent as described in any one of (1A) to (9A).

(1B) A hair processing agent comprising:
(i) at least one compound represented by the following formula (2):

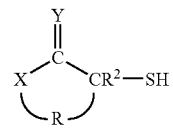

wherein X is a structure selected from the group consisting of —O—, —S—, —NH— and —NR$^1$—; R$^1$ is an alkyl group of 1 to 6 carbon atoms; R$^2$ is a hydrogen atom or an alkyl group of 1 to 6 carbon atoms; Y is an oxygen atom or a sulfur atom; and R is a divalent organic residue optionally having a mercapto group; and (ii) at least one compound selected from the group consisting of thioglycolic acid, thiolactic acid, cysteine, cysteamine, dithioglycol, sulfurous acid, salts thereof, ester derivatives thereof and amide derivatives thereof.

(2B) The hair processing agent as described in (1B), wherein the content of the compound (ii) is 0.01 to 50% by mol relative to the compounds (i) and ii) combined ((ii)/(i+ii)).

(3B) The hair processing agent as described in (1B) or (2B), wherein the pH of the hair processing agent is in the range of 2.5 to 8.7.

(4B) The hair processing agent as described in (1B) to (3B), wherein the compound (ii) is cysteamine, a salt thereof, or an ester derivative thereof.

(5B). The hair processing agent as described in any one of (1B) to (4B), wherein X in the formula (2) is —O—, —NH—, —NCH$_3$— or —S—.

(6B) The hair processing agent as described in any one of (1B) to (5B), wherein Y in the formula (2) is an oxygen atom.

(7B) The hair processing agent as described in any one of (1B) to (6B), wherein R in the formula (2) is an alkylene group.

(8B) The hair processing agent as described in any one of (1B) to (7B), wherein R in the formula (2) is an alkylene group having one or more mercapto groups.

(9B) The hair processing agent as described in any one of (1B) to (8B), wherein the compound represented by the formula (2) is at least one compound selected from the group consisting of 2-mercapto-4-butyrolactone (another name; 2-mercapto-4-butanolide), 2-mercapto-4-butyrothiolactone, 2-mercapto-4-butyrolactam, N-methyl-2-mercapto-4-butyrolactam, N-ethyl-2-mercapto-4-butyrolactam, N-(2-methoxy)ethyl-2-mercapto-4-butyrolactam, N-(2-ethoxy)ethyl-2-mercapto-4-butyrolactam, 2-mercapto-4-methyl-4-butyrolactone, 2-mercapto-4-ethyl-4-butyrolactone, 2-mercapto-5-valerolactone, 2-mercapto-5-valerolactam, N-methyl-2-mercapto-5-valerolactam, N-ethyl-2-mercapto-5-valerolactam, N-(2-methoxy)ethyl-2-mercapto-5-valerolactam, N-(2-ethoxy)ethyl-2-mercapto-5-valerolactam and 2-mercapto-6-hexanolactam.

(10B) The hair processing agent as described in any one of (1B) to (9B), wherein the total content of the compounds (i) and (ii) is 0.2 to 30% by mass in terms of reducing substance (:thioglycolic acid).

(11B) The hair processing agent as described in any one of (1B) to (10B), wherein the hair processing agent is a permanent waving agent.

(12B) A method for permanent waving hair, using the hair processing agent as described in any one of (1B) to (11B).

(1C) A hair processing agent comprising a compound represented by the following formula (2), a surfactant and water, said hair processing agent being emulsified;

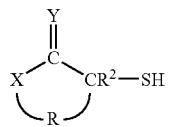

(2)

wherein X is a structure selected from the group consisting of —O—, —S—, —NH— and —NR$^1$—; R$^1$ is an alkyl group of 1 to 6 carbon atoms; R$^2$ is a hydrogen atom or an alkyl group of 1 to 6 carbon atoms; Y is an oxygen atom or a sulfur atom; and R is a divalent organic residue optionally having a mercapto group.

(2C) The hair processing agent as described in (1C), wherein X in the formula (2) is —O—, —NH—, —NCH$_3$— or —S—.

(3C) The hair processing agent as described in (1C) or (2C), wherein Y in the formula (2) is an oxygen atom.

(4C) The hair processing agent as described in any one of (1C) to (3C), wherein R in the formula (2) is an alkylene group.

(5C) The hair processing agent as described in any one of (1C) to (3C), wherein R in the formula (2) is an alkylene group having one or more mercapto groups.

(6C) The hair processing agent as described in any one of (1C) to (5C), wherein the compound represented by the formula (2) is at least one compound selected from the group consisting of 2-mercapto-4-butyrolactone (another name; 2-mercapto-4-butanolide), 2-mercapto-4-butyrothiolactone, 2-mercapto-4-butyrolactam, N-methyl-2-mercapto-4-butyrolactam, N-ethyl-2-mercapto-4-butyrolactam, N-(2-methoxy)ethyl-2-mercapto-4-butyrolactam, N-(2-ethoxy)ethyl-2-mercapto-4-butyrolactam, 2-mercapto-4-methyl-4-butyrolactone, 2-mercapto-4-ethyl-4-butyrolactone, 2-mercapto-5-valerolactone, 2-mercapto-5-valerolactam, N-methyl-2-mercapto-5-valerolactam, N-ethyl-2-mercapto-5-valerolactam, N-(2-methoxy)ethyl-2-mercapto-5-valerolactam, N-(2-ethoxy)ethyl-2-mercapto-5-valerolactam and 2-mercapto-6-hexanolactam.

(7C) The hair processing agent as described in any one of (1C) to (6C), wherein the surfactant is at least one type selected from the group consisting of nonionic surfactant, cationic surfactant, anionic surfactant, amphoteric surfactant, polymeric surfactant and biosurfactant.

(8C) The hair processing agent as described in (7C), wherein the nonionic surfactant is at least one compound selected from the group consisting of polyoxyethylene alkyl ethers, polyoxyethylene alkenyl ethers and polyoxyethylene alkylphenyl ethers containing 10 to 100 moles of polyoxyethylene added.

(9C) The hair processing agent as described in (7C), wherein the nonionic surfactant is a silicone nonionic surfactant.

(10C) The hair processing agent as described in (7C), wherein the biosurfactant has a lipopeptide structure.

(11C) The hair processing agent as described in any one of (1C) to (10C), wherein the content of the compound represented by the formula (2) is 0.2 to 30% by mass in terms of reducing substance (:thioglycolic acid).

(12C) The hair processing agent as described in any one of (1C) to (11C), wherein the surfactant is contained in an amount of 0.1 to 20% by mass.

(13C) The hair processing agent as described in any one of (1C) to (12C), wherein the pH is in the range of 2.5 to 8.7.

(14C) The hair processing agent as described in any one of (1C) to (13C), wherein the hair processing agent is a permanent waving agent.

(15C) A method for permanent waving hair, using the hair processing agent as described in any one of (1C) to (14C).

(1D) A hair processing agent comprising:
(i) at least one compound represented by the following formula (2):

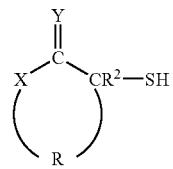

(2)

wherein X is a structure selected from the group consisting of —O—, —S—, —NH— and —NR$^1$—; R$^1$ is an alkyl group of 1 to 6 carbon atoms; R$^2$ is a hydrogen atom or an alkyl group of 1 to 6 carbon atoms; Y is an oxygen atom or a sulfur atom; and R is a divalent organic residue optionally having a mercapto group; and
(ii) at least one perfume selected from the group consisting of (A) hydrocarbons, (B) alcohols, (C) phenols, (D) aldehydes and/or acetals, (E) ketones and/or ketals, (F) ethers, (G) synthetic musks, (H) acids, (I) lactones, (J) esters, (K) nitrogen-containing and/or sulfur-containing and/or halogen-containing compounds, and (L) natural perfumes.

(2D) The hair processing agent as described in (1D), wherein the perfume (ii) is at least one perfume selected from the group consisting of acetyl diisoamylene, anise alcohol, undecalactone, ethyl maltol, orange oil, camphor, geraniol, geranyl nitrile, dimethyl octanol, cyclopentadecanolide, citral, citronellal, dimethyl octenol, methyl dihydrojasmonate, dihydromyrcenol, cinnamic alcohol, spearmint oil, damascone, tansy oil, Triplal, trimethyl undecadienal, γ-decalactone, trimethyl hexenal, nerol, nerolidol, γ-nonalactone, basil oil, pinene, phenylethyl alcohol, phenyl propanal, fenchyl alcohol, hexenal, cis-3-hexenol, peppermint oil, bergamot oil, benzyl formate, benzaldehyde, borneol, methyl ionone, methyl cinnamic aldehyde, methoxy citronellal, menthanol, menthol, menthone, lime oil, raspberry ketone, linalool, linalool oxide, limonene, lemon oil, rosephenone, butylcyclohexyl acetate, isobornyl acetate, dimethyl phenyl ethyl carbinyl acetate, dimethyl benzyl carbinyl acetate, 4-(1-ethoxyvinyl)-3,3,5,5-tetramethylcyclohexanone, cis-p-menthane-7-ol, α, 3,3-trimethylcyclohexanemethyl formate, ethyl 2,2,6-trimethylcyclohexanecarboxylate, 2,6,6-trimethyl-1-crotonylcyclohexane, 2-methyl-4-(2,2,3-trimethyl-3-cyclopentene-1-yl)-2-butene-1-ol, 3-methyl-5-(2,2,3-trimethyl-3-cyclopentene-1-yl)-pentane-2-ol and 2-ethyl-4-(2,2,3-trimethyl-3-cyclopentene-1-yl)-2-butene-1-ol.

(3D) The hair processing agent as described in (1D) or (2D), wherein X in the formula (2) is —O—, —NH—, —NCH$_3$— or —S—.

(4D) The hair processing agent as described in any one of (1D) to (3D), wherein Y in the formula (2) is an oxygen atom.

(5D) The hair processing agent as described in any one of (1D) to (4D), wherein R in the formula (2) is an alkylene group.

(6D) The hair processing agent as described in any one of (1D) to (5D), wherein R in the formula (2) is an alkylene group having one or more mercapto groups.

(7D) The hair processing agent as described in any one of (1D) to (6D), wherein the compound represented by the formula (2) is at least one compound selected from the group consisting of 2-mercapto-4-butyrolactone (another name; 2-mercapto-4-butanolide), 2-mercapto-4-butyrothiolactone, 2-mercapto-4-butyrolactam, N-methyl-2-mercapto-4-butyrolactam, N-ethyl-2-mercapto-4-butyrolactam, N-(2-methoxy)ethyl-2-mercapto-4-butyrolactam, N-(2-ethoxy)ethyl-2-mercapto-4-butyrolactam, 2-mercapto-4-methyl-4-butyrolactone, 2-mercapto-4-ethyl-4-butyrolactone, 2-mercapto-5-valerolactone, 2-mercapto-5-valerolactam, N-methyl-2-mercapto-5-valerolactam, N-ethyl-2-mercapto-5-valerolactam, N-(2-methoxy)ethyl-2-mercapto-5-valerolactam, N-(2-ethoxy)ethyl-2-mercapto-5-valerolactam and 2-mercapto-6-hexanolactam.

(8D) The hair processing agent as described in any one of (1D) to (7D), wherein the content of the compound represented by the formula (2) is 0.2 to 30% by mass in terms of reducing substance (:thioglycolic acid).

(9D) The hair processing agent as described in any one of (1D) to (8D), wherein the pH is in the range of 2.5 to 8.7.

(10D) The hair processing agent as described in (8D) or (9D), wherein the hair processing agent is a permanent waving agent.

(11D) A method for permanent waving hair, using the hair processing agent as described in any one of (1D) to (10D).

(First Aspect)

The cyclic mercapto compounds used in the hair processing agents of the present aspect of the invention possess superior permanent processing practical performance in a neutral to weakly acidic pH range. The hair processing agents exhibit excellent permanent waving practical performance even when the cyclic mercapto compounds are contained at low concentrations. Accordingly, the hair processing agents according to the present aspect provide more stable waving efficiency in a neutral to acidic pH range than general hair processing agents. Furthermore, the hair processing agents achieve reduced skin irritation and sensitizing potential in the application.

Accordingly, the hair processing agents of the present aspect are very useful for permanent waving hair.

(Second Aspect)

The hair processing agents according to the present aspect are particularly suitable and frequently used as permanent waving agents, and contain a cyclic mercapto compound capable of excellent permanent processing practical performance in a neutral to acidic pH range and a mercapto compound capable of excellent permanent waving practical performance in a neutral to weakly alkaline pH range. Consequently, the hair processing agents according to the present aspect display high permanent waving performance in a wide (acidic to weakly alkaline) pH range. The hair processing agents exhibit excellent permanent waving practical performance even when the cyclic mercapto compound is contained at low concentrations. Therefore, the hair processing agents can be used in reduced amounts and provide more stable waving efficiency in a neutral to acidic pH range than general hair processing agents. Furthermore, the hair processing agents achieve reduced skin irritation and sensitizing potential in the application.

Accordingly, the hair processing agents of the present aspect are very useful particularly for the permanent waving of hair.

(Third Aspect)

According to the hair processing agents of the present aspect, the specific cyclic mercapto compounds can display improved stability in the agent even in the presence of water. Consequently, over-time reduction of the concentration of the cyclic mercapto compound in the agent and the consequent coloring and precipitation can be prevented. Therefore, the hair processing agents can maintain stable performance and excellent appearance over a long term.

Specifically, the hair processing agents when used as permanent waving agents can exhibit superior permanent processing performance in a neutral to weakly acidic pH range even after long storage without deteriorated appearance such as discoloration and precipitation. Thus, the hair processing agents attain a higher commercial value. The hair processing agents of the present aspect are therefore suitable as permanent waving agents and highly useful for the permanent waving of hair.

(Fourth Aspect)

The cyclic mercapto compounds used in the hair processing agents of the present aspect possess superior permanent waving practical performance and hair shaping/relaxing performance in a neutral to weakly acidic pH range. The hair processing agents exhibit excellent performance even when the cyclic mercapto compounds are contained at low concentrations.

Accordingly, the hair processing agents when used as permanent waving agents provide more stable waving efficiency in a neutral to acidic pH range than general hair processing agents. Furthermore, the hair processing agents achieve reduced skin irritation and sensitizing potential in the application. Moreover, because the hair processing agents contain specific perfumes, they do not emit a distinctive odor and they possess excellent effects of masking an unpleasant reaction odor during processing and a disagreeable residual odor after the processing, and a pleasant smell remains for a certain time after the processing.

The hair processing agents of the invention may be used as reducing agents in hair relaxers comprising in combination a reducing agent (first agent) and an oxidizing agent (second agent), in which case excellent hair shaping/relaxing effects can be achieved in a wide pH range from mild acidity to mild alkalinity. In particular, such hair relaxers display higher hair shaping/relaxing performance in a weakly acidic to neutral pH range. Therefore, the hair relaxers according to the present invention drastically reduce the damage to the hair and skin and reliably perform straightening and uncurling, as well as curling and other hair processing.

Accordingly, the hair processing agents of the invention are very useful for permanent waving hair. Further, the hair relaxers of the invention are very useful for relaxation, specifically, for straightening frizzy hair and curled hair.

PREFERRED EMBODIMENTS OF THE INVENTION

Figure 1:
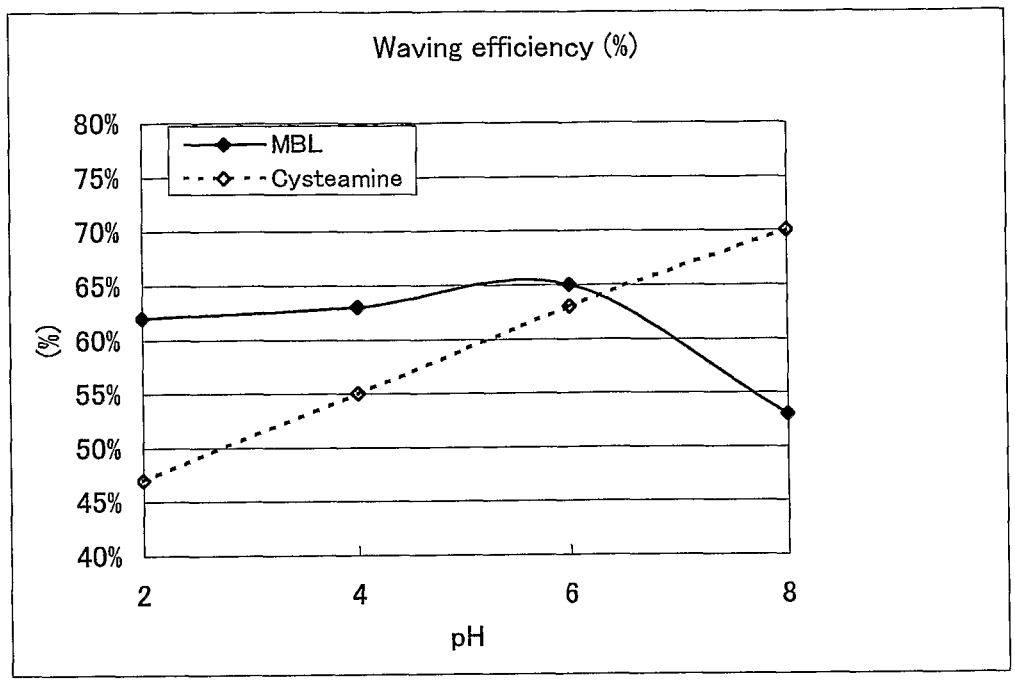
FIG. 1 is a graph showing changes of waving efficiency at various pH according to the second aspect of the invention in which the compounds (i) and (ii) are tested singly.

Hereinbelow, the present invention will be described in detail. As used herein, the term "hair processing agents" comprehends a wide range of processing agents applied to hair. Through the latter step of the processing performed with an oxidizing agent, the hair processing agents provide excellent effects particularly in waving hair or relaxing waved hair, and the hair processing agents in the broad sense are referred to as the "permanent waving agents". Specifically, the hair processing agents include permanent waving agents, curling agents, wave straightening agents for unruly hair or waving hair agents.

[First Aspect] Hair Processing Agent A

The first aspect of the present invention concerns a hair processing agent containing at least one specific cyclic mercapto compound (hereinbelow, referred to as hair processing agent A).

Cyclic Mercapto Compound

The hair processing agents of the invention contain at least one cyclic mercapto compound represented by the following formula (1) and/or (2):

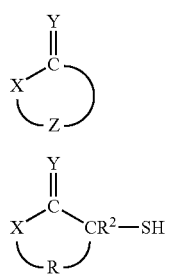

wherein X is a structure selected from the group consisting of —O—, —S—, —NH— and —NR$^1$—; R$^1$ is an alkyl group of 1 to 6 carbon atoms; Y is an oxygen atom or a sulfur atom; in the formula (1), Z is a divalent organic residue having at least one mercapto group; and in the formula (2), R is a divalent organic residue optionally having a mercapto group, and R$^2$ is a hydrogen atom or an alkyl group of 1 to 6 carbon atoms.

X is preferably —O—, —NH—, —NCH$_3$— or —S— in view of preparation of a perm solution, in which case the composition shows relatively high solubility in the perm solution used as aqueous solution.

In view of improving the penetration in hair, R$^1$ is preferably a methyl or ethyl group, more preferably a methyl group.

In the formulae (1) and (2), Y is an oxygen atom or a sulfur atom, and is more preferably an oxygen atom in view of industrial availability and handling properties.

In the formula (1), Z is a divalent organic residue having at least one mercapto (—SH) group. One or more mercapto groups are possible, and one or two mercapto groups are preferable. Particularly, the divalent organic residue is preferably an alkylene group to which a mercapto group(s) is bonded. There is particularly no limitation on the position of the mercapto group(s) bonded to the alkylene group. The mercapto group(s) may be bonded to the alkylene group directly or through an alkylene group or the like (for example, mercaptoethyl group). The main chain of the alkylene group preferably has 3 to 7 carbon atoms. The organic residue may have a branch or a side chain. Examples of the side chains include alkyl groups and alkenyl groups.

Compounds represented by the formula (2) are suitable as the compounds of the formula (1). Examples of the compounds having the formula (1) further include 3-mercapto-4-butyrolactone, 2,3-dimercapto-4-butyrolactone, 2,4-dimercapto-4-butyrolactone, 3,4-dimercapto-4-butyrolactone, 3-mercapto-4-butyrothiolactone, 3-mercapto-4-butyrolactam, 2,3-dimercapto-4-butyrolactam, 2,4-dimercapto-4-butyrolactam, 3,4-dimercapto-4-butyrolactam, 3-mercapto-5-valerolactone, 4-mercapto-5-valerolactone, 2,3-dimercapto-5-valerolactone, 2,4-dimercapto-5-valerolactone, 2,5-dimercapto-5-valerolactone, 3,4-dimercapto-5-valerolactone, 3-mercapto-5-valerothiolactone, 3-mercapto-5-valerolactam, 4-mercapto-5-valerolactam, 2,3-dimercapto-5-valerolactam, 2,4-dimercapto-5-valerolactam, 2,5-dimercapto-5-valerolactam, 3-mercapto-6-hexanolactone, 4-mercapto-6-hexanolactone, 5-mercapto-6-hexanolactone, 2,3-dimercapto-6-hexanolactone, 2,4-dimercapto-6-hexanolactone, 2,5-dimercapto-6-hexanolactone, 3-mercapto-6-hexanolactam, 4-mercapto-6-hexanolactam, 5-mercapto-6-hexanolactam, 2,3-dimercapto-6-hexanolactam, 2,4-dimercapto-6-hexanolactam, 2,5-dimercapto-6-hexanolactam, and N-methyl or N-ethyl derivatives of these lactams.

Of these, 3-mercapto-4-butyrolactone, 2,3-dimercapto-4-butyrolactone, 2,4-dimercapto-4-butyrolactone, 3-mercapto-4-butyrolactam, 2,3-dimercapto-4-butyrolactam, 2,4-dimercapto-4-butyrolactam, 2,3-dimercapto-5-valerolactone, 2,4-dimercapto-5-valerolactone, 2,5-dimercapto-5-valerolactone, 3-mercapto-5-valerolactam, 4-mercapto-5-valerolactam, 2,3-dimercapto-5-valerolactam, 2,4-dimercapto-5-valerolactam and 2,5-dimercapto-5-valerolactam are preferable in view of perming performance and industrial production.

In the formula (2), R$^2$ may be a hydrogen atom, a methyl group, an ethyl group or a propyl group, and is preferably a hydrogen atom, a methyl group or an ethyl group.

In the formula (2), R is a divalent organic residue optionally having a mercapto (—SH) group. R is not particularly limited as long as it is a divalent organic group, and is preferably an alkylene group. The main chain of the alkylene group preferably has 2 to 6 carbon atoms. The organic residue may have a branch or a side chain. Examples of the side chains include alkyl groups and alkenyl groups.

Where R has a mercapto group, one or more mercapto groups are possible, and one or two mercapto groups are preferable. Particularly, the divalent organic residue is preferably an alkylene group to which a mercapto group(s) is bonded. There is particularly no limitation on the position of the mercapto group(s) bonded to the alkylene group. The mercapto group(s) may be bonded to the alkylene group directly or through an alkylene group or the like (for example, mercaptoethyl group).

Preferable examples of R include ethylene and propylene groups because of easy industrial availability.

Specific examples of the compounds represented by the formula (2) include 2-mercapto-3-propiolactone, 2-mercapto-2-methyl-3-propiolactone, 2-mercapto-3-methyl-3-propiolactone, 2-mercapto-3-ethyl-3-propiolactone, 2-mercapto-2,3-dimethyl-3-propiolactone, 2-mercapto-3-propiolactam, 2-mercapto-2-methyl-3-propiolactam, 2-mercapto-3-methyl-3-propiolactam, 2-mercapto-3-ethyl-3-propiolactam, 2-mercapto-2,3-dimethyl-3-propiolactam, 2-mercapto-3-propiothiolactone, 2-mercapto-2-methyl-3-propiothiolactone, 2-mercapto-3-methyl-3-propiothiolactone, 2-mercapto-3-ethyl-3-propiothiolactone, 2-mercapto-2,3-dimethyl-3-propiothiolactone, 2-mercapto-4-butyrolactone, 2-mercapto-2-methyl-4,4-dimethyl-4-butyrolactone, 2-mercapto-3-(2-propenyl)-4-butyrolactone, 2-mercapto-4-methyl-4-butyrolactone, 2-mercapto-2-methyl-4-butyrolactone, 2-mercapto-3-methyl-4-butyrolactone, 2-mercapto-4-methyl-4-butyrolactone, 2-mercapto-3,4-dimethyl-4-butyrolactone, 2-mercapto-2-ethyl-4-butyrolactone, 2-mercapto-3-ethyl-4-butyrolactone, 2-mercapto-4-ethyl-4-butyrolactone, 2-mercapto-4-butyrothiolactone, 2-mercapto-2-methyl-4-butyrothiolactone, 2-mercapto-3-methyl-4-butyrothiolactone, 2-mercapto-4-methyl-4-butyrothiolactone, 2-mercapto-3,4-dimethyl-4-butyrothiolactone, 2-mercapto-2-ethyl-4-butyrothiolactone, 2-mercapto-3-ethyl-4-butyrothiolactone, 2-mercapto-4-ethyl-4-butyrothiolactone, 2-mercapto-4-butyrolactam, 2-mercapto-2-methyl-4-butyrolactam, 2-mercapto-3-methyl-4-butyrolactam, 2-mercapto-4-methyl-4-butyrolactam, 2-mercapto-3,4-dimethyl-4-butyrolactam, 2-mercapto-2-ethyl-4-butyrolactam, 2-mercapto-3-ethyl-4-butyrolactam, 2-mercapto-4-ethyl-4-butyrolactam, 2-mercapto-5-valerolactone, 2-mercapto-2-methyl-5-valerolactone, 2-mercapto-3-methyl-5-valerolactone, 2-mercapto-4-methyl-5-valerolactone, 2-mercapto-5-methyl-5-valerolactone, 2-mercapto-2-ethyl-5-valerolactone, 2-mercapto-3-ethyl-5-valerolactone, 2-mercapto-4-ethyl-5-valerolactone, 2-mercapto-5-ethyl-5-valerolactone, 2-mercapto-5-valerolactam, 2-mercapto-2-methyl-5-valerolactam, 2-mercapto-3-methyl-5-valerolactam, 2-mercapto-4-methyl-5-valerolactam, 2-mercapto-5-methyl-5-valerolactam, 2-mercapto-2-ethyl-5-valerolactam, 2-mercapto-3-ethyl-5-valerolactam, 2-mercapto-4-ethyl-5-valerolactam, 2-mercapto-5-ethyl-5-valerolactam, 2-mercapto-5-valerothiolactone, 2-mercapto-2-methyl-5-valerothiolactone, 2-mercapto-3-methyl-5-valerothiolactone, 2-mercapto-4-methyl-5-valerothiolactone, 2-mercapto-5-methyl-5-valerothiolactone, 2-mercapto-2-ethyl-5-valerothiolactone, 2-mercapto-3-ethyl-5-valerothiolactone, 2-mercapto-4-ethyl-5-valerothiolactone, 2-mercapto-5-ethyl-5-valerothiolactone, 2-mercapto-6-hexanolactone, 2-mercapto-2-methyl-6-hexanolactone, 2-mercapto-3-methyl-6-hexanolactone, 2-mercapto-4-methyl-6-hexanolactone, 2-mercapto-5-methyl-6-hexanolactone, 2-mercapto-6-methyl-6-hexanolactone, 2-mercapto-6-hexanolactam, 2-mercapto-2-methyl-6-hexanolactam, 2-mercapto-3-methyl-6-hexanolactam, 2-mercapto-4-methyl-6-hexanolactam, 2-mercapto-5-methyl-6-hexanolactam, 2-mercapto-6-methyl-6-hexanolactam, 2-mercapto-6-hexanothiolactone, 2-mercapto-2-methyl-6-hexanothiolactone, 2-mercapto-3-methyl-6-hexanothiolactone, 2-mercapto-4-methyl-6-hexanothiolactone, 2-mercapto-5-methyl-6-hexanothiolactone, 2-mercapto-6-methyl-6-hexanothiolactone, 2-mercapto-7-heptanolactone, 2-mercapto-7-heptanothiolactone, 2-mercapto-7-heptanolactam, 2-mercapto-8-octanolactone, 2-mercapto-8-octanothiolactone, 2-mercapto-8-octanolactam, 2-mercapto-9-nonalactone, 2-mercapto-9-nonathiolactone, 2-mercapto-9-nonalactam, and N-methyl or N-ethyl derivatives of these lactams.

Of these, 2-mercapto-4-butyrolactone (another name; 2-mercapto-4-butanolide), 2-mercapto-4-butyrothiolactone, 2-mercapto-4-butyrolactam, N-methyl-2-mercapto-4-butyrolactam, N-ethyl-2-mercapto-4-butyrolactam, N-(2-methoxy)ethyl-2-mercapto-4-butyrolactam, N-(2-ethoxy)ethyl-2-mercapto-4-butyrolactam, 2-mercapto-4-methyl-4-butyrolactone, 2-mercapto-4-ethyl-4-butyrolactone, 2-mercapto-5-valerolactone, 2-mercapto-5-valerolactam, N-methyl-2-mercapto-5-valerolactam, N-ethyl-2-mercapto-5-valerolactam, N-(2-methoxy)ethyl-2-mercapto-5-valerolactam, N-(2-ethoxy)ethyl-2-mercapto-5-valerolactam and 2-mercapto-6-hexanolactam are preferable in view of perming performance and industrial production.

These compounds may be produced by known methods. For example, such compounds can be synthesized by halogenating lactone compounds and lactam compounds followed by introduction of mercapto groups.

Mercaptolactones and mercaptothiolactones may be synthesized by a series of steps in which commercially available lactones or thiolactones are halogenated in accordance with a method described in J. Am. Chem. Soc. 1945, 67. 2218-2220, and the synthesized halides or commercially available halides are produced into objective lacton derivatives by a method described in Ann. 1960, 639. 146-56.

Mercaptolactams may be synthesized by a series of steps in which halides are synthesized by a method described in J. Am. Chem. Soc. 1958. 80. 6233-6237, and the resultant halides are synthesized into objective lactam derivatives by a method described in Ann. 1960, 639. 146-56, similarly to the production of lactones.

The hair processing agent A based on the above cyclic mercapto compound can work at a low pH that will not adversely affect the hair and can exhibit satisfactory waving effects with little irritation to the skin. The reasons for these effects are not clearly understood but are believed to be that the structure of the compound provides higher lipophilicity than conventional reducing agents to enable increased penetration into hair and that because of having a heterocyclic ring, the mercapto compound is easily oxidized particularly under neutral to weakly acidic conditions, so that the hair processing agent can function as reducing agent without being rendered alkaline unlike with the conventional mercapto compounds.

[Hair Processing Agent A]

The hair processing agent A contains at least one cyclic mercapto compound as described above.

The cyclic mercapto compounds of the formula (1) or (2) may be used singly or in combination of two or more kinds.

The cyclic mercapto compounds may be used together with traditional permanent waving compounds such as thioglycolic acid, thiolactic acid, cysteine, acetylcysteine, cysteamine, acylcysteamine, dethioglycol and salts thereof, sulfites, while still achieving the effects of the invention.

The hair processing agent A preferably contains the cyclic mercapto compound in an amount such that the content of the reducing substance (in terms of thioglycol) is 0.2 to 30% by mass, more preferably 0.5 to 20% by mass, still preferably 0.5 to 15% by mass. The reducing substance content in this range eliminates damage to the hair and skin and achieves high waving efficiency.

When the content of the reducing substance is less than 0.2% by mass, performance as hair processing agent often cannot be obtained at all. When the content exceeds 30% by mass, it is more likely that the hair is excessively curled and the cuticle is partly removed, often resulting in greater damage to the hair.

In the invention, the hair processing agent A may be prepared in a desired composition prior to use, or may be prepared on site by mixing agents immediately before use. In the on-site preparation, the undiluted cyclic mercapto compound or crystal of the compound may be added to an agent containing other than the cyclic mercapto compound of the formula (1) and/or (2). Alternatively, a solution in which the cyclic mercapto compound is diluted with an additive such as a swelling agent or a penetration enhancer may be mixed and dissolved in an agent containing other than the cyclic mercapto compound.

The content of the reducing substance (in terms of thioglycolic acid) is a notation of keratin-reducing substance concentration specified with respect to each treatment in the permanent waving agent quality specification for medicated cosmetics in the Pharmaceutical law, and is determined in accordance with the following process.

[Content of reducing substance (in terms of thioglycolic acid)]

A sample, 10 ml, is placed in a 100-ml measuring flask, and purified water conforming with Japanese Standards of Cosmetic Ingredients (hereinafter, simply referred to as "water") is added to make the total volume 100 ml. The solution obtained is used as a test solution.

Exactly 20 ml of the test solution is mixed with 50 ml and 5 ml of water and 30% by mass sulfuric acid, respectively, and the mixture is heated gently and boiled for 5 minutes. After cooling, the solution is titrated with 0.1N iodine solution, and the consumption A ml is obtained (indicator: starch test solution 3 ml).

The titration result is put in the following formula to calculate the content in terms of thioglycolic acid:

$$\text{Reducing substance content (in terms of thioglycolic acid)}(\% \text{ by mass}) = 0.4606 \times A$$

Permanent waving (curling) agents classified in cosmetics are regulated to usage similar to the above value.

When the cyclic mercapto compound is used together with keratin-reducing substances such as thioglycolic acid and thiolactic acid, these are preferably mixed in amounts such that the permanent waving agent prepared has an analytical value of total reducing power within the above range.

In the above case, the cyclic mercapto compound preferably accounts for not less than 50% by mol, more preferably not less than 75% by mol, optimally not less than 90% by mol of the reducing substance content. When the cyclic mercapto compound constitutes less than 50% by mol, waving efficiency in a weakly acidic to neutral range is insufficient.

The hair processing agent A is desirably used in the form of solution, dispersion, emulsion or suspension of the compound having the above formula in a solvent. The solvent is preferably water.

Formulations of the hair processing agent A of the invention are not particularly limited as long as the agent contains the cyclic mercapto compound represented by the formula (1) or (2). Examples of the formulations include liquids, foams, gels, creams and pastes. Depending on the formulation, the agent may be used as various types, including liquid type, spray type, aerosol type, cream type and gel type.

The hair processing agent A may contain various additives depending on the purpose of improving the hair processing performance and usage formulation. Suitable additives include swelling agents, penetration enhancers, buffers, lubricants, thickeners, hair protecting agents, wetting agents, emulsifying agents, pH adjusters, perfumes, colorants, stabilizers and odor masking agents.

The swelling agents and penetration enhancers include ethanol, propanol, isopropanol, 1,2-propylene glycol, 1,3-butanediol, glycerol, ethylcarbitol, benzyl alcohol, benzyloxyethanol, urea and 2-methylpyrrolidone.

The buffers include inorganic buffers, and buffers containing basic amino acids such as arginine, lysine, dimethyl isosorbit, diethoxy ethyl succinate and tri-iso-stearic acid.

The lubricants include paraffin, liquid paraffin, beeswax, squalane, jojoba oil, olive oil, ester oil, triglyceride, vaseline and lanolin.

The thickeners include carboxymethylcellulose, carboxyvinyl polymers, hydroxyethylcellulose, hydroxypropylcellulose, xanthan gum, carrageenan, alginic acid salts, pectin, tragacanth gum, higher alcohols such as lauryl alcohol, cetyl alcohol, stearyl alcohol, isostearyl alcohol, oleyl alcohol and behenyl alcohol, kaolin, fatty acids such as lauric acid, myristic acid, palmitic acid, stearic acid, behenic acid, oleic acid, undecylic acid and isostearic acid, and vaseline.

The hair protecting agents include collagen and keratin hydrolysates and derivatives thereof.

The wetting agents and emulsifying agents include glycerol, diglycerol, propylene glycol, dipropylene glycol, 1,3-butanediol, sorbitol, plant extracts, vitamins, hyaluronic acid salts, chondroitin sulfate, cationic, anionic, amphoteric and nonionic surfactants, ether nonionic surfactants such as polyoxyethylene oleyl ether, polyoxyethylene stearyl ether, polyoxyethylene cetyl ether, polyoxyethylene octyl phenyl ether, polyoxyethylene dodecyl phenyl ether and polyoxyethylene nonyl ether, dimethylpolysiloxane, methylphenylpolysiloxane, and silicon derivatives such as amino-modified silicon oils, alcohol-modified silicon oils, fluorine-modified silicon oils, polyether-modified silicon oils and alkyl-modified silicon oils.

The pH adjusters include hydrochloric acid, organic acids such as citric acid, malic acid, lactic acid, succinic acid and oxalic acid, sodium salts of the acids, and alkaline agents such as ammonia, diethanolamine, triethanolamine, sodium hydroxide, potassium hydroxide, sodium carbonate, sodium hydrogencarbonate, potassium carbonate and potassium hydrogencarbonate.

The stabilizers for preventing excessive reduction include disulfides of reducing compounds and dithiodiglycolic acid.

Other additives include chelating agents such as edetic acid, metal salts thereof, glutamic tetraacetic acid, metal salts thereof, asparaginic tetraacetic acid, metal salts thereof, propyl diamine tetraacetic acid, and metal salts thereof.

The pH of the hair processing agent A is not particularly limited, and the agent may be alkaline with a pH of about 9. Preferably, the pH is in the range of 2.5 to 8.7, more preferably 3.5 to 8.0, optimally 4.0 to 7.5. The alkaline hair processing agent can provide an effect, but the more neutral or weakly acidic the pH level, the greater the effect. The pH is measured by pH meter at room temperature (23° C.).

The hair processing agent A having this pH seldom causes irritation to the skin and does not damage the hair and scalp. The hair processing agent of the invention can exhibit a practical permanent processing performance at the above pH. The above pH level can be achieved by adding the pH adjuster to the agent.

Because of containing the cyclic mercapto compound as described above, the hair processing agent of the invention is excellent in performance of permanent waving hair in a neutral to weakly acidic pH range that causes less irritation to the skin.

[Second Aspect] Hair Processing Agent B

The hair processing agent B of the invention contains (i) a specific cyclic mercapto compound and (ii) another mercapto compound.

Examples of the specific cyclic mercapto compounds (i) include those represented by the above formula (2), and the hair processing agent of the present aspect contains at least one cyclic mercapto compound represented by the formula (2).

Of the compounds represented by the formula (2), 2-mercapto-4-butyrolactone (another name; 2-mercapto-4-butanolide), 2-mercapto-4-butyrothiolactone, 2-mercapto-4-butyrolactam, N-methyl-2-mercapto-4-butyrolactam, N-ethyl-2-mercapto-4-butyrolactam, N-(2-methoxy)ethyl-2-mercapto-4-butyrolactam, N-(2-ethoxy)ethyl-2-mercapto-4-butyrolactam, 2-mercapto-4-methyl-4-butyrolactone, 2-mercapto-4-ethyl-4-butyrolactone, 2-mercapto-5-valerolactone, 2-mercapto-5-valerolactam, N-methyl-2-mercapto-5-valerolactam, N-ethyl-2-mercapto-5-valerolactam, N-(2-methoxy)ethyl-2-mercapto-5-valerolactam, N-(2-ethoxy)ethyl-2-mercapto-5-valerolactam and 2-mercapto-6-hexanolactam are preferable in view of perming performance and industrial production.

(ii) Other Mercapto Compound (Keratin-Reducing Substance)

In the present aspect, the hair processing agent may contain another keratin-reducing substance used in permanent wave application typically together with the above-described cyclic mercapto compound.

Specifically, one compound (ii) selected from the group consisting of thioglycolic acid, thiolactic acid, cysteine, cysteamine, dithioglycol, sulfurous acid, salts thereof, ester derivatives thereof and amide derivatives thereof may be used.

Specific examples of the ester derivatives include N-acetylcysteine and acylcysteine, and further include esters of polyhydric alcohols as disclosed in Patent Document 1. The polyhydric alcohols include 1,2-propanediol, 1,3-propanediol, 1-methoxypropanol (-2), 1-ethoxypropanol (-2), 1,3-butanediol, 1,4-butanediol, diethylene glycol and dipropylene glycol. These polyhydric alcohols may be glycol monoalkyl ethers such as monomethyl ethers and monoethyl ethers.

Specific examples of the amide derivatives include acetamide derivatives substituted with N-branched chain alkyls, and amide derivatives having hydroxyl groups or ether bonds as disclosed in Patent Documents 2 and 3.

The salts may be carboxylates or amine salts, and specific examples include ammonium thioglycolate, monoethanolamine thioglycolate and cysteine hydrochloride.

Of these, cysteamine and derivatives thereof are preferable for use in combination with the compound (i), in which case high permanent waving performance can be achieved in a wide pH range and the amount of the agent required can be reduced.

Composition of Hair Processing Agent B

The hair processing agent B according to the present aspect desirably contains the compound (ii) in an amount of 0.01 to 50% by mol, preferably 5 to 50% by mol, more preferably 20 to 50% by mol relative to the compounds (i) and (ii) combined ((ii)/(i+ii)).

When the content of the compound (ii) is in the above range, the hair processing agent displays a high permanent waving performance in a wide pH range from weak acidity to weak alkalinity, with little irritation to the skin.

The reasons for these effects are not clearly understood but are believed to be that the mercapto compound (i) used as main component of the hair processing agent possesses a structure represented by the formula (1) which provides higher lipophilicity than conventional reducing agents to enable increased penetration into hair and that because of having a ring structure, the mercapto compound is easily oxidized particularly under acidic to neutral conditions, so that the hair processing agent can function as reducing agent without being rendered alkaline unlike with the conventional mercapto compounds.

Hair is made up of a lipophilic cuticle layer, hydrophilic cortex and medulla. It is known that hair is swollen with pH increase and spaces between cuticles are enlarged. Based on this fact, the present inventors assume as follows. The compound (ii) having high hydrophilicity penetrates through the spaces between cuticles enlarged by swelling at pH around 9, while the compound (i) that is more lipophilic is adsorbed to the lipophilic cuticle surface and penetrates in hair regardless of the pH; however, ionization at the mercapto group inhibits penetration, and the diffusion of the compound (i) into the cortex and medulla is slower due to its lipophilicity than the penetration of the compound (ii).

Accordingly, the present inventors believe that the hair processing agent according to the present aspect can exhibit a high permanent waving performance in a wide pH range from weak acidity to weak alkalinity, by the combination of the compound (i) having a high permanent waving performance in an acidic to neutral pH range and the reducing substance (ii) showing high penetration properties in a weakly alkaline pH range.

FIG. 1 shows changes of permanent waving performance (waving efficiency) at various pH obtained using hair processing agents containing either the compound (i) (2-mercapto-4-butyrolactone (MBL)) or the compound (ii) (cysteamine hydrochloride). The hair processing agents tested herein contain the compound at 2% by mass in terms of thioglycolic acid.

As shown in FIG. 1, the hair processing agent containing the compound (i) exhibits high waving efficiency in an acidic to neutral pH range and shows a tendency to slightly lower the waving efficiency at alkaline pH. On the other hand, the hair processing agent containing the compound (ii) displays low waving efficiency at acidic pH, but the waving efficiency linearly increases with the pH increase and reaches a high level at alkaline pH. Consequently, the compounds (i) and (ii) in combination provide a permanent waving performance over a wide pH range.

For use as a permanent waving agent B, the hair processing agent preferably contains the compounds (i) and (ii) in a total mount such that the content in terms of thioglycolic acid is 0.2 to 30% by mass, more preferably 0.5 to 20% by mass, still preferably 0.5 to 15% by mass. This range eliminates damage to the hair and skin and achieves high waving efficiency.

When the content in terms of thioglycolic acid is less than 0.2% by mass, performance as permanent waving agent often cannot be obtained at all. When the content exceeds 30% by mass, it is more likely that the hair is excessively curled and the cuticle is partly removed, often resulting in greater damage to the hair.

Further, the cyclic mercapto compound (i) preferably accounts for not less than 50 mol %, more preferably 50 to 95 mol %, optimally 50 to 80 mol % of the total of the compounds (i) and (ii). When the cyclic mercapto compound (i) constitutes less than 50 mol %, waving efficiency in a weakly acidic to neutral range is often insufficient. When the content of the cyclic mercapto compound (i) is in the above range, the hair processing agent B displays high waving efficiency in a wide pH range from acidity to weak alkalinity.

The ratio (i)/[(i)+(ii)] in the range of 0.01 to 20 mol % provides improved texture of hair regardless of the pH of the hair processing agent. The reason for this effect is not clear but is believed by the present inventors to be that the reducing agent of the invention adheres to the cuticle surface of hair so as to smooth the cuticle lifting on the surface.

The hair processing agent B is desirably used in the form of solution, dispersion, emulsion or suspension of the above compounds (i) and (ii) in a solvent. The solvent is preferably water.

Formulations of the hair processing agent B are not particularly limited as long as the agent contains the compounds (i) and (ii). Examples of the formulations include liquids, foams, gels, creams and pastes. Depending on the formulation, the agent may be used as various types, including liquid type, spray type, aerosol type, cream type and gel type.

The hair processing agent B may contain other active components such as ultraviolet absorbers and hair protecting agents.

The cyclic mercapto compound is generally in an oily state. When the compound is dissolved in water to achieve not less than 10% by mass, dissolution takes a time and the resultant aqueous solution can be separated into two phases. To solve such problems, a surfactant or a lipophilic and hydrophilic solvent such as alcohol may be used.

The surfactant used herein may be cationic, anionic, amphoteric or nonionic, or may be a silicone surfactant or a biosurfactant. Specific examples of the surfactants include those described in the third aspect.

The surfactant permits the compounds (i) and (ii) to be uniformly mixed in the diluting agent and solvent, and the emulsion, etc., obtained is hardly to separate to two phases. The cyclic mercapto compound (i) has a drawback of easy decomposition in the presence of water, but the surfactant prevents the compound from direct contact with water. Consequently, the hair processing agent is stable even during long-term storage to extend the expiration period.

The amount of the surfactant may be determined appropriately depending on the purpose of use and viscosity of the composition, and is generally in the range of 0.01 to 200 parts by mass, preferably 0.02 to 150 parts by mass per 100 parts by mass of the compounds (i) and (ii) combined.

The hair processing agent may contain various additives depending on the purpose of improving the hair processing performance and usage formulation.

Suitable additives include swelling agents, penetration enhancers, buffers, lubricants, thickeners, hair protecting agents, wetting agents, emulsifying agents, pH adjusters, perfumes, colorants, stabilizers and odor masking agents. Specific examples of these additives include those described in the first and the fourth aspect.

When the hair processing agent of the present aspect is used as hair relaxer of reduction-oxidation type for straightening frizzled or curled hair and correcting bed hair as well as for curling hair, usage formulations thereof are not particularly limited. In such applications, the compounds (i) and (ii) may be added to, for example, shampoos, rinsing preparations, conditioners, hair treatments, hair lotions, hair waxes, hair mousses and hair gels.

The pH of the hair processing agent B is not particularly limited, and the agent may be alkaline with a pH of about 9. Preferably, the pH is in the range of 2.5 to 8.7, more preferably 3.5 to 8.0, optimally 4.0 to 7.5. The hair processing agent according to the present aspect can provide an excellent effect regardless of whether the agent is alkaline, neutral or weakly acidic.

The hair processing agent B having this pH seldom causes irritation to the skin and does not damage the hair and scalp. The hair processing agent can exhibit a practical permanent waving performance at the above pH. The above pH level can be achieved by adding the pH adjuster to the agent.

Because of containing the cyclic mercapto compound as described above, the hair processing agent according to the present aspect is excellent in performance of permanent waving hair in a neutral to weakly acidic pH range that causes less irritation to the skin.

In the invention, the hair processing agent may be prepared in a desired composition prior to use, or may be prepared on site by mixing agents immediately before use. In the on-site preparation, a solution containing the aforesaid additives such as diluting agents, solvents, surfactants, swelling agents and penetration enhancers may be mixed and dissolved in the hair processing agent containing the compounds (i) or (ii) and perfume. Alternatively, the hair processing agent may be previously diluted with the diluting agent and solvent, and may be mixed with the additives to give a solution. Still alternatively, each of the compounds (i) and (ii) may be mixed with the additives to give respective solutions, and the solutions obtained may be mixed together to give a solution.

[Third Aspect] Hair Processing Agent C

The hair processing agent C of the present aspect contains the cyclic mercapto compound of the formula (2), a surfactant and water, and is emulsified.

The hair processing agent C based on the above cyclic mercapto compound can work at a low pH that will not adversely affect the hair and can exhibit satisfactory permanent waving effects and hair straightening and uncurling effects with little irritation to the skin. The reasons for these effects are not clearly understood but are believed to be that the structure of the compound provides higher lipophilicity than conventional reducing agents to enable increased penetration into hair and that because of having a heterocyclic ring, the mercapto compound is easily oxidized particularly under neutral to weakly acidic conditions, so that the hair processing agent can function as reducing agent without being rendered alkaline unlike with the conventional mercapto compounds.

The cyclic mercapto compound is easily decomposed over time in the presence of water. Upon contact with water, the cyclic mercapto compound can be partially decomposed to produce ring-opened derivatives. The ring-opened derivatives form carboxylic acids, carboxylic acid amides and carboxylates having mercapto groups. The carboxylic acid amides are formed by reaction with asparaginic acid, glutamic acid, lysine, ammonia, ethanolamine, diethanolamine, cysteine and cysteamine added to the hair processing agent for pH adjustment. The carboxylates are produced by reaction with alcohols added as additives. The hair processing agent C of the present aspect contains a surfactant and water in addition to the above cyclic mercapto compound. The surfactant permits the cyclic mercapto compound to be stably emulsified in the presence of water.

Surfactant and Water

The surfactant for use in the hair processing agent is not particularly limited as long as it can allow the cyclic mercapto compound to be sufficiently emulsified in the presence of water. Preferably, at least one type of surfactant is selected from the group consisting of nonionic surfactant, cationic surfactant, anionic surfactant, amphoteric surfactant, polymeric surfactant, silicone surfactant and biosurfactant.

The nonionic surfactants include:

polyoxyethylene alkyl ethers such as polyoxyethylene (2) lauryl ether, polyoxyethylene (4.2) lauryl ether, polyoxyethylene (9) lauryl ether, polyoxyethylene (21) lauryl ether, polyoxyethylene (23) lauryl ether, polyoxyethylene (25) lauryl ether, polyoxyethylene (2) cetyl ether, polyoxyethylene (5,5) cetyl ether, polyoxyethylene (7) cetyl ether, polyoxyethylene (10) cetyl ether, polyoxyethylene (15) cetyl ether, polyoxyethylene (20) cetyl ether, polyoxyethylene (23) cetyl ether, polyoxyethylene (25) cetyl ether, polyoxyethylene (30) cetyl ether, polyoxyethylene (40) cetyl ether, polyoxyethylene (2) stearyl ether, polyoxyethylene (4) stearyl ether, polyoxyethylene (20) stearyl ether, polyoxyethylene (5) behenyl ether, polyoxyethylene (10) behenyl ether, polyoxyethylene (20) behenyl ether, polyoxyethylene (30) behenyl ether, polyoxyethylene (2) alkyl ether, polyoxyethylene (4) alkyl ether and polyoxyethylene (10) alkyl ether;

polyoxyethylene alkylphenyl ethers such as polyoxyethylene (16) nonylphenyl ether;

polyoxyethylene alkenyl ethers such as polyoxyethylene (7) oleyl ether, polyoxyethylene (10) oleyl ether, polyoxyethylene (15) oleyl ether, polyoxyethylene (20) oleyl ether and polyoxyethylene (50) oleyl ether;

polyoxyethylene polyoxypropylene alkyl ethers such as polyoxyethylene (1) polyoxypropylene (4) cetyl ether, polyoxyethylene (10) polyoxypropylene (4) cetyl ether and polyoxyethylene (1) polyoxypropylene (8) cetyl ether;

polyoxyethylene alkyl alcohols such as polyoxyethylene (5) lanolin alcohol, polyoxyethylene (10) lanolin alcohol and polyoxyethylene (20) lanolin alcohol;

polyoxyethylene polyoxypropylene glycols;

polyoxyethylene polyoxypropylene alkyl glycols;

polyoxyethylene glyceryls such as polyoxyethylene (5) glyceryl monooleate and polyoxyethylene (15) glyceryl monooleate;

polyoxyethylenated castor oils such as polyoxyethylene (3) castor oil, polyoxyethylene (10) castor oil, polyoxyethylene (20) castor oil, polyoxyethylene (40) castor oil, polyoxyethylene (50) castor oil, polyoxyethylene (60) castor oil, polyoxyethylene (5) hydrogenated castor oil, polyoxyethylene (10) hydrogenated castor oil, polyoxyethylene (20) hydrogenated castor oil, polyoxyethylene (30) hydrogenated castor oil, polyoxyethylene (40) hydrogenated castor oil, polyoxyethylene (50) hydrogenated castor oil, polyoxyethylene (60) hydrogenated castor oil and polyoxyethylene (80) hydrogenated castor oil;

polyoxyethylene sorbitan fatty acid esters such as polyoxyethylene (6) sorbit monolaurate, polyoxyethylene (20) sorbitan monolaurate, polyoxyethylene (20) sorbitan monopalmitate, polyoxyethylene (6) sorbitan monostearate, polyoxyethylene (20) sorbitan monostearate, polyoxyethylene (20) sorbitan monoisostearate, polyoxyethylene (20) sorbitan tristearate, polyoxyethylene (6) sorbitan monooleate, polyoxyethylene (20) sorbitan monooleate, polyoxyethylene (20) sorbitan trioleate, polyoxyethylene (20) sorbitan coconut fatty acid ester, polyoxyethylene (10-80) sorbitan monolaurate, polyoxyethylene sorbitan tristearate, polyoxyethylene (20) sorbitan isostearate, polyoxyethylene (150) sorbitan tristearate, polyoxyethylene (6) sorbit tetraoleate, polyoxyethylene (30) sorbit tetraoleate, polyoxyethylene (40) sorbit tetraoleate and polyoxyethylene (60) sorbit tetraoleate;

sorbitan fatty acid esters such as sorbitan monolaurate, sorbitan monopalmitate, sorbitan monostearate, sorbitan monoisostearate, sorbitan monooleate, sorbitan sesquistearate, sorbitan sesquiisostearate, sorbitan sesquioleate, sorbitan tristearate, sorbitan trioleate, sorbitan coconut fatty acid ester, sorbitan isostearate, sorbitan sesquiisostearate and sorbitan distearate;

polyhydric alcohol fatty acid partial esters;

polyoxyethylene polyhydric alcohol fatty acid partial esters;

polyoxyethylene fatty acid monoesters (diesters);

polyglycerine fatty acid esters;

polyoxyethylene fatty acid amides such as polyoxyethylene (5) oleic acid amide;

fatty acid diethanol amides;

polyoxyethylene alkylamines;

triethanolamine fatty acid partial esters;

trialkylamine oxides; and silicone nonionic surfactants such as polyoxyethylene/methylpolysiloxane copolymer (dimethicone copolyol) and aminoethylaminopropylsiloxane/dimethylsiloxane copolymer (amodimethicone).

These surfactants may be used singly or in combination of two or more kinds.

In view of high emulsifying effect and easy handling, the present invention preferably uses at least one surfactant selected from the group consisting of the polyoxyethylene alkyl ethers, polyoxyethylene alkenyl ethers and polyoxyethylene alkylphenyl ethers containing 10 to 100 moles of polyoxyethylene added.

The silicone nonionic surfactants are also preferable in that hair lubrication and antistatic effects are expected. The silicone nonionic surfactants are known as polyether-modified silicone oils and amino-modified silicone oils, but the present invention classifies them as surfactants because they behave as nonionic surfactants. Commercially available nonionic surfactants include SH3771M (manufactured by Toray Dow Corning Silicone) and SM8704C (manufactured by Toray Dow Corning Silicone).

The cationic surfactants include cetyltrimethylammonium chloride, stearyltrimethylammonium chloride, lauryltrimethylammonium chloride, behenyltrimethylammonium chloride, distearyldimethylammonium chloride, dicocoyldimethylammonium chloride, dimethyldiallylammonium chloride/acrylic acid copolymer, dimethyldiallylammonium chloride/acrylic acid/acrylamide terpolymer, benzalkonium chloride, cetylpyridinium chloride, benzethonium chloride, lanolin-derived quaternary ammonium, amidoamines, dimethylaminopropylamide stearate, diethylaminoethylamide stearate, and silicone cationic surfactants (silanes and siloxanes having quaternary ammonium groups in the molecule) disclosed in JP-A-2004-176070.

The anionic surfactants include fatty acid salts; polyoxyethylenealkylethermethylcarboxylic acid salts; alkylbenzenesulfonic acid salts; alkylnaphthalenesulfonic acid salts; alkylsulfonic acid salts; α-olefinsulfonic acid salts; naphthalenesulfonic acid salt-formalin condensates; dialkyl sulfosuccinates such as dioctylsodium sulfosuccinate; disodiumalkylamidoethyl sulfosuccinates; α-sulfonated aliphatic alkyl ester salts; sodiumalkyl isethionates; petroleum sulfonic acid salts; alkylsulfonic acid salts such as sodium lauryl sulfate; alkyl ether sulfates such as ammonium lauryl ether sulfate; sulfated fats and oils; polyoxyethylene alkylsulfuric acid salts such as sodium polyoxyethylene (2,5) laurylsulfate; polyoxyethylene alkyl ether sulfuric acid salts; polyoxyethylene-alkyl phenyl ether sulfuric acid salts; polyoxyethylene styrenated phenyl ether sulfuric acid salts; alkylphosphoric acid salts; polyoxyethylene alkyl ether phosphoric acid salts; polyoxyethylene alkyl phenyl ether phosphoric acid salts; and N-acyl-N-methyltaurine salts such as sodium N-methyl-N-oleyltaurine.

The amphoteric surfactants include:

carboxybetaines such as N,N-dimethyl-N-alkyl-N-carboxymethyl ammonium betaine, N,N,N-trimethyl-N-alkylene ammonium carboxybetaine, betaine lauryldimethylaminoacetate and betaine coconut fatty acid amidopropyldimethylaminoacetate;

sulfobetaines such as N-acylamidopropyl-N',N'-dimethyl-N'-β-hydroxypropylene ammonium sulfobetaine;

N,N-dialkyl-N,N-bis(polyoxyethylene sulfuric acid)ammonium betaines;

imidazolinium betaines such as 2-alkyl-1-hydroxyethyl-1-carboxymethyl imidazolinium betaine; and N-coconut fatty acid acyl-N-carboxymethyl-N-hydroxyethylethylenediaminesodium and N-coconut fatty acid acyl-N-carboxymethyl-N-hydroxyethylethylenediamine/sodium laurylsulfate.

The polymeric surfactants include acrylic acid/methacrylic acid copolymer, polyacrylamide and sodium polyacrylate.

The biosurfactants include lecithins, hydrogenated lecithins, saponins, surfactins and/or salts thereof. As used herein, the biosurfactant means a substance synthesized by prokaryotes in their life activities and having properties similar to surfactants. Of such surfactants, the surfactins are compounds with a lipopeptide structure represented by the following formula (3) and/or their analogous compounds, or are compositions containing two or more kinds of such compounds.

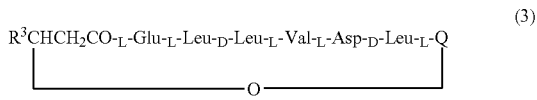

(3)

In the formula (3), Q is an amino acid residue selected from the group consisting of leucine, isoleucine, valine, glycine, serine, alanine, threonine, asparagine, glutamine, asparaginic acid, glutamic acid, lysine, arginine, cysteine, methionine, phenylalanine, tyrosine, tryptophan, histidine, proline, 4-hydroxyproline and homoserine, with leucine, isoleucine and valine being preferable.

$R^3$ is a normal alkyl group of 8 to 14 carbon atoms, an isoalkyl group of 8 to 14 carbon atoms, or an anteiso alkyl group of 8 to 14 carbon atoms. The normal alkyl group is a liner alkyl group, the isoalkyl group is generally $(CH_3)_2CH-(CH_2)_n-$, and the anteiso alkyl group is generally $CH_3-CH_2-CH(CH_3)-(CH_2)_n-$.

The analogous compounds may be such that part of the amino acids in the formula (3) is substituted with other amino acids. Specific examples include, but are not limited to, compounds in which the second L-leucine, fourth L-valine and sixth D-leucine are substituted with other amino acids.

The surfactins are generally produced by prokaryotes, and synthesized surfactins such as by chemical processes may be similarly used. The prokaryotes generally used are *Bacillus* organisms such as *Bacillus subtilis* IAM 1213, IAM 1069, IAM 1259, IAM 1260, IFO 3035 and ATCC 21332.

The surfactin salts include alkali metal salts such as sodium, potassium and lithium salts; alkaline earth metal salts such as calcium and magnesium salts; and organic salts such as trimethylamine, triethylamine, tributylamine, monoethanolamine, diethanolamine, triethanolamine, lysine, arginine and choline salts. Of these, sodium salts of surfactins include surfactin sodium Aminofect® commercially available from SHOWA DENKO K.K.

The water used in the hair processing agent is not particularly limited, but purified water such as ion-exchanged water and distilled water is preferable.

Hair Processing Agent C

The hair processing agent C contains at least the cyclic mercapto compound represented by the formula (2), the surfactant and water, and is emulsified.

For use as a permanent waving agent, the hair processing agent C preferably contains the cyclic mercapto compound of the formula (2) in an amount such that the content of reducing substance (in terms of thioglycol) is 0.2 to 30% by mass, more preferably 0.5 to 20% by mass, still preferably 0.5 to 15% by mass. When the cyclic mercapto compound is contained in this range, damage to the hair and skin can be prevented and high waving efficiency can be achieved.

When the content of the reducing substance is less than 0.2% by mass, performance as hair processing agent often cannot be obtained at all. When the content exceeds 30% by mass, it is more likely that the hair is excessively curled and the cuticle is partly removed, often resulting in greater damage to the hair.

Further, the hair processing agent C preferably contains the surfactant in an amount of 0.1 to 20% by mass, more preferably 0.1 to 15% by mass. The surfactant contained in this amount can allow the cyclic mercapto compound to be sufficiently emulsified in the presence of water and can prevent over-time decomposition of the cyclic mercapto compound in the hair processing agent such as permanent waving agent or hair relaxer. In the emulsified agent, the cyclic mercapto compound is present in a lipophilic region within the micelle, and therefore the odor of the cyclic mercapto compound can be masked.

The process for preparing the hair processing agent C is not particularly limited as long as the specific cyclic mercapto compound of the formula (2) can be emulsified with the surfactant in the solvent water. The mixing methods, orders and conditions may be arbitrary.

Formulations of the hair processing agent C of the invention are not particularly limited as long as the agent contains the cyclic mercapto compound of the formula (2), the surfactant and water and is emulsified. Examples of the formulations include liquids, foams, gels, creams and pastes. Depending on the formulation, the agent may be used as various types, including liquid type, spray type, aerosol type, cream type and gel type. Various additives as described in the first aspect may be added.

The hair processing agent C may contain traditional keratin-reducing substances such as sulfites, bisulfites, thioglycolic acid and monoglycerol esters thereof, thiolactic acid, cysteine, acetylcysteine, cysteamine, acylcysteamine and salts thereof, in amounts that do not adversely affect the effects of the invention.

The pH of the hair processing agent C used as permanent waving agent is not particularly limited, and the agent may be alkaline with a pH of about 9. Preferably, the pH is in the range of 2.5 to 8.7, more preferably 3.5 to 8.0, optimally 4.0 to 7.5.

The alkaline hair processing agent C used as permanent waving agent can provide a permanent waving effect, but the more neutral or weakly acidic the pH level, the greater the effect.

The hair processing agent having the above pH seldom causes irritation to the skin and does not damage the hair and scalp. The hair processing agent of the invention can exhibit a practical permanent processing performance at the above pH. The above pH level can be achieved by adding the pH adjuster to the agent.

Because of containing the cyclic mercapto compound as described above, the hair processing agent of the invention is excellent in performance of permanent waving hair in a neutral to weakly acidic pH range that causes less irritation to the skin.

[Fourth Aspect] Hair Processing Agent D

The hair processing agent D of the invention contains the specific cyclic mercapto compound of the formula (2) and a perfume.

Examples of the cyclic mercapto compounds represented by the formula (2) include those described hereinabove. The hair processing agent based on the cyclic mercapto compound can work at a low pH that will not adversely affect the hair and can exhibit satisfactory permanent waving effects and hair straightening and uncurling effects with little irritation to the skin. The reasons for these effects are not clearly understood but are believed to be that the structure of the compound provides higher lipophilicity than conventional reducing agents to enable increased penetration into hair and that because of having a heterocyclic ring, the mercapto compound is easily oxidized particularly under neutral to weakly acidic conditions, so that the hair processing agent can function as reducing agent without being rendered alkaline unlike with the conventional mercapto compounds.

For use as a permanent waving agent, the hair processing agent D preferably contains the cyclic mercapto compound of the formula (2) in an amount such that the content of reducing substance (in terms of thioglycol) is 0.2 to 30% by mass, more preferably 0.5 to 20% by mass, still preferably 0.5 to 15% by mass. When the cyclic mercapto compound is contained in this range, damage to the hair and skin can be prevented and high waving efficiency can be achieved.

When the content of the reducing substance is less than 0.2% by mass, performance as hair processing agent often cannot be obtained at all. When the content exceeds 30% by mass, it is more likely that the hair is excessively curled and the cuticle is partly removed, often resulting in greater damage to the hair.

Perfume

The present aspect of the invention employs at least one perfume selected from the group consisting of (A) hydrocarbons, (B) alcohols, (C) phenols, (D) aldehydes and/or acetals, (E) ketones and/or ketals, (F) ethers, (G) synthetic musks, (H) acids, (I) lactones, (J) esters, (K) nitrogen-containing and/or sulfur-containing and/or halogen-containing compounds, and (L) natural perfumes.

Specific examples of the perfumes include those disclosed in JP-A-2003-137758.

The hydrocarbons (A) are not particularly limited as long as they are volatile organic compounds composed of carbon and hydrogen. Examples thereof include aliphatic hydrocarbons, alicyclic hydrocarbons, terpene hydrocarbons and aromatic hydrocarbons. Specific examples include 1,3,5-undecatriene, p-cymene, α-pinene, α-phellandrene, β-caryophyllene, β-pinene, Δ-carene, alloocimene, ocimene, dihydromyrcene, dipentene, squalene, cedrene, terpinene, terpinolene, valencene, bisabolene, farnesene, myrcene, limonene, longifolene, adamantane, isolongifolene, camphene, guaiene, diphenyl, diphenylmethane, biphenyl, 3,7-dimethyl-1,3,6-octatriene, 4-isopropyl-1-methyl-2-propenylbenzene, 2,6,6-trimethyl-1-crotonylcyclohexane, 7-methyl-3-methylene-1,6-octadiene, p-ethylstyrene, α-p-dimethylstyrene, isoprene, undecatriene, undecane, octadecadiene, octadecane, octadecene, octane, octene, cumene, sabinene, cyclohexane, cyclohexene, cyclopentadiene, dicyclopentadiene, styrene, decalin, decane, tetradecane, tetralin, dodecane, tridecane, tridecene, naphthalene, nonane, nonene, norbornane, norbornene, hexadecane, hexane, heptadecadiene, heptadecane, heptadecene, heptane and pentadecane.

The alcohols (B) are not particularly limited as long as they are volatile organic compounds with hydroxyl groups. Examples thereof include aliphatic alcohols, alicyclic alcohols, terpene alcohols and aromatic alcohols. Specific examples include 10-undecenol, 1-octene-3-ol, 2,6-nonadienol, 2-tert-butylcyclohexanol, 2-ethylhexanol, 2-heptanol, 3,5,5-trimethylhexanol, 3-octanol, 3-phenylpropyl alcohol, L-menthol, n-decyl alcohol, p,α-dimethylbenzyl alcohol, p-tert-butylcyclohexanol, p-methyldimethylbenzylcarbinol, α, 3,3-trimethyl-2-norbornanemethanol, α-n-amylcinnamic alcohol, α-fenchyl alcohol, β-phenylethyl alcohol, anise alcohol, amber core, ambrinol, isononyl alcohol, isophytol, isopulegol, isoborneol, ethyl linalool, octanol, carveol, geraniol, santalol, cis-3-hexene-1-ol, cis-6-nonenol, citronellol, dihydro-α-terpineol, dihydrocitronellol, dihydromyrcenol, dihydrolinalool, dimethylphenylethylcarbinol, dimethylbenzylcarbinol, cinnamic alcohol, styrallyl alcohol, cedrol, terpineol, terpinen-4-ol, Timberol, geraniol, tetrahydrogeraniol, tetrahydromyrcenol, tetrahydromugol, tetrahydrolinalool, nerol, nerolidol, nonanol, nonyl alcohol, nopol, hydrotropyl alcohol, Bacdanol (2-ethyl-4-(2,2,3-trimethyl-3-cyclopentene-1-yl)-2-butene-1-ol), patchouli alcohol, farnesol, phytol, phenylethylmethylethylcarbinol, phenoxyethyl alcohol, furfuryl alcohol, vetiverol, perilla alcohol, benzyl alcohol, mayol, myrcenol, myrtenol, lavandulol, linalool, 1-(2,2,6-trimethylcyclohexanyl)-hexane-3-ol, 1,1-dimethyl-3-phenylpropanol, 1-decanol, 1-dodecanol, 1-nonene-3-ol, 1-heptanol, 1-pentene-3-ol, 2,2-dimethyl-3-phenylpropanol, 2,4-dimethyl-3-cyclohexene-1-methanol, 2,4-dimethylbenzyl alcohol, 2,4-hexadienol, 2,5,5-trimethyloctahydro-2-naphthol, 2,6-dimethylheptane-2-ol, 2-isobutyl-4-hydroxy-4-methyltetrahydropyran, tetrahydro-4-methyl-2-(2-methyl-1-propenyl)-(2H)pyran, hexahydro-4,6,6,7,8,8-hexamethylcyclopenta-γ-2-benzopyran, 6-(3-pentyl)tetrahydro[2H]pyran-2-one, 2-undecanol, 2-octanol, 2-nonanol, 2-phenylpropyl alcohol, 2-methyl-3-butene-2-ol, 2-methyl-4-(2,2,3-trimethyl-3-cyclopentenyl)-2-butenol, 2-methyl-4-(2,2,3-trimethyl-3-cyclopentenyl)-butanol, 2-methyloctanol, 2-methyldecanol, 2-methoxy-2-phenylethyl alcohol, 3,3-dimethyl-Δ2,β-norbornane-2-ethanol, 3,4,5,6,6-pentamethyl-2-heptanol, 3,6-dimethylocta-3-ol, 3,7-dimethyl-1-octanol, 3,7-dimethyl-7-methoxyocta-2-ol, 3-thujanol, 3-dodecanol, 3-heptanol, 3-methyl-1-phenyl-3-pentanol, 3-methyl-2-butene-1-ol, 3-methyl-5-(2,2,3-trimethyl-3-cyclopentenyl)-pentane-2-ol, 3-methyl-5-phenylpentanol, 3-methylpentanol, 4-isopropylcyclohexanol, 4-thujanol, 4-methyl-3-decene-5-ol, 5-methyl-2-phenyl-2-hexanol, 6,8-dimethyl-2-nonanol, 9-decenol, 9-decene-1-ol, E. G. monobutyl ether, sec-undecylic alcohol, sec-octyl alcohol, sec-nonyl alcohol, α,α,β-trimethylphenylethyl alcohol, α,α-dimethylphenylethyl alcohol, α-isobutylphenylethyl alcohol, α-bisabolol, α-propylphenylethyl alcohol, β,γ-hexenol, β-caryophyllene alcohol, γ-4-dimethyl-3-cyclohexene-1-propanol, alloocimenol, anbestol, isocamphylcyclohexanol, isocyclogeraniol, isodihydrolavandulol, isobutylbenzylcarbinol, undecanol, ethylene glycol, ethylene glycol monoethyl ether, ethylene glycol monobutyl ether, ethylene glycol monopropyl ether, ethylene glycol monomethyl ether, ocimenol, camekol DH, cumin alcohol, geranyl linalool, sabinene hydrate, diethylene glycol, diethylene glycol monoethyl ether, diethylene glycol monobutyl ether, diethylene glycol monopropyl ether, diethylene glycol monomethyl ether, cyclohexylethyl alcohol, cyclomethylenecitronellol, cis-4-hexene-1-ol, cis-p-isopropylcyclohexylmethanol, dihydrocarveol, dipropylene glycol, dipropylene glycol monoethyl ether, dipropylene glycol monobutyl ether, dipropylene glycol monopropyl ether, dipropylene glycol monomethyl ether, dimethyl octanol, dimethylvinylcarbinol, sclareol, decahydro-β-naphthol, tetrahydroalloocimenol, trans-2-octanol, trans-2-hexenol, trans-3-hexene-1-ol, neopentyl glycol, hydrocinnamic alcohol, vanillyl alcohol, pinocarveol, butane-1,3-diol, butane-1,3-diol monoethyl ether, butane-1,3-diol monobutyl ether, butane-1,3-diol monopropyl ether, butane-1,3-diol monomethyl ether, butane-2,3-diol, butane-2,3-diol monoethyl ether, butane-2,3-diol monobutyl ether, butane-2,3-diol monopropyl ether, butane-2,3-diol monomethyl ether, butylene glycol, propylene glycol, propylene glycol monoethyl ether, propylene glycol monobutyl ether, propylene glycol monopropyl ether, propylene glycol monomethyl ether, hexamethylene glycol, hexylene glycol, pentamethylene glycol, muguet alcohol, methyl-β-phenylethyl alcohol, dimethyl octenol, methyl sande furol, cis-p-menthane-7-ol and paramethoxyphenethyl alcohol.

The phenols (C) are not particularly limited as long as they are organic phenolic compounds or derivatives thereof having aroma. Examples thereof include monovalent, divalent and trivalent phenolic compounds, polyphenols, and ether derivatives of these compounds. Specific examples include p-cresol, isoeugenol, estragole, eugenol, cypress thiol, benzyl isoeugenol, benzyl eugenol, methyl isoeugenol, methyl eugenol, yara yara, 2,6-dimethoxy phenol, 4-ethyl guaiacol, 4-methyl guaiacol, 5-propenyl guaiathol, β-naphthol isobutyl ether, p-allyl phenol, p-ethyl phenol, isosafrole, ethyl isoeugenol, catechol dimethyl ether, carvacrol, guaiacol, creosol, safrole, dihydroeugenol, thymol, chavicol, hydroquinone dimethyl ether, vanitrope, bromelia, methoxybenzene, resorcinol dimethyl ether and gingerol.

The aldehydes and acetals (D) are not particularly limited as long as they are volatile organic compounds having aldehyde or acetal groups in the molecule. Examples thereof include aliphatic aldehydes and acetals, terpene aldehydes and acetals, and aromatic aldehydes and acetals. Specific examples include 10-undecenal, 2,4-dimethyl-4,4a,5,9b-tetrahydroindeno[1, 2d]-1,3-dioxin, 2,4-decadienal, 2,6-nonadienal, 2-butyl-4,4,6-trimethyl-1,3-dioxane, 2-hexyl-5-methyl-1,3-dioxolane, 2-methylundecanal, 2-methylundecanal dimethyl acetal, 3-ethyl-2,4-dioxaspiro[5.5]undeca-8-ene, 3-ethyl-8(9),11-dimethyl-2,4-dioxaspiro[5.5]undeca-8-ene, 3-propylbicyclo[2.2.1]-hepta-5-ene-2-carboxaldehyde, 4-isopropyl-5,5-dimethyl-1,3-dioxane, 4-heptanal, 5-methyl-5-propyl-2-(1-methylbutyl)-1,3-dioxane, 2-(2,4-dimethyl-3-cyclohexyl)-methyl-5-(1-methylpropyl)-1,3-dioxane, o-methoxycinnamic aldehyde, p-ethyl-α,α-dimethyldihydrocinnamic aldehyde, o-methoxycinnamic aldehyde, o-methoxybenzaldehyde, p-tolyl aldehyde, 3-cyclohexene-1-carboxaldehyde, dimethyl,α-n-hexyl cinnamic aldehyde, α-amyl cinnamic aldehyde, acetaldehyde, acetaldehyde ethyl linalyl acetal, acetaldehyde diethyl acetal, anise aldehyde, aldehyde C-10, aldehyde C-11, aldehyde C-12, aldehyde C-6, aldehyde C-6 DEA, aldehyde C-6 DMA, aldehyde C-6 PG acetal, aldehyde C-8, aldehyde C-8 DEA, aldehyde C-8 DMA, aldehyde C-9, aldehyde C-9 DEA, aldehyde C-9 DMA, isocyclocitral, ethyl vanillin, canthoxal, cucumber aldehyde, cumin aldehyde, geranial, cyclamen aldehyde, cis-6-nonenal, citral, citronellal, citronellyloxyacetaldehyde, sinensal, Dupical, trans-2-hexenal, trans-2-hexenal diethylacetal, Triplal, neral, hydrotropaldehyde, vanillin, hydroxycitronellal, phenylacetaldehyde, phenylacetaldehyde P. G. acetal, phenylacetaldehyde dimethyl acetal, furfural, Floralozon, heliotropin, helional, perilla aldehyde, bergamal, Vertacetal, vern aldehyde, benzaldehyde, homomyrac aldehyde, myrac aldehyde, melonal, lilal, lilial, 2,4,6-triisopropyl-1,3,5-trioxane, 2,4-undecadienal, 2,4-octadienal, 2,4-dioxa-3-methyl-7,10-methanospiro[5.5]-undecane, 2,4-dodecadienal, 2,4-nonadienal, 2,4-hexadienal, 2,4-heptadienal, 2,5,6-trimethyl-4-heptenal, 2,6,10-trimethyl-5,9-undecadienal, 2-methyl-3-(4-methylphenyl)-propanal, 2-methyl-4-(2,6,6-trimethyl-2-cyclohexenyl)-3-butenal, 2-methylbutanal, 3-phenylpropionic aldehyde, 3-phenylpropionic aldehyde dimethyl acetal, 3-methyl-5-phenylvaleraldehyde, 4-(2,2,6-trimethyl-2(1)-cyclohexene)-2-methylbutanal, 4-(4-methyl-3-cyclohexene-1-ylidene)-pentanal, 4-methyl-2-phenyl-2-pentenal, 5-(hydroxymethyl)-2-furfural, 5,9-dimethyl-4,9-decadienal, 5-methylfurfural, n-valeraldehyde, p-tert-butylhydrocinnamic aldehyde, p-isobutyl-α-methylhydrocinnamic aldehyde, p-isopropylhydrotropaldehyde, p-methylhydrotropaldehyde, p-methylphenylacetaldehyde, p-methylphenoxyacetaldehyde, p-methoxybenzaldehyde, α-n-amyl cinnamic aldehyde diethyl acetal, α-amyl cinnamic aldehyde dimethyl acetal, α-campholene aldehyde, α-methyl cinnamic aldehyde, β-methyl hydrocinnamic aldehyde, γ-n-hexyl cinnamic aldehyde, acetaldehyde ethyl isoeugenyl acetal, acetaldehyde ethyl cis-3-hexenyl acetal, acetaldehyde ethylphenyl ethyl acetal, acetaldehyde ethyl hexyl acetal, acetaldehyde citronellyl ethyl acetal, acetaldehyde citronellyl methyl acetal, acetaldehyde phenyl ethyl n-propyl acetal, aldehyde C-13, aldehyde C-14, aldehyde C-5, aldehyde C-7, aldehyde C-7 DEA, aldehyde C-7 DMA, isovaleraldehyde, octahydro-4,7-methano-1H-indenecarboxaldehyde, caryophyllene aldehyde, geranyl oxyacetaldehyde, safranal, salicylaldehyde, cyclocitral, cis-3-hexenal, trimethyl hexenal, cis-3-hexenal diethyl acetal, cis-4-decenal, citral PG acetal, citral diethyl acetal, citral dimethyl acetal, citronellal EG acetal, dihydroindenyl-2,4-dioxane, octanal, dimethyl octanal, cinnamic aldehyde, decanal diethyl acetal, decanal dimethyl acetal, tetrahydrocitral, dodecanal dimethyl acetal, trans-2-undecenal, trans-2-decene-1-al, trans-2-dodecenal, trans-2-tridecenal, trans-2-nonenal, trans-2-heptenal, trans-2-pentenal, trans-4-decenal, trimethyl undecenal, trimethyl decadienal, hydrotropaldehyde E. G. acetal, hydrotropaldehyde dimethyl acetal, vanillin P. G. acetal, paraldehyde, hydroxycitronellal diethyl acetal, phenylacetaldehyde 2,3-butylene glycol acetal, phenylacetaldehyde 2,4-dihydroxy-4-methylpentane acetal, phenylacetaldehyde diisobutyl acetal, phenoxyacetaldehyde, furfurylacrolein, dimethyl heptanal, heptanal E. G. acetal, heliotropin diethyl acetal, heliotropin dimethyl acetal, benzaldehyde P. G. acetal, benzaldehyde glyceryl acetal, benzaldehyde diethyl acetal, benzaldehyde dimethyl acetal, formaldehyde cyclododecyl ethyl acetal, decanal, methyl decanal, methylnonylacetaldehyde dimethyl acetal, methyl vanillin, methoxydicyclopentadiene carboxaldehyde and methoxycitronellal.

The ketones and ketals (E) are not particularly limited as long as they are volatile organic compounds having ketone or ketal groups in the molecule. Examples thereof include aliphatic ketones and ketals, terpene ketones and ketals, and aromatic ketones and ketals. Specific examples include 2-sec-butylcyclohexanone, 2-acetyl-3,3-dimethylnorbornane, 2-acetyl-5-methylfuran, 2-acetylfuran, 2-butyl-1,4-dioxaspiro[4,4]nonane, 2-hexylcyclopentanone, 3-hydroxy-4,5-dimethyl-2-(5H)-furanone, 5-ethyl-3-hydroxy-4-methyl-2[5H]-furanone, 2-ethyl-4-hydroxy-5-methyl-3[2H]-furanone, 6-methyl-3,5-heptadiene-2-one, d-pulegone, L-carvone, o-tert-butylcyclohexanone, p-tert-butylcyclohexanone, p-methylacetophenone, p-methoxyacetophenone, α-dynascone, α-fenchone, β-methyl naphthyl ketone, acetyl cedrene, acetophenone, anisyl acetone, allyl α-ionone, ionone (α,β), iso E super, isojasmone, isodamascone, isolongifolanone, irone, ethyl isoamyl ketone, ethyl maltol, Cashmeran, chalone, camphor, koavone, cyclotene, cis-jasmone, dihydrocarvone, dihydrojasmone, dibenzyl ketone, cedrenone, sotolon, damascone, damascenone, Trimofix O, nootkatone, furaneol, Plicatone, Florex, Beltfix, verbenone, benzophenone, maltol, methylionone, methylcyclopentenolone, methylheptenone, menthone, raspberry ketone, 1-(4-methoxyphenyl)-1-pentene-3-one, 1-(p-menthene-6-yl)-1-propanone, 1-acetyl-3,3-dimethyl-1-cyclohexene, 2-(1-cyclohexene-1-yl)cyclohexanone, 2,2,5,5-tetramethyl-4-isopropyl-1,3-dioxane, 2,2,5-trimethyl-5-pentylcyclopentanone, 2,3,5-trimethylcyclohexene-4-yl-1-methyl ketone, 2,3-hexadione, 2,3-heptanedione, 2,3-pentadione, 2,4-di-tert-butylcyclohexanone, 2,5,5-trimethyl-2-phenyl-1,3-dioxane, 2,6,10-trimethyl-1-acetyl-2,5,9-cyclododecatriene, 2,6,6-trimethyl-2-cyclohexene-1,4-dione, 2-n-butylidene-3,5,5 (3,3,5)-trimethylcyclohexanone, 2-n-heptylcycloheptanone, 2'-acetonaphthone, 2-undecanone, 2-octanone, 2-cyclopentylcyclopentanone, 2-tridecanone, 2-nonanone, 2-hydroxy-6-isopropyl-3-methyl-2-cyclohexenone, 2-butanone, 2-heptanone, 2-heptylcyclopentanone, 2-pentanone, 2-pentyl-2-cyclopentenone, 2-pentylcyclopentanone, 3,3-dimethylcyclohexyl methyl ketone, 3,4-dimethyl-1,2-cyclopentadione, 3,4-hexadione, 3,5-dimethyl-1,2-cyclopentadione, 3-acetyl-2,5-dimethylfuran, 3-octanone, 3-nonanone, 3-hydroxymethyl-2-nonanone, 3-hexanone, 3-heptanone, 3-heptene-2-one, 3-methyl-4-phenyl-3-butene-2-one, 3-methyl-5-(2,2,3-trimethyl-3-cyclopentenyl)-3-pentene-2-one, 3-methyl-5-propyl-2-cyclohexenone, 4-(4-hydroxy-3-methoxyphenyl)-2-butanone, 4-(4-methoxyphenyl)-3-butene-2-one, 4(5)-acetyl-7,7,9(7,9,9)-trimethylbicyclo[4.3.0]nona-1-ene, 4,7-dihydro-2-(3-pentanyl)-1,3-dioxepin, 4,7-dihydro-2-isoamyl-2-methyl-1,3-dioxepin, 4-tert-amylcyclohexanone, 4-oxoisophorone, 4-cyclohexenyl-4-methyl-2-pentanone, 4-heptanone, 4-methyl-3-pentene-2-one, 4-methyl-4-phenyl-2-pentanone, 4-methylene-3,5,6,6-tetramethyl-2-heptanone, 5-cyclohexadecene-1-one, 5-hydroxy-4-octanone, 5-phenyl-5-methyl-3-hexanone, 5-methyl-2,3-hexadione, 7-methyl-3,5-dihydro-2H-benzodioxepin-3-one, p-hydroxyphenylbutanone (4-(p-hydroxyphenyl)-2-butanone), p-methoxyphenylacetone, α-methyl anisal acetone, acetyl isovaleryl, acetyl caryophyllene, acetyl dimethyl tetrahydrobenzindane, acetoin, acetoketal, acetophenone neopentyl glycol acetal, acetone, atrinon, anisylidene acetone, amyl cyclopentanone, ethyl acetoacetate E. G. ketal, ethyl acetoacetate propylene glycol acetal, oxocedrane, krypton, geranyl acetone, diacetyl, diacetone alcohol, diosphenol, rodinol, cyclohexanone, cyclohexenone, cyclopentanone, cis-2-acetonyl-4-methyltetrahydropyran, dimethyl octenone, gingerol, cedranone, Vitalide, piperitenone, piperitone, piperonylacetone, farnesylacetone, pseudoionone, butylidene acetone, furfural acetone, propiophenone, heliotropyl acetone, Verdoxan, benzylidene acetone, homofuraneol, mesityl oxide, methyl α-furyl ketone, methyl isopropyl ketone, methyl iritone, damascone, methyl cedrilone, methyltetrahydrofuranone, 4-(1-ethoxyvinyl)-3,3,5,5-tetramethylcyclohexanone and 6,7-dihydro-1,1,2,3,3-pentamethyl-4(5H) indanone.

The ethers (F) are not particularly limited as long as they are volatile organic compounds having ether groups in the molecule. Examples thereof include aliphatic ethers, terpene ethers and aromatic ethers. Specific examples include 1,4-cineol, 1,8-cineol, p-cresyl methyl ether, β-caryophyllene oxide, β-naphthyl isobutyl ether, β-naphthyl ethyl ether, β-naphthyl methyl ether, anethole, ambroxan, isoamyl phenylethyl ether, isobornyl methyl ether, grisalva, cyclamber, diphenyl oxide, Cedramber, cedryl methyl ether, theaspirane, nerol oxide, phenylethyl methyl ether, phenylethyl isoamyl ether, Madrox, linalool oxide, limetol, rubofix, rubofleur, rose oxide, rosefuran, 13-oxabicyclo[10.3.0]pentadecane, 1-methylcyclododecyl methyl ether, 2,2,6-trimethyl-6-vinyltetrahydropyran, 2,2-dimethyl-5-(1-methyl-1-propenyl)-tetrahydrofuran, 2-ethylidene-6-isopropoxybicyclo[2.2.1]heptane, 2-oxaspiro[4.7]dodecane, 2-butyl-4,6-dimethyldihydropyran, 2-methyl-2-butenyl phenyl ethyl ether, 3,3,5-trimethylcyclohexyl ethyl ether, 3-oxabicyclo[10.3.0]-pentadeca-6-ene, 4-allylanisole, methylanisole, 5-isopropenyl-2-methyl-2-vinyltetrahydrofuran, 8,9-epoxycedrene, n-decyl vinyl ether, tert-butyl hydroquinone dimethyl ether, α-cedrene epoxide, α-terpinyl methyl ether, allyl phenyl ethyl ether, isoamyl benzyl ether, isolongifolene epoxide, ethyl o-methoxy benzyl ether, ocimene epoxide, geranyl ethyl ether, cyclodecenyl methyl ether, cyclohexyl ethyl ether, cyclohexyl phenyl ethyl ether, citroxide, citronellyl ethyl ether, dibenzyl ether, juniperom, cedrol methyl ether, decyl methyl ether, tricyclodecenyl methyl ether, trimethyl cyclododecatriene epoxide, methyl phenyl ethyl ether, methyl hexyl ether, methyl benzyl ether, limonene oxide, 1,2-dimethoxy benzene, 1,3-dimethoxybenzene, 1,4-dimethoxy-2-tert-butylbenzene, ethylene glycol diethyl ether, ethylene glycol dibutyl ether, ethylene glycol dipropyl ether, ethylene glycol dimethyl ether, diethyl ether, diethylene glycol diethyl ether, diethylene glycol dibutyl ether, diethylene glycol dipropyl ether, diethylene glycol dimethyl ether, dimethyl ether, tetrahydrofuran, diphenyl ether, propylene glycol diethyl ether and propylene glycol dimethyl ether.

The synthetic musks (G) are not particularly limited as long as they are organic compounds having musk scent or similar scent. Specific examples thereof include 10-oxahexadecanolide, 11-oxahexadecanolide, 12-oxahexadecanolide, ambrettolide, ambretone, exaltolide, exaltone, galactoride, cyclohexadecanolide, cyclopentadecanolide, 3-methyl cyclopentadecanolide, cyclopentadecanone, civetone, cervolide, celestolide, tonalide, phantolide, pentalide, formylethyltetramethyltetralin, musk tibetene, muscone, moskene, musk ambrette and versalide.

The acids (H) are not particularly limited as long as they are organic compounds having carboxyl groups in the molecule. Specific examples thereof include phenylacetic acid, 2-ethylbutyric acid, 2-ethylhexanoic acid, 2-decenoic acid, 2-hexenoic acid, 2-methyl-2-pentenoic acid, 2-methylbutyric acid, 2-methylheptanoic acid, 4-pentenoic acid, 4-methylpentanoic acid, acetic acid, isovaleric acid, isobutyric acid, undecanoic acid, undecylenic acid, octanoic acid, oleic acid, geranic acid, cinnamic acid, stearic acid, tiglic acid, decanoic acid, dodecanoic acid, tridecanoic acid, nonanoic acid, valeric acid, hydrocinnamic acid, pyruvic acid, butyric acid, propionic acid, hexanoic acid, heptanoic acid, myristic acid, lactic acid, linolic acid, linolenic acid, levulinic acid, oxalic acid, glutaric acid, citric acid, succinic acid, tartaric acid, terephthalic acid, valinic acid, valine, phytic acid, fumaric acid, benzoic acid, maric acid, maleic acid and malonic acid.

The lactones (I) are not particularly limited as long as they are volatile organic compounds having lactone groups in the molecule. Examples thereof include aliphatic lactones, terpene lactones and aromatic lactones. Specific examples include 6-methylcoumarin, α-angelica lactone, γ-n-butyrolactone, γ-undecalactone, γ-octalactone, γ-decalactone, γ-nonalactone, γ-valerolactone, γ-hexylactone, γ-heptalactone, δ-2-decenolactone, δ-undecalactone, δ-octalactone, δ-decalactone, δ-tetradecalactone, δ-dodecalactone, δ-tridecalactone, δ-nonalactone, δ-hexylactone, ε-decalactone, ε-dodecalactone, aldehyde C-14 (peach), aldehyde C-18 (coconut), whiskey lactone, coumarin, dihydrojasmone lactone, jasmine lactone, jasmolactone, methyl γ-decalactone, menthalactone, 4,6,6(4,4,6)-trimethyltetrahydropyran-2-one, 6-(3-pentenyl)tetrahydropyran-2-one, 7-decene-1,4-lactone, octahydrocoumarin, dihydrocoumarin, dodecalactone, 3-n-butylidenephthalide, 3-n-butylphthalide, 3-propylidenephthalide and 3-propylphthalide.

The esters (J) are not particularly limited as long as they are volatile organic compounds having ester groups in the molecule. Examples thereof include aliphatic esters, terpene esters and aromatic esters. Specific examples include 1-ethynylcyclohexyl acetate, cis-3-hexene-1-yl acetate, 1-octene-3-yl acetate, 2-ethylhexyl acetate, 2-phenoxyethyl isobutyrate, 2-phenoxyethyl propionate, 3,5,5-trimethylhexyl acetate, 3,7-dimethyloctanyl acetate, 3-phenylpropyl acetate, 9-decene-1-yl acetate, L-menthyl acetate, L-menthyl propionate, o-tert-butylcyclohexyl acetate, p-tert-butylcyclohexyl acetate, p-cresyl acetate, p-cresyl isobutyrate, p-cresyl phenylacetate, acetyl isoeugenol, acetyl eugenol, anisyl acetate, aphermate (α, 3,3-trimethylcyclohexanemethyl formate), amyl acetate, amyl caprylate, amyl caproate, amyl salicylate, amyl valerate, amyl butyrate, amyl formate, allyl-2-ethyl butyrate, allyl amyl glycolate, allyl isovalerate, allyl octanoate, allyl caprylate, allyl caproate, allyl cyclohexylacetate, allyl cyclohexyloxyacetate, allyl cyclohexylbutyrate, allyl cyclohexylpropionate, allyl cinnamate, allyl phenoxyacetate, allyl butyrate, allyl propionate, allyl heptanoate, allyl benzoate, aldehyde C-16 (strawberry), aldehyde C-19 (pineapple), aldehyde C-20 (raspberry), isoamyl acetate, isoamyl angelate, isoamyl isovalerate, isoamyl isobutyrate, isoamyl undecylenate, isoamyl octanoate, isoamyl salicylate, isoamyl cinnamate, isoamyl decanoate, isoamyl dodecanoate, isoamyl butyrate, isoamyl propionate, isoamyl hexanoate, isoamyl heptinecarbonate, isoamyl benzoate, isoamyl formate, isoamyl levulinate, isoeugenyl phenylacetate, isodihydrolavandulyl acetate, isobutyl acetate, isobutyl isovalerate, isobutyl isobutyrate, isobutyl salicylate, isobutyl cinnamate, isobutyl valerate, isobutyl phenylacetate, isobutyl butyrate, isobutyl propionate, isobutyl hexanoate, isobutyl benzoate, isopulegyl acetate, isopropyl acetate, isopropyl isovalerate, isopropyl isobutyrate, isopropyl cinnamate, isopropyl decanoate, isopropyl phenylacetate, isopropyl butyrate, isopropyl hexanoate, isopropyl benzoate, isopropyl myristate, isobornyl acetate, isobornyl propionate, wintergreen, ethyl 2-tert-butylcyclohexylcarbonate, cis-3-hexenyl methylcarbonate, ethyl 2-ethylhexanoate, ethyl 2-octenoate, ethyl 2-decenoate, ethyl 2-furoate, ethyl 2-hexylacetoacetate, ethyl 2-benzylacetoacetate, ethyl 2-methylvalerate, ethyl 2-methylbutyrate, ethyl 3,5,5-trimethylhexanoate, ethyl 3-hydroxybutyrate, ethyl 3-hydroxyhexanoate, ethyl 3-hydroxy-3-phenylpropionate, ethyl 3-phenylglycidate, ethyl 3-phenylpropionate, methyl pentanoate, ethyl o-methoxybenzoate, ethyl p-anisate, ethyl acetate, ethyl acetoacetate, ethyl isovalerate, ethyl isobutyrate, ethyl octine carbonate, ethyl oleate, ethyl caprinate, ethyl caprylate, ethyl caproate, ethyl crotonate, ethyl geranate, ethyl safranate, ethyl salicylate, ethyl cyclogeraniate, ethyl cinnamate, ethyl valerate, ethyl phenylacetate, ethyl butyrate, ethyl propionate, ethyl heptanoate, ethyl heptine carbonate, ethyl pelargonate, ethyl benzoate, ethyl formate, ethyl myristate, ethyl methyl p-tolylglycidate, ethyl methylphenylglycidate, ethyl laurate, ethyl lactate, ethyl linalyl acetate, ethyl levulinate, ethylene dodecanedioate, ethylene brassylate, eugenyl phenylacetate, octyl acetate, octyl isovalerate, octyl isobutyrate, octyl octanoate, octyl butyrate, octyl heptanoate, octyl formate, ocimenyl acetate, caryophyllene acetate, caryophyllene formate, calicsol, carvyl acetate, guaiac acetate, cuminyl acetate, geranyl acetate, geranyl isovalerate, geranyl isobutyrate, geranyl tiglate, geranyl phenylacetate, geranyl butyrate, geranyl propionate, geranyl hexanoate, geranyl benzoate, geranyl formate, coniferan, santalyl acetate, diethyl adipate, diethyl succinate, diethyl sebacate, diethyl tartrate, diethyl phthalate, diethyl malonate, cyclohexyl acetate, cyclohexyl isovalerate, cyclohexylethyl acetate, cyclohexyl crotonate, cyclohexyl butyrate, cis-3-hexenyl 2-methylbutyrate, cis-3-hexenyl acetate, cis-3-hexenyl angelate, cis-3-hexenyl isovalerate, cis-3-hexenyl isobutyrate, cis-3-hexenyl caproate, cis-3-hexenyl salicylate, cis-3-hexenyl tiglate, cis-3-hexenyl valerate, cis-3-hexenyl phenylacetate, cis-3-hexenyl butyrate, cis-3-hexenyl propionate, cis-3-hexenyl benzoate, cis-3-hexenyl formate, cis-3-hexenyl lactate, citryl acetate, citronellyl acetate, citronellyl isovalerate, citronellyl isobutyrate, citronellyl tiglate, citronellyl phenylacetate, citronellyl butyrate, citronellyl propionate, citronellyl hexanoate, citronellyl formate, dihydrocarvyl acetate, dihydrocuminyl acetate, dihydroterpinyl acetate, dihydromyrcenyl acetate, dimethyl succinate, dimethyl phenyl ethyl carbinyl acetate, dimethyl phthalate, dimethyl benzyl carbinyl acetate, dimethyl benzyl carbinyl isobutyrate, dimethyl benzyl carbinyl butyrate, dimethyl benzyl carbinyl propionate, jasmal, cinnamyl acetate, cinnamyl isovalerate, cinnamyl isobutyrate, cinnamyl cinnamate, cinnamyl tiglate, cinnamyl butyrate, cinnamyl propionate, cinnamyl benzoate, cinnamyl formate, styrallyl acetate, styrallyl isobutyrate, styrallyl propionate, cedryl acetate, cedryl formate, terpinyl acetate, terpinyl isovalerate, terpinyl isobutyrate, terpinyl butyrate, terpinyl propionate, terpinyl formate, decahydro-β-naphthyl formate, decyl acetate, tetrahydrofurfuryl butyrate, tetrahydrogeranyl acetate, tetrahydrofurfuryl acetate, tetrahydromugyl acetate, tetrahydrolinalyl acetate, dodecyl acetate, trans-2-hexenyl acetate, trans-2-hexenyl butyrate, trans-2-hexenyl propionate, trans-2-hexenyl hexanoate, trans-decahydro-β-naphthyl acetate, trans-decahydro-β-naphthyl isobutyrate, triacetin, triethyl citrate, tricyclodecyl acetate, tricyclodecenyl acetate, tricyclodecenyl isobutyrate, tricyclodecenyl propionate, neryl acetate, neryl isobutyrate, neryl butyrate, neryl propionate, neryl formate, nonyl acetate, nopyl acetate, hydrotropic acetate, phenylethyl 2-methylbutyrate, phenylethyl acetate, phenylethyl angelate, phenylethyl isovalerate, phenylethyl isobutyrate, phenylethyl caprylate, phenylethyl salicylate, phenylethyl cinnamate, phenylethyl tiglate, phenylethyl nonanoate, phenylethyl valerate, phenylethyl pivalate, phenylethyl phenylacetate, phenylethyl butyrate, phenylethyl propionate, phenylethyl benzoate, phenylethyl formate, phenylethyl methacrylate, phenylethyl methyl ethyl carbinyl acetate, phenyl salicylate, fenchyl acetate, butyl acetate, butyl angelate, butyl isovalerate, butyl isobutyrate, butyl octanoate, butyl salicylate, butyl decanoate, butyl dodecanoate, butyl valerate, butyl phenylacetate, butyl butyryl lactate, butyl butyrate, butyl propionate, butyl hexanoate, butyl levulinate, furfuryl acetate, prenyl acetate, prenyl angelate, prenyl benzoate, propyl acetate, propyl isovalerate, propyl isobutyrate, propyl octanoate, propyl cinnamate, propyl trans-2, cis-4-decadienoate, propyl phenylacetate, propyl butyrate, propyl propionate, propyl hexanoate, propyl heptanoate, propyl benzoate, propyl formate, hexyl 2-methylbutyrate, hexyl acetate, hexyl isovalerate, hexyl isobutyrate, hexyl octanoate, hexyl salicylate, hexyl tiglate, hexyl phenylacetate, hexyl butyrate, hexyl propionate, hexyl hexanoate, hexyl benzoate, hexyl formate, veticol acetate, vetiveryl acetate, heptyl acetate, heptyl octanoate, heptyl butyrate, heptyl hexanoate, heliotropyl acetate, benzyl 2-methylbutyrate, benzyl acetate, benzyl isovalerate, benzyl isobutyrate, benzyl caprylate, benzyl salicylate, benzyl cinnamate, benzyl tiglate, benzyl dodecanoate, benzyl valerate, benzyl phenylacetate, benzyl butyrate, benzyl propionate, benzyl hexanoate, benzyl benzoate, benzyl formate, pentyl salicylate, myraldyl acetate, myrcenyl acetate, myrtenyl acetate, methyl 1-methyl-3-cyclohexenecarboxylate, ethyl octahydro-4,7-methano[3aH]-3a-carboxylate, methyl 2-nonenoate, methyl 2-furoate, methyl 2-methylbutyrate, methyl 3-nonenoate, methyl 9-undecenoate, methyl o-methoxybenzoate, methyl acetate, methyl atrarate, methyl anisate, methyl angelate, methyl isovalerate, methyl isobutyrate, methyl isohexanoate, methyl octanoate, methyl octine carbonate, methyl oleate, methyl caprinate, methyl caprylate, methyl caproate, methyl geranate, methyl salicylate, methylcyclooctyl carbonate, methyl cyclogeranate, methyl cyclopentylideneacetate, methyl dihydrojasmonate, methyl jasmonate, methyl cinnamate, methyl decanoate, methyl decyne carbonate, methyl tetradecanoate, methyl dodecanoate, methyl trans-2-hexenoate, methyl trans-3-hexenoate, methyl nonanoate, methyl hydroxyhexanoate, methyl valerate, methyl phenylacetate, methyl phenylglycidate, methyl butyrate, methyl heptanoate, methyl heptine carbonate, methyl pelargonate, methyl benzoate, methyl myristate, methyl laurate, methyl lactate, lavandulyl acetate, linalyl acetate, linalyl isovalerate, linalyl isobutyrate, linalyl octanoate, linalyl cinnamate, linalyl butyrate, linalyl propionate, linalyl hexanoate, linalyl benzoate, linalyl formate, rosa musk, rosephenone, rhodinyl acetate, rhodinyl isobutyrate, rhodinyl phenylacetate, rhodinyl butyrate, rhodinyl propionate, rhodinyl formate, 1,3-dimethyl-3-butenyl isobutyrate, 1-acetoxy-2-sec-butyl-1-vinyl cyclohexane, 1-cyclohexe-1-ene isopropyl acetate, 2,4-dimethyl-3-cyclohexylmethyl acetate, 2,4-hexadienyl isobutyrate, 2-methyl-2-methylpentyl valerate, 2-methylbutyl acetate, 2-methylbutyl isovalerate, 3-octyl acetate, 3-phenylpropyl isovalerate, 3-phenylpropyl isobutyrate, 3-phenylpropyl propionate, 3-methylpentyl angelate, 4-methylbenzyl acetate, 5-methyl-3-butyltetrahydropyran-4-yl acetate, 6,10-dimethyl-5,9-undecatriene-2-yl acetate, 9-decene-1-yl propionate, E. G. diacetate, E. G. monobutyl ether acetate, L-carvyl propionate, L-perillyl acetate, L-bornyl propionate, L-menthyl isovalerate, L-menthyl phenylacetate, P. G. dibutyrate, P. G. dipropionate, p-cresyl caprylate, p-cresyl salicylate, α-amylcinnamyl acetate, acetyl vanillin, anisyl propionate, anisyl formate, isobutyl 2-furanpropionate, isobutyl angelate, isobutyl crotonate, ethyl acrylate, ethyl citronellyl oxalate, ethyl stearate, ethyl tiglate, ethyl decadienoate, ethyl dehydrocyclogeranate, ethyl dodecanoate, ethyl trans-2-hexanoate, ethyl trans-3-hexanoate, ethyl nonanoate, ethyl palmitate, ethyl valerate, ethyl pyruvate, eugenyl formate, oxyoctaline formate, nerolidyl acetate, nonanediol-1,3-diacetate, phenyl glycol diacetate, pseudo linalyl acetate, butyl 10-undecenoate, butyl stearate, butyl formate, butyl lactate, furfuryl valerate, propyl 2-furanacrylate and cyclohexyl-2-propenyl acetate. More preferable examples include 1-ethynylcyclohexyl acetate, 1-octene-3-yl acetate, 2-ethylhexyl acetate, 2-phenoxyethyl isobutyrate, 2-phenoxyethyl propionate, 3,5,5-trimethylhexyl acetate, 3,7-dimethyloctanyl acetate, 3-phenylpropyl acetate, 9-decene-1-yl acetate, L-menthyl acetate, L-menthyl propionate, o-tert-butylcyclohexyl acetate, p-tert-butylcyclohexyl acetate, p-cresyl acetate, p-cresyl isobutyrate, p-cresyl phenylacetate, acetyl isoeugenol, acetyl eugenol, anisyl acetate, aphermate, amyl acetate, amyl caprylate, amyl caproate, amyl salicylate, amyl valerate, amyl butyrate, amyl formate, allyl 2-ethylbutyrate, allyl amyl glycolate, allyl isovalerate, allyl octanoate, allyl caprylate, allyl caproate, allyl cyclohexylacetate, allyl cyclohexyloxyacetate, allyl cyclohexylbutyrate, allyl cyclohexylpropionate, allyl cinnamate, allyl phenoxyacetate, allyl butyrate, allyl propionate, allyl heptanoate, allyl benzoate, aldehyde C-16 (strawberry), aldehyde C-19 (pineapple), aldehyde C-20 (raspberry), isoamyl acetate, isoamyl angelate, isoamyl isovalerate, isoamyl isobutyrate, isoamyl undecylenate, isoamyl octanoate, isoamyl salicylate, isoamyl cinnamate, isoamyl decanoate, isoamyl dodecanoate, isoamyl butyrate, isoamyl propionate, isoamyl hexanoate, isoamyl heptine carbonate, isoamyl benzoate, isoamyl formate, isoamyl levulinate, isoeugenyl phenylacetate, isodihydrolavandulyl acetate, isobutyl acetate, isobutyl isovalerate, isobutyl isobutyrate, isobutyl salicylate, isobutyl cinnamate, isobutyl valerate, isobutyl phenylacetate, isobutyl butyrate, isobutyl propionate, isobutyl hexanoate, isobutyl benzoate, isopulegyl acetate, isopropyl acetate, isopropyl isovalerate, isopropyl isobutyrate, isopropyl cinnamate, isopropyl decanoate, isopropyl phenylacetate, isopropyl butyrate, isopropyl hexanoate, isopropyl benzoate, isopropylmyristate, isobornyl acetate, isobornyl propionate, wintergreen, ethyl 2-tert-butylcyclohexylcarbonate, ethyl 2-ethylhexanoate, ethyl 2-octenoate, ethyl 2-decenoate, ethyl 2-furoate, ethyl 2-hexylacetoacetate, ethyl 2-benzylacetoacetate, ethyl 2-methylvalerate, ethyl 2-methylbutyrate, ethyl 3,5,5-trimethylhexanoate, ethyl 3-hydroxybutyrate, ethyl 3-hydroxyhexanoate, ethyl 3-hydroxy-3-phenylpropionate, ethyl 3-phenylglycidate, ethyl 3-phenylpropionate, ethyl o-methoxybenzoate, ethyl p-anisate, ethyl acetate, ethyl acetoacetate, ethyl isovalerate, ethyl isobutyrate, ethyl octine carbonate, ethyl oleate, ethyl caprinate, ethyl caprylate, ethyl caproate, ethyl crotonate, ethyl geranate, ethyl safranate, ethyl salicylate, ethyl cyclogeraniate, ethyl cinnamate, ethyl valerate, ethyl phenylacetate, ethyl butyrate, ethyl propionate, ethyl heptanoate, ethyl heptine carbonate, ethyl pelargonate, ethyl benzoate, ethyl formate, ethyl myristate, ethyl methyl p-tolylglycidate, ethyl methyl phenyl glycidate, ethyl laurate, ethyl lactate, ethyl linalyl acetate, ethyl levulinate, ethylene dodecanedioate, ethylene brassylate, eugenyl phenylacetate, octyl acetate, octyl isovalerate, octyl isobutyrate, octyl octanoate, octyl butyrate, octyl heptanoate, octyl formate, ocimenyl acetate, caryophyllene acetate, caryophyllene formate, calicsol, carvyl acetate, guaiac acetate, cuminyl acetate, geranyl acetate, geranyl isovalerate, geranyl isobutyrate, geranyl tiglate, geranyl phenylacetate, geranyl butyrate, geranyl propionate, geranyl hexanoate, geranyl benzoate, geranyl formate, coniferan, santalyl acetate, diethyl adipate, diethyl succinate, diethyl sebacate, diethyl tartrate, diethyl phthalate, diethyl malonate, cyclohexyl acetate, cyclohexyl isovalerate, cyclohexylethyl acetate, cyclohexyl crotonate, cyclohexyl butyrate, cis-3-hexenyl 2-methylbutyrate, cis-3-hexenyl acetate, cis-3-hexenyl angelate, cis-3-hexenyl isovalerate, cis-3-hexenyl isobutyrate, cis-3-hexenyl caproate, cis-3-hexenyl salicylate, cis-3-hexenyl tiglate, cis-3-hexenyl valerate, cis-3-hexenyl phenylacetate, cis-3-hexenyl butyrate, cis-3-hexenyl propionate, cis-3-hexenyl benzoate, cis-3-hexenyl formate, cis-3-hexenyl lactate, citryl acetate, citronellyl acetate, citronellyl isovalerate, citronellyl isobutyrate, citronellyl tiglate, citronellyl phenylacetate, citronellyl butyrate, citronellyl propionate, citronellyl hexanoate, citronellyl formate, dihydrocarvyl acetate, dihydrocuminyl acetate, dihydroterpinyl acetate, dihydromyrcenyl acetate, dimethyl succinate, dimethyl phenyl ethyl carbinyl acetate, dimethyl phthalate, dimethyl benzyl carbinyl acetate, dimethyl benzyl carbinyl isobutyrate, dimethyl benzyl carbinyl butyrate, dimethyl benzyl carbinyl propionate, jasmal, cinnamyl acetate, cinnamyl isovalerate, cinnamyl isobutyrate, cinnamyl cinnamate, cinnamyl tiglate, cinnamyl butyrate, cinnamyl propionate, cinnamyl benzoate, cinnamyl formate, styrallyl acetate, styrallyl isobutyrate, styrallyl propionate, cedryl acetate, cedryl formate, terpinyl acetate, terpinyl isovalerate, terpinyl isobutyrate, terpinyl butyrate, terpinyl propionate, terpinyl formate, decahydro-β-naphthyl formate, decyl acetate, tetrahydrofurfuryl butyrate, tetrahydrogeranyl acetate, tetrahydrofurfuryl acetate, tetrahydromugyl acetate, tetrahydrolinalyl acetate, dodecyl acetate, trans-2-hexenyl acetate, trans-2-hexenyl butyrate, trans-2-hexenyl propionate, trans-2-hexenyl hexanoate, trans-decahydro-β-naphthyl acetate, trans-decahydro-β-naphthyl isobutyrate, triacetin, triethyl citrate, tricyclodecyl acetate, tricyclodecenyl acetate, tricyclodecenyl isobutyrate, tricyclodecenyl propionate, neryl acetate, neryl isobutyrate, neryl butyrate, neryl propionate, neryl formate, nonyl acetate, nopyl acetate, hydrotropic acetate, phenylethyl 2-methylbutyrate, phenylethyl acetate, phenylethyl angelate, phenylethyl, isovalerate, phenylethyl isobutyrate, phenylethyl caprylate, phenylethyl salicylate, phenylethyl cinnamate, phenylethyl tiglate, phenylethyl nonanoate, phenylethyl valerate, phenylethyl pivalate, phenylethyl phenylacetate, phenylethyl butyrate, phenylethyl propionate, phenylethyl benzoate, phenylethyl formate, phenylethyl methacrylate, phenylethyl methyl ethyl carbinyl acetate, phenyl salicylate, fenchyl acetate, butyl acetate, butyl angelate, butyl isovalerate, butyl isobutyrate, butyl octanoate, butyl salicylate, butyl decanoate, butyl dodecanoate, butyl valerate, butyl phenylacetate, butyl butyryl lactate, butyl butyrate, butyl propionate, butyl hexanoate, butyl levulinate, furfuryl acetate, prenyl acetate, prenyl angelate, prenyl benzoate, propyl acetate, propyl isovalerate, propyl isobutyrate, propyl octanoate, propyl cinnamate, propyl trans-2, cis-4-decadienoate, propyl phenylacetate, propyl butyrate, propyl propionate, propyl hexanoate, propyl heptanoate, propyl benzoate, propyl formate, hexyl 2-methylbutyrate, hexyl acetate, hexyl isovalerate, hexyl isobutyrate, hexyl octanoate, hexyl salicylate, hexyl tiglate, hexyl phenylacetate, hexyl butyrate, hexyl propionate, hexyl hexanoate, hexyl benzoate, hexyl formate, veticol acetate, vetiveryl acetate, heptyl acetate, heptyl octanoate, heptyl butyrate, heptyl hexanoate, heliotropyl acetate, benzyl 2-methylbutyrate, benzyl acetate, benzyl isovalerate, benzyl isobutyrate, benzyl caprylate, benzyl salicylate, benzyl cinnamate, benzyl tiglate, benzyl dodecanoate, benzyl valerate, benzyl phenylacetate, benzyl butyrate, benzyl propionate, benzyl hexanoate, benzyl benzoate, benzyl formate, pentyl salicylate, myraldyl acetate, myrcenyl acetate, myrtenyl acetate, methyl 1-methyl-3-cyclohexenecarboxylate, methyl 2-nonenoate, methyl 2-furoate, methyl 2-methylbutyrate, methyl 3-nonenoate, methyl 9-undecenoate, methyl o-methoxybenzoate, methyl acetate, methyl atrarate, methyl anisate, methyl angelate, methyl isovalerate, methyl isobutyrate, methyl isohexanoate, methyl octanoate, methyl octine carbonate, methyl oleate, methyl caprinate, methyl caprylate, methyl caproate, methyl geranate, methyl salicylate, methylcyclooctyl carbonate, methyl cyclogeranate, ethyl cyclogeranate, methyl cyclopentylideneacetate, methyl dihydrojasmonate, methyl jasmonate, methyl cinnamate, methyl decanoate, methyl decyne carbonate, methyl tetradecanoate, methyl dodecanoate, methyl trans-2-hexenoate, methyl trans-3-hexenoate, methyl nonanoate, methyl hydroxyhexanoate, methyl valerate, methyl phenylacetate, methyl phenylglycidate, methyl butyrate, methyl heptanoate, methyl heptine carbonate, methyl pelargonate, methyl benzoate, methyl myristate, methyl laurate, methyl lactate, lavandulyl acetate, linalyl acetate, linalyl isovalerate, linalyl isobutyrate, linalyl octanoate, linalyl cinnamate, linalyl butyrate, linalyl propionate, linalyl hexanoate, linalyl benzoate, linalyl formate, rosa musk, rosephenone, rhodinyl acetate, rhodinyl isobutyrate, rhodinyl phenylacetate, rhodinyl butyrate, rhodinyl propionate, rhodinyl formate, ethyl 2,2,6-trimethylcyclohexanecarboxylate and methyl dihydrojasmonate.

The nitrogen-containing and/or sulfur-containing and/or halogen-containing compounds (K) are not particularly limited as long as they are fragrant organic compounds containing nitrogen, sulfur and halogen in the molecule. Examples thereof include 2-tert-butylquinoline, 2-isobutylquinoline, 5,6,7,8-tetrahydroquinoxaline, 5-methyl-3-heptanone oxime, 5-methylquinoline, 6-isopropylquinoline, 8-mercaptomenthone, p-methylquinoline, α-amyl cinnamic aldehyde-methyl anthranilate schiff base, isobutylquinoline, indole, indole-hydroxycitronellal schiff base, ethyl anthranilate, geranyl nitrile, citronellyl nitrile, dimethyl sulfide, stemone, thiogeraniol, thioterpineol, thiolinalool, triplal-methyl anthranilate schiff base, hydroxycitronellal-methyl anthranilate schiff base, buccoxime, methyl N-methyl anthranilate, methyl anthranilate, 1-methylpyrrole, 2-(1,4,8-trimethyl-3,7-nonadienyl)pyridine, 2(4)-(2-pinene-10-ylmethyl)pyridine, 2,3,5-trimethylpyrazine, 2,3-diethyl-5-methylpyrazine, 2,3-diethylpyrazine, 2,3-dimethylpyrazine, 2,4,6-trimethyl-4,5-dihydro-1,3,5-dithiazine, 2,5-dimethylpyrazine, 2,6-dimethylpyrazine, 2,6-lutidine, 2-acetyl-3-ethylpyrazine, 2-acetylthiazole, 2-acetylpyrazine, 2-acetylpyridine, 2-acetylpyrrole, 2-amylpyridine, 2-isobutyl-3-methoxypyrazine, 2-isobutylthiazole, 2-isobutylpyridine, 2-isopropyl-4-methylthiazole, 2-ethyl-3,5(3,6)-dimethylpyrazine, 2-ethyl-3-methylpyrazine, 2-ethyl-5-methylpyrazine, 2-ethylthiophenol, 2-ethylpyrazine, 2-ethylbenzenethiol, 2-naphthylmercaptan, 2-pentylpyridine, 2-methyl-3-butanethiol, 2-methyl-3-furanthiol, 2-methyl-4-propyl-1,3-oxathiane, 2-methyl-4-methoxythiazole, 2-methyl-5-vinylpyrazine, 2-methyl-5-methylthiofuran, 2-methylpyrazine, 2-methylbenzoxazole, 2-methoxy-3-isopropylpyrazine, 2-methoxy-3-ethylpyrazine, 2-methoxy-3-methylpyrazine, 2-mercaptoacetic acid, 3,7-dimethyl-2,6-nonadienonitrile, 3-acetylpyridine, 3-isobutylpyridine, 3-thiophenecarboxaldehyde, 3-methylindole, 3-methylthio-1-hexanol, 4-(1,4,8-trimethyl-3,7-nonadienyl)pyridine, 4,5-dimethylthiazole, 4-methyl-5-thiazoleethanol, 4-methyl-5-thiazoleethanol acetate, 4-methyl-5-vinylthiazole, 4-methylthiazole, 5,6,7,8-tetrahydroquinoxaline, 5-acetyl-2,4-dimethylthiazole, 5-ethyl-2-methylpyridine, 5-methyl-2-thiophenecarboxaldehyde, 5-methyl-6,7-dihydrocyclopentapyrazine, 5-methylquinoxaline, 6(p)-tert-butylquinoline, 6-sec-butylquinoline, 8-sec-butylquinoline, n-butyl anthranilate, N-methyl-N-pentyl-2-methyl butylamide, o-thiocresol, S-furfuryl thioacetate, S-furfuryl thiopropionate, S-methyl thiobutyrate, S-methyl methanethiosulfonate, allyl sulfide, cis-3-hexenyl anthranilate, isoamyl mercaptan, isoquinoline, ethyl 3-methylthiopropionate, ethyl thioacetate, ethyl methylthioacetate, quinoline, cuminyl nitrile, di-n-propyl disulfide, diallyl disulfide, diallyl sulfide, cis-3-hexenyl anthranilate, dithiospirofuran, dibutyl sulfide, dipropyl disulfide, dipropyl trisulfide, dimethyl disulfide, dimethyl trisulfide, cinnamyl anthranilate, cinnamyl nitrile, skatole, styryl cyanide, thiazole, thiophene, decahydrocyclododecaoxazole, tetrahydro-p-methylquinoline, tetrahydrothiophene, tetrahydrothiophene-3-one, tetrahydropyrol, tetramethylpyrazine, dodecanonitrile, trithioacetone, tridecene-2-nitrile, trimethylthiazole, piperidine, piperine, pyrazine, pyridine, phenylethyl anthranilate, butyl sulfide, furfuryl disulfide, furfuryl methyl sulfide, furfuryl mercaptan, benzothiazole, mint sulfide, methyl 3-methylthiopropionate, methyl N-2'-methylpentylidene anthranilate, methylthiomethylpyrazine, methyl nicotinate, methyl furfuryl disulfide, methyl propyl acetaldehyde-methyl anthranilate schiff base, methyl propyl disulfide, methyl propyl trisulfide, methyl methylthioacetate, methoxypyrazine, menthyl anthranilate, limonene thiol, allyl isothiocyanate, allyl mercaptan, isopropyl mercaptan, capsaicin, quinine, thialdine, nonanoyl vanillylamide, paradichlorobenzene, bromostyrol, benzyl isothiocyanate, benzyl cyanide, methional, methionol and mercaptoacetic acid.

The natural perfumes (L) are not particularly limited. Specific examples thereof include asarum oil, almond oil, anise oil, abies fir oil, parsnip oil, amyris oil, angelica oil, ambergris tincture, amber sage, ambrette seed oil, ylang ylang oil, orris oil, incense oil, fennel oil, wintergreen oil, elemi oil, oakmoss absolute, oakmoss essence, oakmoss oil, opoponax oil, orris absolute, orange oil, orange flower absolute, cascarilla oil, castoreum resinoid, quassia China oil, quasi absolute, quassia oil, cananga java oil, chamomile oil blue, chamomile oil, calamus oil, cardamom oil, galbanum oil, cajeput oil, caraway oil, callaway oil, guaiac wood oil, guaiac oil, cumin oil, cubeb oil, clove bourbon oil, clove oil, geranium oil, costus oil, copaiba balsam, copaiba oil, coriander oil, sassafras oil, cypress oil, sandalwood oil, cistuslabdanum oil, cedarwood oil, citronella oil, civet absolute, perilla oil, cypress oil, jasmine absolute, juniper berry oil, camphor oil, calamus oil, jonquil absolute, ginger oil, ginger grass oil, cinnamon ceylon oil, sweet fennel oil, styrax oil, spike lavender oil, spearmint oil, sage oil, sage clary oil, geranium oil, geranium grass oil, geranium bourbon oil, celery oil, thyme oil, *thymus vulgaris* oil, tarragon oil, tangerine oil, tuberose absolute, turpentine oil, tolu balsam, tolu balsam oil, tonka bean oil, nutmeg oil, narcissus absolute, neroli bigarade oil, verbena oil, violet leaf absolute, pine oil, basil oil, parsley seed oil, patuli oil, phachun oil, vanilla oil, vanilla resinoid, rose oil, palmarosa oil, hyssop oil, bitter almond oil, bitter fennel oil, cypress oil, cedar oil, pimento berry oil, hyacinth absolute, petitgrain oil, buchu oil, bay oil, petitgrain grass oil, petitgrain Paraguay oil, petitgrain bergamot oil, petitgrain mandarin, petitgrain lemon oil, vetiver oil Java, vetiver bourbon, pennyroyal oil, pepper oil, peppermint oil, Peru balsam, Peru balsam oil, bergamot oil, benzoin oil, benzoin resinoid, bois de rose oil, ho-sho oil, howood oil, marjoram oil, mandarin oil, mimosa absolute, mir oil, musk tonquin tincture, mace oil, melissa oil, eucalyptus oil, lime oil, lavandin oil, labdanum oil, lavender oil, roux oil, lemon oil, lemon grass oil, rose de mai, rose Bulgaria oil, rosemary oil, roman chamomile oil, tansy oil, laurel oil, lovage oil, apple base, cassis base, citrus base and strawberry base. These natural materials may be used in various forms such as essential oils, resinoids, balsams, absolutes, concretes and tinctures.

Of the perfumes (ii), the invention preferably employs at least one compound or essential oil selected from the group consisting of acetyl diisoamylene, anise alcohol, undecalactone, ethyl maltol, orange oil, camphor, geraniol, geranyl nitrile, dimethyl octanol, cyclopentadecanolide, citral, citronellal, dimethyl octenol, methyl dihydrojasmonate, dihydronyrcenol, cinnamic alcohol, spearmint oil, damascone, tansy oil, Triplal, trimethyl undecadienal, γ-decalactone, trimethyl hexenal, nerol, nerolidol, γ-nonalactone, basil oil, pinene, phenylethyl alcohol, phenyl propanal, fenchyl alcohol, hexenal, cis-3-hexenol, peppermint oil, bergamot oil, benzyl formate, benzaldehyde, borneol, methyl ionone, methyl cinnamic aldehyde, methoxy citronellal, menthanol, menthol, menthone, lime oil, raspberry ketone, linalool, linalool oxide, limonene, lemon oil, rosephenone, butylcyclohexyl acetate, isobornyl acetate, dimethyl phenyl ethyl carbinyl acetate, dimethyl benzyl carbinyl acetate, 4-(1-ethoxyvinyl)-3,3,5,5-tetramethylcyclohexanone, cis-p-menthane-7-ol, α, 3,3-trimethylcyclohexanemethyl formate, ethyl 2,2,6-trimethylcyclohexanecarboxylate, 2,6,6-trimethyl-1-crotonylcyclohexane, 2-methyl-4-(2,2,3-trimethyl-3-cyclopentene-1-yl)-2-butene-1-ol, 3-methyl-5-(2,2,3-trimethyl-3-cyclopentene-1-yl)-pentane-2-ol and 2-ethyl-4-(2,2,3-trimethyl-3-cyclopentene-1-yl)-2-butene-1-ol. These perfumes possess a high effect of masking the odor of the mercapto compound represented by the formula (2). Further, the scent thereof changes little and is excellent in long-term stability, and a pleasant smell remains for a certain time even after the hair is washed. Use of a plurality of the above compounds and essential oils in combination provides more preferable results.

Excellent effects of masking the unpleasant odor attributed to ammonias and good scent stability and chemical stability can be achieved when the hair processing agent contains a component A that is a compound or essential oil selected from acetyl diisoamylene, linalool oxide, rosephenone, 2-methyl-4-(2,2,3-trimethyl-3-cyclopentene-1-yl)-2-butene-1-ol, 3-methyl-5-(2,2,3-trimethyl-3-cyclopentene-1-yl)-pentane-2-ol, 2-ethyl-4-(2,2,3-trimethyl-3-cyclopentene-1-yl)-2-butene-1-ol, 4-(1-ethoxyvinyl)-3,3,5,5-tetramethylcyclohexanone, cis-p-menthane-7-ol, nerolidol, raspberry ketone, α,3, 3-trimethylcyclohexanemethyl formate, paramethoxyphenethyl alcohol, tansy oil and basil oil, and a component B that is a compound selected from ethyl 2,2,6-trimethylcyclohexanecarboxylate (thesaron manufactured by TAKASAGO INTERNATIONAL CORPORATION) and 2,6,6-trimethyl-1-crotonylcyclohexane (dihydrodamascone, manufactured by TAKASAGO INTERNATIONAL CORPORATION).

It is also preferable to use as the perfume (ii) at least one compound selected from the group consisting of linalool, methyl dihydrojasmonate, cis-3-hexenol, methyl ionone, Triplal, geraniol, γ-decalactone, dihydromyrcenol, dimethyl benzyl carbinyl acetate and o-tert-butyl cyclohexyl acetate. These compounds possess excellent effects of masking the unpleasant odor of the mercapto compound and ammonia. Also in this case, the perfume compounds may be used in combination with at least one compound selected from the group consisting of geranyl nitrile, isobornyl acetate, raspberry ketone, dimethyl octanol, nerol, γ-nonalactone, borneol, dimethyl phenyl ethyl carbinyl acetate, p-cresol and fenchyl alcohol. Combined use of these perfumes leads to enhanced masking effects.

The perfumes may be used as mixtures containing various perfumes depending on the purpose and user's preference.

For example, suitable mixtures include a mixture containing hexahydro-4,6,6,7,8,8-hexamethylcyclopenta-γ-2-benzopyran, 2-ethyl-4-(2,3,3-trimethyl-3-cyclopentene-1-yl)-2-butene-1-ol, acetyl cedrene, vanillin, α-isomethylionone, α-ionone, β-ionone, methyl dihydrojasmonate, 6-(3-pentyl) tetrahydro[2H]pyran-2-one, citronellol, cis-jasmone, nerol, β-phenyl ethyl alcohol, tricyclodecyl acetate, n-decanal, cis-3-hexanol, cis-3-hexene-1-yl acetate, apple base and citrus base; and a mixture containing acetyl cedrene, 6,7-dihydro-1,1,2,3,3-pentamethyl-4(5H)indanone, 2-ethyl-4-(2,3,3-trimethyl-3-cyclopentene-1-yl)-2-butene-1-ol, vanillin, α-isomethylionone, α-ionone, β-ionone, tricyclodecenyl acetate, allyl hexanoate, allyl heptanoate, ethyl dehydrocyclogeranate, maltol, 4-(p-hydroxyphenyl)-2-butanone, allyl amyl glycolate, cis-3-hexanol, apple base, cassis base, strawberry base and dipropylene glycol.

In the present aspect of the invention, the content of the perfumes is not particularly limited as long as the unpleasant odor can be masked, but is generally in the range of 0.01 to 50% by mass, preferably 0.02 to 40% by mass with respect to the cyclic mercapto compound. When two or more perfumes are used in combination, the total content will be suitably in the above range.

Hair Processing Agent D

The hair processing agent D contains the above-described cyclic mercapto compound and perfume(s) as essential components. The agent may contain appropriate components and additives depending on the purpose and type of the composition.

Such components include diluting agents and solvents. Examples of the preferable diluting agents and solvents in terms of versatility include water, dipropylene glycol, propylene glycol, glycerin, isopropanol, butanol, ethanol and 3-methoxy-3-propanol.

Further, the composition of the invention may contain other active components such as ultraviolet absorbers and hair protecting agents.

The cyclic mercapto compound is generally in an oily state. When the compound is dissolved in water to achieve not less than 10% by mass, dissolution takes a time and the resultant aqueous solution can be separated into two phases. To solve such problems, a lipophilic and hydrophilic solvent such as surfactant or alcohol may be used.

The surfactant used herein may be anionic, cationic, amphoteric or nonionic, or may be a silicon surfactant or a biosurfactant. Specific examples of the surfactants include those described in the third aspect.

When the surfactant is used, a hydrophobic compound can be easily and uniformly dissolved and mixed in the diluting agent and solvent. The hydrophobic compounds to be mixed include some perfumes contained in, for example, hydrocarbons. Moreover, the emulsion obtained with use of the surfactant is uniform and is resistant to separation.

The amount of the surfactant may be determined appropriately depending on the purpose of use and viscosity of the composition, and is generally in the range of 0.01 to 20.0 parts by mass, preferably 0.02 to 15.0 parts by mass per 100 parts by mass of the cyclic mercapto compound.

In addition to the cyclic mercapto compound represented by the formula (2), the hair processing agent D may contain traditional hair processing compounds such as thioglycolic acid and monoglycerol esters thereof, thiolactic acid, cysteine, acetylcysteine, cysteamine, acylcysteamine and salts thereof, sulfites and bisulfites. Specific examples thereof include those described in the second aspect. The amount of these other reducing agents is desirably not more than 50 mol % with respect to the total of the other reducing agents and the mercapto compound of the formula (2).

The hair processing agent D contains the aforesaid components and is used in the form of solution, dispersion, emulsion or suspension in a solvent. The solvent is generally water but is not limited thereto.

The pH of the hair processing agent D is not particularly limited, and the agent may be alkaline with a pH of about 9. Preferably, the pH is in the range of 2.5 to 8.7, more preferably 3.5 to 8.0, optimally 4.0 to 7.5. The alkaline hair processing agent can provide an effect, but the more neutral or weakly acidic the pH level, the greater the effect.

The hair processing agent D has applications including general permanent waving agents and straight permanent agents.

Examples of the formulations of the hair processing agent D include liquids, foams, gels, creams and pastes. Depending on the formulation, the agent may be used as various types, including liquid type, spray type, aerosol type, cream type and gel type.

When the cyclic mercapto compound is used together with the keratin-reducing substances such as thioglycolic acid and thiolactic acid, these are preferably mixed in amounts such that the permanent waving agent prepared has an analytical value of total reducing power (described above) within the above range.

When the other keratin-reducing substances are used, the cyclic mercapto compound of the formula (2) preferably accounts for not less than 50 mol %, more preferably not less than 75 mol %, optimally not less than 90 mol % of the total keratin-reducing substance. When the cyclic mercapto compound constitutes less than 50 mol %, waving efficiency in a weakly acidic to neutral range is insufficient.

In the invention, the hair processing agent may be prepared in a desired composition prior to use, or may be prepared on site by mixing agents immediately before use. In the on-site preparation, a solution containing the aforesaid additives such as diluting agents, solvents, surfactants, swelling agents and penetration enhancers may be mixed and dissolved in the hair processing agent containing the cyclic mercapto compound of the formula (2) (optionally together with the additional reducing agents) and perfume. Alternatively, the hair processing agent may be previously diluted with the diluting agent and solvent, and may be mixed with the additives to give a solution.

[Permanent Waving Method]

Hereinbelow, the permanent waving method of the present invention will be described.

The permanent waving method uses the aforementioned hair processing agents (first to fourth aspects) as permanent waving agents. The use of these permanent waving agents is not particularly limited. For example, the agents can be used for the permanent waving of hair as described below. In the invention, the permanent waving method for hair includes a cystine reduction step and a subsequent neutralization (fixing) step using an oxidizing agent, and comprehends permanent waving treatment, permanent wave smoothing treatment and frizz straightening treatment.

(1) The agent containing the cyclic mercapto compound (any of the hair processing agents A to D) is applied to hair, and the wet hair is wound on rods for shaping.

The frizz straightening treatment does not involve rods. The hair may be first wetted with water, wound on rods, and then given the agent.

(2) The hair wetted with the agent is allowed to stand at room temperature, preferably at elevated temperatures of about 30 to 40° C.

(3) The reductively split cystine bonds are oxidized and restored by a composition containing an oxidizing agent, and the hair is fixed.

(4) The rods are removed from the fixed hair, and the hair is rinsed, shampooed and dried.

The oxidizing agent used in (3) may be a common oxidizing agent, with examples including approximately 3 to 8% by mass aqueous solution of sodium bromate, and diluted solutions of hydrogen peroxide and sodium perborate.

According to the present invention, the hair processing agents as described above have little adverse effects on the skin and low sensitizing potential, and possess superior waving efficiency.

The hair processing agent containing the cyclic mercapto compound of the invention and the composition containing an oxidizing agent will be sometimes referred to as the first agent or the first liquid and the second agent or the second liquid, respectively.

EXAMPLES

The present invention will be described with reference to the following examples, but it should be construed that the invention is in no way limited to the examples.

Synthetic Example 1

Production of 2-mercapto-4-butyrolactone

70% Sodium hydrosulfide (49 g, 0.6 mmol, manufactured by JUNSEI CHEMICAL CO., LTD.) was dissolved in methyl alcohol (500 g, special grade, manufactured by JUNSEI CHEMICAL CO., LTD.) and purified water (500 g, water distilled and passed through an ion exchange filter). The resultant solution was cooled with ice to not more than 10° C. with stirring. To the cooled solution, 2-bromo-4-butyrolactone (100 g, 0.6 mol, manufactured by Tokyo Kasei Kogyo Co., Ltd.) was added dropwise over a period of about 30 minutes. After the completion of the dropwise addition, the mixture was stirred for 10 minutes, and the reaction liquid was concentrated to approximately half of the original volume under reduced pressure. To the concentrated liquid was added ethyl acetate (500 ml, special grade, manufactured by JUNSEI CHEMICAL CO., LTD.) followed by extraction. The aqueous phase obtained was subjected to re-extraction with ethyl acetate (500 ml). The organic phases thus extracted were combined and concentrated and purified by distillation under reduced pressure to give 2-mercapto-4-butyrolactone (23 g, bp: 94° C./0.3 kPa, yield: 32% by mass).

Synthetic Example 2

Production of 2-mercapto-4-methyl-4-butyrolactone

2-Mercapto-4-methyl-4-butyrolactone (18 g, bp: 73° C./0.4 kPa, yield: 25% by mass) was synthesized according to Synthetic Example 1, except that 2-bromo-4-methyl-4-butyrolactone (97 g, 0.5 mol, manufactured by ALDRICH) was used.

Synthetic Example 3

Production of 2-mercapto-4-ethyl-4-butyrolactone (1) Production of 2-bromo-4-ethyl-4-butyrolactone 90% Phosphorus tribromide (2 g, 0.07 mol, manufactured by Wako Pure Chemical Industries, Ltd.) was added to 4-ethyl-4-butyrolactone (46 g, 0.4 mol, manufactured by ALDRICH) at room temperature, followed by stirring for 10 minutes. The reaction liquid was heated to 100° C., and bromine (64 g, 0.4 mol, manufactured by JUNSEI CHEMICAL CO., LTD.) was added dropwise over a period of 1 Hour using a dropping funnel. After the completion of the dropwise addition, the reaction liquid was stirred for 1 hour at 100° C.

After the reaction, the reaction liquid was cooled to room temperature, and water (100 g) was gradually added followed by stirring for 10 minutes. Subsequently, 200 g of ethyl acetate was added to perform extraction. The aqueous phase obtained by separating the organic phase was subjected to re-extraction with ethyl acetate (100 ml).

The organic phases thus extracted were combined and dried over anhydrous sodium sulfate (manufactured by JUNSEI CHEMICAL CO., LTD.). The sodium sulfate was filtered out, and the organic phase was concentrated and distilled under reduced pressure to give 2-bromo-4-ethyl-4-butyrolactone (50 g, bp: 104° C./0.4 kPa, yield: 65% by mass)

(2) Production of 2-mercapto-4-ethyl-4-butyrolactone

Reaction was performed according to Synthetic Example 1 using the above-synthesized 2-bromo-4-ethyl-4-butyrolactone (50 g, 0.26 mol). After the reaction, the liquid was purified by distillation to give 2-mercapto-4-ethyl-4-butyrolactone (8.4 g, bp: 91° C./0.4 kPa, yield: 22% by mass).

Synthetic Example 4

Production of 2-mercapto-4-butyrothiolactone (1) Production of 2-bromo-4-butyrothiolactone 4-Butyrothiolactone (10 g, 0.098 mol, manufactured by ALDRICH) was dissolved in ethyl acetate (90 g, manufactured by JUNSEI CHEMICAL CO., LTD.), and the solution was heated to 63° C. Subsequently, bromine (18 g, 0.11 mol, manufactured by JUNSEI CHEMICAL CO., LTD.) was added dropwise over a period of 15 minutes using a dropping funnel. After the completion of the dropwise addition, the reaction liquid was stirred for 24 hours at 63° C.

After the reaction, the reaction liquid was cooled to room temperature, and water (50 g) was gradually added followed by stirring for 10 minutes. Subsequently, 100 g of ethyl acetate was added to perform extraction.

The aqueous phase obtained by separating the organic phase was subjected to re-extraction with ethyl acetate (100 ml). The organic phases thus extracted were combined and dried over anhydrous sodium sulfate (manufactured by JUNSEI CHEMICAL CO., LTD.). The sodium sulfate was filtered out, and the organic phase was concentrated and distilled under reduced pressure to give 2-bromo-4-butyrothiolactone (7 g, bp: 62° C./0.2 kPa, yield: 37% by mass).

(2) Production of 2-mercapto-4-butyrothiolactone

Reaction was performed according to Synthetic Example 1 using the above-synthesized 2-bromo-4-butyrothiolactone (7 g, 0.037 mol). After the reaction, the liquid was purified by distillation to give 2-mercapto-4-butyrothiolactone (2.2 g, bp: 62° C./0.2 kPa, yield: 45% by mass).

Synthetic Example 5

Production of 2-mercapto-6-hexanolactam (1) Production of 2-bromo-6-hexanolactam A solution of bromine (48 g, 0.3 mol, manufactured by JUNSEI CHEMICAL CO., LTD.) in benzene (100 g, manufactured by JUNSEI CHEMICAL CO., LTD.) was cooled with ice to 10° C. To the cooled solution, 90% phosphorus tribromide (90 g, 0.3 mol, manufactured by Wako Pure Chemical Industries, Ltd.) was added while keeping the temperature of the reaction liquid at not more than 10° C., followed by stirring for 60 minutes. A solution of commercially available 6-hexanolactam (17 g, 0.15 mol, product name: ε-caprolactam, manufactured by Tokyo Kasei Kogyo Co., Ltd.) in benzene (44 g) was added dropwise over a period of 30 minutes using a dropping funnel while keeping the temperature of the reaction liquid at not more than 10° C.

After the completion of the dropwise addition, the reaction liquid was heated to 45° C. and stirred for 5.5 hours. After the reaction, the reaction liquid was poured into 200 g of ice, and the resultant benzene phase was separated and recovered. The recovered benzene phase was concentrated under reduced pressure to give 2-bromo-6-hexanolactam as crude crystal (10.7 g in terms of crude crystal).

(2) Production of 2-mercapto-6-hexanolactam

Reaction was performed according to Synthetic Example 1 using the above-synthesized 2-bromo-6-hexanolactam crude crystal (10.7 g). The reaction liquid was concentrated to approximately half of the original volume under reduced pressure. To the concentrated liquid was added ethyl acetate (100 ml, special grade, manufactured by JUNSEI CHEMICAL CO., LTD.) followed by extraction. The aqueous phase obtained was subjected to re-extraction with ethyl acetate (100 ml). The organic phases thus extracted were combined and concentrated and purified by distillation under reduced pressure to give 2-mercapto-6-hexanolactam as crude crystal. The 2-mercapto-6-hexanolactam crude crystal was subjected to silica gel column chromatography using a hexane:ethyl acetate (2:1 by volume) mixture as mobile phase to give 2-mercapto-6-hexanolactam crystal (3.5 g, yield from 6-hexanolactam: 16% by mass).

Synthetic Example 6

Production of 2,4-dibromobutyric acid bromide 2,4-Dibromobutyric acid bromide was synthesized from 4-butyrolactone according to a method of A. Kamal, et al. (Tetrahedron: Asymmetry 2003, 14, 2587-2594).

Specifically, phosphorus tribromide (2.5 g, 0.43 g atom, manufactured by Tokyo Kasei Kogyo Co., Ltd.) was added to 4-butyrolactone (20 g, 0.23 mol, manufactured by Tokyo Kasei Kogyo Co., Ltd.).

To the resultant solution, bromine (40.4 g, 0.25 mol, manufactured by Wako Pure Chemical Industries, Ltd.) was added dropwise with stirring over a period of about 2 hours while keeping the temperature at not more than 10° C. After the completion of the dropwise addition, the mixture was heated to 70° C., and bromine (40.4 g, 0.25 mol, manufactured by Wako Pure Chemical Industries, Ltd.) was added dropwise over a period of about 30 minutes. After the completion of the dropwise addition, the liquid was heated to 80° C. and stirred at 80° C. for 3 hours.

After the completion of the reaction, a glass tube was inserted to the bottom of the reaction liquid, and nitrogen was blown into the liquid through the glass tube to remove unreacted bromine and hydrogen bromide formed by the reaction. The reaction liquid was then distilled under reduced pressure to give 2,4-dibromobutyric acid bromide (38 g, 0.12 mol, bp: 87-88° C./0.7 kPa, yield: 53%).

Synthetic Example 7

Production of N-methyl-2-bromo-4-butyrolactam

A solution mixture consisting of 40% aqueous methylamine solution (7.9 g, 0.10 mol, manufactured by JUNSEI CHEMICAL CO., LTD.) and water (3.3 g) was cooled to not more than 10° C. To the solution mixture, 2,4-dibromobutyric acid bromide (38 g, 0.12 mol) was added dropwise over a period of 15 minutes while keeping the temperature at not more than 10° C. After the completion of the dropwise addition, the mixture was heated to 30° C. and stirred for 30 minutes. The reaction liquid was combined with 50 g of chloroform, and the organic phase was extracted. The organic phase was separated and dried over magnesium sulfate, and the magnesium sulfate was filtered out. The organic phase obtained was concentrated to afford a crude crystal, which was then washed with a 1:1 solution of diethyl ether and hexane to give N-methyl-2,4-dibromobutyric acid amide (21.4 g, 0.083 mol, mp: 54° C., yield: 69%).

The crystal was dissolved in THF (200 ml), and the solution was cooled with ice to not more than 10° C. To the cooled solution, 60% NaH in mineral oil (6.6 g, 0.166 mol, manufactured by JUNSEI CHEMICAL CO., LTD.) was added little by little over a period of about 15 minutes. After the completion of the addition, the mixture was heated to room temperature and stirred for 2 hours. After the reaction, the reaction liquid was concentrated to about ⅓ of the original weight, and the concentrate was poured into ice water (100 g) Subsequently, extraction was performed with 100 g of chloroform, and the chloroform phase was concentrated. The concentrate was purified by silica gel column chromatography to give N-methyl-2-bromo-4-butyrolactam (11.4 g, 0.064 mol, yield: 77%).

Synthetic Example 8

Production of N-methyl-2-mercapto-4-butyrolactam

70% Sodium hydrosulfide (6.1 g, 0.077 mmol, manufactured by JUNSEI CHEMICAL CO., LTD.) was dissolved in methyl alcohol (100 g, special grade, manufactured by JUNSEI CHEMICAL CO., LTD.) and purified water (100 g, water distilled and passed through an ion exchange filter). The resultant solution was cooled with ice to not more than 10° C. with stirring. To the cooled solution, a liquid mixture consisting of N-methyl-2-bromo-4-butyrolactam (11.4 g, 0.064 mol, yield: 77%) and methyl alcohol (50 g) was added dropwise over a period of about 30 minutes. After the completion of the dropwise addition, the mixture was stirred for 60 minutes, and the reaction liquid was concentrated to approximately ⅓ of the original volume under reduced pressure. To the concentrated liquid was added ethyl acetate (500 ml, special grade, manufactured by JUNSEI CHEMICAL CO., LTD.) followed by extraction. The aqueous phase obtained was subjected to re-extraction with ethyl acetate (500 ml). The organic phases thus extracted were combined and concentrated under reduced pressure. The concentrate was purified by silica gel column chromatography to give N-methyl-2-mercapto-4-butyrolactam (5.4 g, 0.041 mol, yield: 64%).

Synthetic Example 9

Production of 2-bromo-4-butyrolactam 2,4-Dibromobutyric acid amide (12.4 g, 0.076 mol, mp: 79° C., yield: 63%) was produced according to Synthetic Example 7, except that 2,4-dibromobutyric acid bromide obtained as described in Synthetic Example 6 was used and the 40% aqueous methylamine solution was replaced with ammonia water.

2-Bromo-4-butyrolactam (3.4 g, 0.021 mol, yield: 27%) was produced according to Synthetic Example 7.

Synthetic Example 10

Production of 2-mercapto-4-butyrolactam

2-Mercapto-4-butyrolactam (1.7 g, 0.014 mol, yield: 69%) was produced according to Synthetic Example 8, except that N-methyl-2-bromo-4-butyrolactam was replaced with 2-bromo-4-butyrolactam (3.4 g, 0.021 mol).

Synthetic Example 11

Production of N-ethyl-2-bromo-4-butyrolactam

N-ethyl-2,4-dibromobutyric acid amide (22.9 g, 0.084 mol, yield: 70%) was produced according to Synthetic Example 7, except that 2,4-dibromobutyric acid bromide obtained as described in Synthetic Example 6 was used and the 40% aqueous methylamine solution was replaced with 70% aqueous ethylamine solution.

N-ethyl-2-bromo-4-butyrolactam (11.5 g, 0.060 mol, yield: 71%) was produced according to Synthetic Example 7.

Synthetic Example 12

Production of N-ethyl-2-mercapto-4-butyrolactam

N-ethyl-2-mercapto-4-butyrolactam (6.0 g, 0.041 mol, yield: 69%) was produced according to Synthetic Example 8, except that N-methyl-2-bromo-4-butyrolactam was replaced with N-ethyl-2-bromo-4-butyrolactam (11.5 g, 0.060 mol).

Synthetic Example 13

Production of N-(2-methoxy)ethyl-2-bromo-4-butyrolactam

N-(2-methoxy)ethyl-2,4-dibromobutyric acid amide (22.5 g, 0.074 mol, yield: 62%) was produced according to Synthetic Example 7, except that 2,4-dibromobutyric acid bromide obtained as described in Synthetic Example 6 was used and the 40% aqueous methylamine solution was replaced with 50 wt % aqueous 2-methoxyethylamine solution.

N-(2-methoxy)ethyl-2-bromo-4-butyrolactam (10.9 g, 0.049 mol, yield: 66%) was produced according to Synthetic Example 7.

Synthetic Example 14

Production of N-(2-methoxy)ethyl-2-mercapto-4-butyrolactam

N-(2-methoxy)ethyl-2-mercapto-4-butyrolactam (4.9 g, 0.028 mol, yield: 57%) was produced according to Synthetic Example 8, except that N-(2-methoxy)ethyl-2-bromo-4-butyrolactam (10.9 g, 0.049 mol) was used.

Example A1

A permanent waving first liquid containing 2-mercapto-4-butyrolactone was prepared as described below. A permanent waving second liquid was prepared as described below. Hair was permanent waved with these liquids, and the waving efficiency was determined.
Preparation of Permanent Waving First Liquid 10 g of propylene glycol, 0.2 g of disodium edetate and 1 g of polyoxyethylene stearyl ether were added to 80 g of purified water (water distilled and passed through an ion exchange filter), and these were stirred to give a uniform mixture. With stirring, 22 mmol of 2-mercapto-4-butyrolactone was gradually added to the mixture using a Pasteur pipette. Stirring was performed for some time, and the liquid mixture was pH adjusted with monoethanolamine to achieve a desired pH (4.2, 6.0, 7.0 or 8.0). Stirring was performed sufficiently, and the pH was readjusted. To the pH adjusted liquid, purified water was added so that the amount of the liquid became 100 g, followed by stirring. A permanent waving first liquid was thus prepared. The liquid thus prepared had a pH shown in Table A1.

The agent contained 2-mercapto-4-butyrolactone in an amount of 2% by mass in terms of thioglycolic acid.
Preparation of Permanent Waving Second Liquid 5 g of sodium bromate and 95 g of purified water were mixed together to give a permanent waving second liquid.
Permanent Wave Processing The waving efficiency was evaluated by a spiral rod method as described in Fragrance Journal Extra Edition (1984, No. 5, P. 421).

Wet Chinese hair (approximately 20 cm long, 50 strands) was wound on a spiral curler (inner diameter: 13.5 mm). The permanent waving first liquid heated to 35° C. in an air-conditioned room (temperature: 35° C.) was uniformly applied to the hair with use of a pipette. Thereafter, the hair was lightly towel dried such that the first liquid would not drip.

The hair was allowed to stand at 35° C. for 20 minutes. Subsequently, the hair was given the bromate-based permanent waving second liquid, and was allowed to stand at 35° C. for 10 minutes. After the completion of the treatment with the second liquid, the hair was removed from the curler, rinsed with 35° C. water, and naturally dried in a suspended state with its one end being fixed with a clip or the like.

The permanent waved hair was measured and the waving efficiency was determined from the following equations. The results are shown in Table A1.

$L$ (average wave length)=$(l_1+l_2) \div (n_1+n_2)$ wherein:

$l_1$ and $l_2$: length between the leftmost and rightmost wave apexes except the first and last waves of the spiral curler;

$n_1$ and $n_2$: number of wave apexes on the right and left side of the spiral curler Waving efficiency (%): rod wave length÷L×100

Example A2

Permanent waving was performed in the same manner as in Example A1, except that 66 mmol of 2-mercapto-4-butyrolactone was used. The permanent waving first liquid contained 2-mercapto-4-butyrolactone in an amount of 6% by mass in terms of thioglycolic acid.

The results are shown in Table A1.

Example A3

Permanent waving was performed in the same manner as in Example A1, except that 2-mercapto-4-butyrolactone was replaced with 22 mmol of 2-mercapto-4-methyl-4-butyrolactone. The permanent waving first liquid contained 2-mercapto-4-methyl-4-butyrolactone in an amount of 2% by mass in terms of thioglycolic acid.

The results are shown in Table A1.

Example A4

Permanent waving was performed in the same manner as in Example A1, except that 2-mercapto-4-butyrolactone was replaced with 22 mmol of 2-mercapto-4-ethyl-4-butyrolactone. The permanent waving first liquid contained 2-mercapto-4-ethyl-4-butyrolactone in an amount of 2% by mass in terms of thioglycolic acid.

The results are shown in Table A1.

Example A5

Permanent waving was performed in the same manner as in Example A1, except that 2-mercapto-4-butyrolactone was replaced with 22 mmol of 2-mercapto-4-butyrothiolactone.

The permanent waving first liquid contained 2-mercapto-4-butyrothiolactone in an amount of 2% by mass in terms of thioglycolic acid.

The results are shown in Table A1.

Example A6

Permanent waving was performed in the same manner as in Example A1, except that 2-mercapto-4-butyrolactone was replaced with 22 mmol of 2-mercapto-6-hexanolactam. The permanent waving first liquid contained 2-mercapto-6-hexanolactam in an amount of 2% by mass in terms of thioglycolic acid.

The results are shown in Table A1.

Example A7

Permanent waving was performed in the same manner as in Example A1, except that 2-mercapto-4-butyrolactone was replaced with 22 mmol of 2-mercapto-4-butyrolactam. The permanent waving first liquid contained 2-mercapto-4-butyrolactam in an amount of 2% by mass in terms of thioglycolic acid.

The results are shown in Table A1.

Example A8

Permanent waving was performed in the same manner as in Example A1, except that 2-mercapto-4-butyrolactone was replaced with 22 mmol of N-methyl-2-mercapto-4-butyrolactam. The permanent waving first liquid contained N-methyl-2-mercapto-4-butyrolactam in an amount of 2% by mass in terms of thioglycolic acid.

The results are shown in Table A1.

Example A9

Permanent waving was performed in the same manner as in Example A1, except that 2-mercapto-4-butyrolactone was replaced with 22 mmol of N-ethyl-2-mercapto-4-butyrolactam. The permanent waving first liquid contained N-ethyl-2-mercapto-4-butyrolactam in an amount of 2% by mass in terms of thioglycolic acid.

The results are shown in Table A1.

Comparative Example A1

A permanent waving first liquid was prepared in the same manner as in Example A1, except that 2-mercapto-4-butyrolactone was replaced with 44 mmol of cysteine (manufactured by Showa Denko K.K.). The permanent waving first liquid contained cysteine in an amount of 4% by mass in terms of thioglycolic acid.

Permanent waving was performed and the waving efficiency was determined in the same manner as in Example A1, using the above-prepared permanent waving first liquid and the permanent waving second liquid used in Example A1.

The results are shown in Table A1.

Comparative Example A2

A permanent waving first liquid was prepared in the same manner as in Example A1, except that 2-mercapto-4-butyrolactone was replaced with 44 mmol of thioglycolic acid (manufactured by Tokyo Kasei Kogyo Co., Ltd., 4% by mass in terms of thioglycolic acid). Permanent waving was performed and the waving efficiency was determined in the same manner as in Example A1, using the above-prepared permanent waving first liquid and the permanent waving second liquid used in Example A1.

Figure 2:
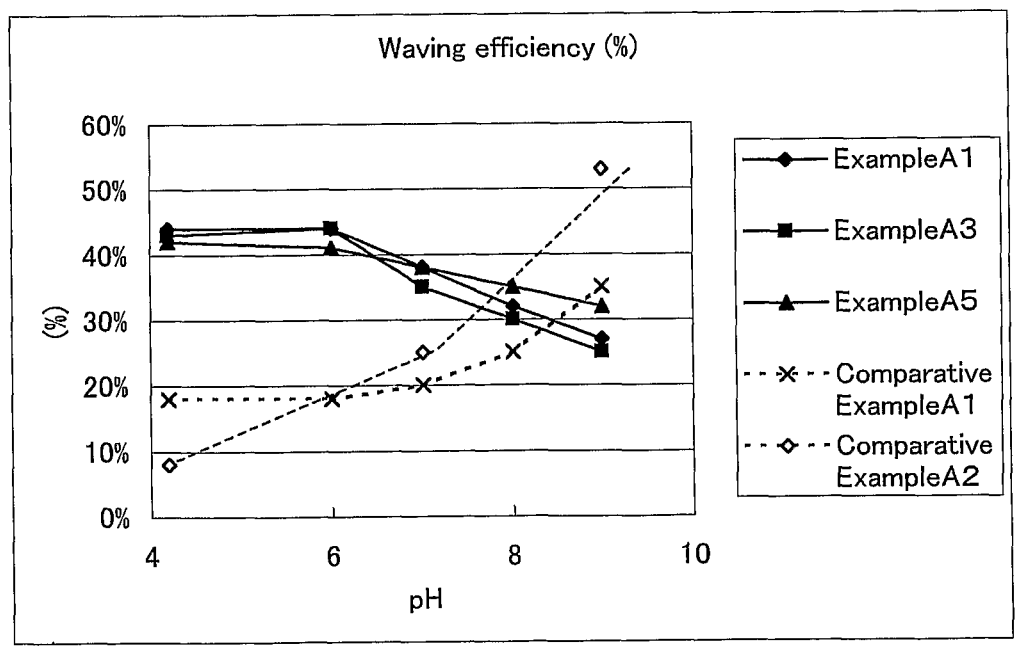
FIG. 2 is a graph showing changes of waving efficiency at various pH in Examples A1, A3 and A5 and Comparative Examples A1 and A2.

The results are shown in Table A1 and FIG. 2.

TABLE A1

| | Compound | Content in agent (%)* | Waving efficiency pH 4.2 | pH 6 | pH 7 | pH 8 | pH 9 |
|---|---|---|---|---|---|---|---|
| Ex. A1 | 2-Mercapto-4-butyrolactone | 2% | 44% | 44% | 38% | 32% | 27% |
| Ex. A2 | 2-Mercapto-4-butyrolactone | 6% | 51% | — | 43% | — | — |
| Ex. A3 | 2-Mercapto-4-methyl-4-butyrolactone | 2% | 43% | 44% | 35% | 30% | 25% |
| Ex. A4 | 2-Mercapto-4-methyl-4-butyrolactone | 2% | 37% | — | 32% | — | 24% |
| Ex. A5 | 2-Mercapto-4-butyrothiolactone | 2% | 42% | 41% | 38% | 35% | 32% |
| Ex. A6 | 2-Mercapto-6-hexanolactam | 2% | 35% | — | 30% | — | 22% |
| Ex. A7 | 2-Mercapto-4-butyrolactam | 2% | 41% | — | 38% | — | — |
| Ex. A8 | N-methyl-2-mercapto-4-butyrolactam | 2% | 40% | — | 38% | — | — |
| Ex. A9 | N-ethyl-2-mercapto-4-butyrolactam | 2% | 38% | — | 35% | — | — |
| Ex. A10 | N-(2-ethoxy)ethyl-2-mercapto-4-butyrolactam | 2% | 40% | — | 38% | — | — |
| Comp. Ex. A1 | Cysteine | 4% | 18% | 18% | 20% | 25% | 35% |
| Comp. Ex. A2 | Thioglycolic acid | 4% | 8% | — | 25% | — | 53% |

*In terms of thioglycolic acid (% by mass)

As indicated in FIG. 2, the conventional permanent waving agents (Comparative Examples A1 and A2) exhibited high waving efficiency when alkaline, but the waving efficiency worsened as the pH thereof was more acidic. By contrast, the hair processing agents according to the present invention showed high waving efficiency as the pH thereof was more acidic.

It is a known fact that hair is made up of a lipophilic cuticle layer, hydrophilic cortex and medulla, and is swollen with pH increase to enlarge the spaces between cuticles. Although the reason is unknown, Comparative Examples A1 and A2 indicate that highly hydrophilic cysteine and thioglycolic acid penetrate through the spaces between cuticles enlarged by swelling at a pH around 9, whilst the compounds of the invention having high lipophilicity are adsorbed to the lipophilic cuticle surface and penetrate in hair regardless of the pH. However, when the compounds of the invention are used at a pH around 9, ionization at the mercapto group inhibits penetration, and their lipophilicity limits the diffusion of the compounds into the cortex and medulla, resulting in lower performance.

That is, the hair processing agents containing the specific cyclic mercapto compounds proved to provide more stable waving efficiency in a neutral to acidic pH range than the general cysteine permanent waving agents.

Examples B1 to B3 and Comparative Examples B1 to B2

A permanent waving first liquid containing 2-mercapto-4-butyrolactone was prepared as described below. A permanent waving second liquid was prepared as described below. Hair was permanent waved with these liquids, and the waving efficiency was determined.

Preparation of Permanent Waving First Liquid

A 100-ml polyethylene vessel was charged with propylene glycol, polyoxyethylene (20) cetyl ether, sodium dihydrogen phosphate, disodium hydrogen phosphate, 2-mercapto-4-butyrolactone, cysteamine hydrochloride and 50 g of purified water (water distilled and passed through an ion exchange filter) according to Table B1. These were mixed sufficiently, and monoethanolamine and purified water were gradually added to adjust the pH to 6 and to obtain 100 g of a permanent waving first liquid. The agent thus obtained contained 2-mercapto-4-butyrolactone and cysteamine hydrochloride each in an amount of 2% by mass in terms of thioglycolic acid. (The agents of Comparative Examples B1, B3, B5, B7, B9, B11 and B12 contained no cysteamine hydrochloride, and the agents of Comparative Examples B2, B4, B6, B8, B10, B13 and B14 contained no cyclic mercapto compound of the formula (2).)

Preparation of Permanent Waving Second Liquid 5 g of sodium bromate and 95 g of purified water were mixed together to give a permanent waving second liquid.

Permanent Wave Processing

The waving efficiency was evaluated by a Kilby method as described in Fragrance Journal Extra Edition (1984, No. 5, P. 442).

Chinese hair (approximately 20 cm long) was fixed to a Kilby apparatus and was soaked in the permanent waving first liquid heated to 40° C. over a period of 20 minutes. Thereafter, the hair was taken from the first liquid and was lightly towel dried such that the first liquid would not drip. The hair was then given the bromate-based permanent waving second liquid, and was allowed to stand at 25° C. for 10 minutes. After the completion of the treatment with the second liquid, the hair was rinsed with running water and was removed from the Kilby apparatus, followed by drying. The dried hair was measured and the waving efficiency was determined from the following equation.

Waving efficiency (%)=100−[100×(B−A)]÷(C−A)

wherein:

A: Distance between the first and sixth rod of the Kilby apparatus (actual measurement value between the central points of the rods)
B: Length of six waves of curled hair
C: Length of straightened six waves of curled hair
The unit for A, B and C is cm.

The results are shown in Table B1.

TABLE B1

|  | Ex. B1 | Ex. B2 | Ex. B3 | Comp. Ex. B1 | Comp. Ex. B2 |
|---|---|---|---|---|---|
| Propylene glycol | 3.0 | 3.0 | 3.0 | 3.0 | 3.0 |
| Polyoxyethylene (20) cetyl ether | 2.0 | 2.0 | 2.0 | 2.0 | 2.0 |
| Sodium dihydrogen phosphate | 0.2 | 0.2 | 0.2 | 0.2 | 0.2 |
| Disodium hydrogen phosphate | 0.8 | 0.8 | 0.8 | 0.8 | 0.8 |
| 2-Mercapto-4-butyrolactone | 2.0 | 1.3 | 0.7 | 2.6 | 0.0 |
| Cysteamine hydrochloride | 0.4 | 0.9 | 1.3 | 0.0 | 1.7 |
| | Adjusted to pH 6 and 100 g with monoethanolamine and purified water | | | | |
| Waving efficiency (%) | 67 | 75 | 68 | 65 | 63 |

Examples B4 to B6 and Comparative Examples B3 to B4

Permanent waving was performed in the same manner as in Example B1, except that the permanent waving first liquid was prepared according to Table B2 and the pH was adjusted to 7.5. The results are shown in Table B2.

TABLE B2

|  | Ex. B4 | Ex. B5 | Ex. B6 | Comp. Ex. B3 | Comp. Ex. B4 |
|---|---|---|---|---|---|
| Propylene glycol | 3.0 | 3.0 | 3.0 | 3.0 | 3.0 |
| Polyoxyethylene (20) cetyl ether | 2.0 | 2.0 | 2.0 | 2.0 | 2.0 |
| Sodium dihydrogen phosphate | 0.2 | 0.2 | 0.2 | 0.2 | 0.2 |
| Disodium hydrogen phosphate | 0.8 | 0.8 | 0.8 | 0.8 | 0.8 |
| 2-Mercapto-4-butyrolactone | 2.0 | 1.3 | 0.7 | 2.6 | 0.0 |
| Cysteamine hydrochloride | 0.4 | 0.9 | 1.3 | 0.0 | 1.7 |
| | Adjusted to pH 7.5 and 100 g with monoethanolamine and purified water | | | | |
| Waving efficiency (%) | 62 | 73 | 69 | 55 | 68 |

Examples B7 to B9 and Comparative Examples B5 to B6

Permanent waving was performed in the same manner as in Example B1, except that the permanent waving first liquid was prepared according to Table B3, the contents of 2-mercapto-4-butyrolactone and cysteamine hydrochloride were each 6% by mass in terms of thioglycolic acid, and the pH was adjusted to 5. The results are shown in Table B3.

TABLE B3

|  | Ex. B7 | Ex. B8 | Ex. B9 | Comp. Ex. B5 | Comp. Ex. B6 |
|---|---|---|---|---|---|
| Propylene glycol | 3.0 | 3.0 | 3.0 | 3.0 | 3.0 |
| Polyoxyethylene (20) cetyl ether | 2.0 | 2.0 | 2.0 | 2.0 | 2.0 |
| Sodium dihydrogen phosphate | 0.2 | 0.2 | 0.2 | 0.2 | 0.2 |
| Disodium hydrogen phosphate | 0.8 | 0.8 | 0.8 | 0.8 | 0.8 |
| 2-Mercapto-4-butyrolactone | 5.9 | 3.9 | 2.0 | 7.8 | 0.0 |
| Cysteamine hydrochloride | 1.3 | 2.5 | 3.8 | 0.0 | 5.0 |
| | Adjusted to pH 5 and 100 g with monoethanolamine and purified water | | | | |
| Waving efficiency (%) | 85 | 87 | 81 | 83 | 75 |

Examples B10 to B12 and Comparative Examples B7 to B8

Permanent waving was performed in the same manner as in Example B1, except that the permanent waving first liquid was prepared according to Table B4, 2-mercapto-4-butyrolactone was replaced with 2-mercapto-4-methyl-4-butyrolactone, and the pH was adjusted to 5.5. The permanent waving first liquid contained 2-mercapto-4-methyl-4-butyrolactone and cysteamine hydrochloride each in an amount of 2% by mass in terms of thioglycolic acid. The results are shown in Table B4.

TABLE B4

|  | Ex. B10 | Ex. B11 | Ex. B12 | Comp. Ex. B7 | Comp. Ex. B8 |
|---|---|---|---|---|---|
| Propylene glycol | 3.0 | 3.0 | 3.0 | 3.0 | 3.0 |
| Polyoxyethylene (20) cetyl ether | 2.0 | 2.0 | 2.0 | 2.0 | 2.0 |
| Sodium dihydrogen phosphate | 0.2 | 0.2 | 0.2 | 0.2 | 0.2 |
| Disodium hydrogen phosphate | 0.8 | 0.8 | 0.8 | 0.8 | 0.8 |
| 2-Mercapto-4-methyl-4-butyrolactone | 2.2 | 1.5 | 0.7 | 2.9 | 0.0 |
| Cysteamine hydrochloride | 0.4 | 0.9 | 1.3 | 0.0 | 1.7 |
| | Adjusted to pH 5.5 and 100 g with monoethanolamine and purified water | | | | |
| Waving efficiency (%) | 66 | 72 | 66 | 65 | 60 |

Examples B13 to B15 and Comparative Examples B9 to B10

Permanent waving was performed in the same manner as in Example B1, except that the permanent waving first liquid was prepared according to Table B5, 2-mercapto-4-butyrolactone was replaced with 2-mercapto-4-butyrothiolactone, and the pH was adjusted to 5.5. The permanent waving first liquid contained 2-mercapto-4-butyrothiolactone and cysteamine hydrochloride each in an amount of 2% by mass in terms of thioglycolic acid. The results are shown in Table B5.

TABLE B5

|  | Ex. B13 | Ex. B14 | Ex. B15 | Comp. Ex. B9 | Comp. Ex. B10 |
|---|---|---|---|---|---|
| Propylene glycol | 3.0 | 3.0 | 3.0 | 3.0 | 3.0 |
| Polyoxyethylene (20) cetyl ether | 2.0 | 2.0 | 2.0 | 5.0 | 2.0 |
| Sodium dihydrogen phosphate | 0.2 | 0.2 | 0.2 | 0.2 | 0.2 |
| Disodium hydrogen phosphate | 0.8 | 0.8 | 0.8 | 0.8 | 0.8 |
| 2-Mercapto-4-butyrothiolactone | 2.4 | 1.6 | 0.8 | 3.2 | 0.0 |
| Cysteamine hydrochloride | 0.4 | 0.9 | 1.3 | 0.0 | 1.7 |
| | Adjusted to pH 5.5 and 100 g with monoethanolamine and purified water | | | | |
| Waving efficiency (%) | 63 | 67 | 65 | 52 | 63 |

Example B16 and Comparative Examples B11 to B14

Permanent waving was performed in the same manner as in Example B1, except that the permanent waving first liquid was prepared according to Table B6, 2-mercapto-4-butyrolactone was replaced with 2-mercapto-4-methyl-4-butyrolactone, cysteamine hydrochloride was replaced with ammonium thioglycolate, and the pH was adjusted to 7. The permanent waving first liquid contained 2-mercapto-4-methyl-4-butyrolactone and ammonium thioglycolate each in an amount of 2% by mass in terms of thioglycolic acid. The results are shown in Table B6.

TABLE B6

|  | Ex. B16 | Comp. Ex. B11 | Comp. Ex. B12 | Comp. Ex. B13 | Comp. Ex. B14 |
|---|---|---|---|---|---|
| Propylene glycol | 3.0 | 3.0 | 3.0 | 3.0 | 3.0 |
| Polyoxyethylene (20) cetyl ether | 2.0 | 2.0 | 2.0 | 5.0 | 5.0 |
| Sodium dihydrogen phosphate | 0.2 | 0.2 | 0.2 | 0.2 | 0.2 |
| Disodium hydrogen phosphate | 0.8 | 0.8 | 0.8 | 0.8 | 0.8 |
| 2-Mercapto-4-methyl-4-butyrolactone | 1.5 | 2.9 | 1.5 | 0.6 | 0.0 |
| Ammonium thioglycolate | 1.0 | 0.0 | 0.0 | 2.0 | 1.0 |
| | Adjusted to pH 7 and 100 g with monoethanolamine and purified water | | | | |
| Waving efficiency (%) | 57 | 60 | 45 | 33 | 25 |

Examples C1 to C15

85 g of purified water (water distilled and passed through an ion exchange filter) was weighed in a 300-ml glass tall beaker, and 3 g of propylene glycol, 0.2 g of monosodium dihydrogen phosphate and an amount shown in Table C1 of disodium hydrogen phosphate were added at room temperature, followed by stirring to achieve complete dissolution.

To the solution, a surfactant shown in Table C1 was added in an amount of 2 g, and stirring was performed to make the mixture substantially uniform. While vigorously stirring the solution with a homomixer, 2.6 g of 2-mercapto-4-butyrolactone synthesized in Synthetic Example 1 was gradually added. After the completion of the addition, stirring was performed with a homomixer for 5 minutes. Subsequently, purified water was added to achieve 100 g of liquid weight, and the mixture was stirred with a homomixer to give a test solution.

The test solution obtained was a colorless transparent liquid or a milky white to slightly yellow emulsion.

The test solution contained 2-mercapto-4-butyrolactone in an amount of 2% by mass in terms of thioglycolic acid.

Immediately after the test solution was prepared, it was placed in a 100-ml sample bottle with a lid, and the odor was checked. Improvement of odor was evaluated by the following criteria based on the odor immediately after preparation of a test solution of Comparative Example C1 described below. Thereafter, the lid of the sample bottle was closed, and the bottle was allowed to stand in a 40° C. thermostatic chamber.

After 10 days, the change of concentration of 2-mercapto-4-butyrolactone in the test solution was analyzed by high-performance liquid chromatography under the following conditions to determine the decomposition ratio of 2-mercapto-4-butyrolactone. Further, the change of color tone of the test solution between immediately after preparation and after 10 days was visually evaluated.

The results and pH of the test solutions are shown in Table C1.

Analytical Conditions for High-Performance Liquid Chromatography

Column: Shodex RSpak N,N-814 (column size: 8.0 mm in diameter×250 mm)
Eluent: 0.008 mM $KH_2PO_4$+0.1% $H_3PO_4$
Flow rate: 1.0 mL/min
Detector: UV (210 nm), RI
Column temperature: 40° C.
Injection volume: 20 μL
Odor Evaluation Criteria AA: Odor was drastically reduced as compared with the surfactant-free solution.
BB: Odor was reduced as compared with the surfactant-free solution.
CC: Odor was slightly improved as compared with the surfactant-free solution.
DD: Odor was equal to that of the surfactant-free solution.

Comparative Example C1

90 g of purified water was weighed in a 300-ml glass tall beaker, and 3 g of propylene glycol, 0.2 g of monosodium dihydrogen phosphate and 0.6 g of disodium hydrogen phosphate were added at room temperature, followed by stirring to achieve complete dissolution.

While stirring the solution with a homomixer, 2.6 g of 2-mercapto-4-butyrolactone synthesized in Synthetic Example 1 was gradually added. After the completion of the addition, stirring was performed with a homomixer for 5 minutes. Subsequently, purified water was added to achieve 100 g of liquid weight, and the mixture was stirred with a homomixer to give a test solution.

The test solution obtained was a colorless transparent solution.

The test solution contained 2-mercapto-4-butyrolactone in an amount of 2% by mass in terms of thioglycolic acid.

Immediately after the test solution was prepared, it was placed in a 100-ml sample bottle with a lid, and the odor was checked. The odor was obtained as a comparative sample (odor of surfactant-free solution) based on which the above odor evaluation was carried out. Thereafter, the lid of the sample bottle was closed, and the bottle was allowed to stand in a 40° C. thermostatic chamber.

After 10 days, the change of concentration of 2-mercapto-4-butyrolactone in the test solution was analyzed by high-performance liquid chromatography under the conditions described in Examples C1 to C15 to determine the decomposition ratio of 2-mercapto-4-butyrolactone. Further, the change of color tone of the test solution between immediately after preparation and after 10 days was visually evaluated.

The results and pH of the test solution are shown in Table C1.

TABLE C1

| unit: g | Example | | | | | | | |
|---|---|---|---|---|---|---|---|---|
| | C1 | C2 | C3 | C4 | C5 | C6 | C7 | C8 |
| 2-Mercapto-4-butyrolactone (MBL) | 2.6 | 2.6 | 2.6 | 2.6 | 2.6 | 2.6 | 2.6 | 2.6 |
| Propylene glycol | 3 | 3 | 3 | 3 | 3 | 3 | 3 | 3 |
| $NaH_2PO_4$ | 0.2 | 0.2 | 0.2 | 0.2 | 0.2 | 0.2 | 0.2 | 0.2 |
| $Na_2HPO_4$ | 0.8 | 0.8 | 0.4 | 0.5 | 0.4 | 0.6 | 0.6 | 0.6 |
| Cetyltrimethylammonium chloride | 2 | — | — | — | — | — | — | — |
| Acrylic acid/methacrylic acid copolymer | — | 2 | — | — | — | — | — | — |
| Sodium laurylsulfate | — | — | 2 | — | — | — | — | — |
| Sodium polyoxyethylene(2,5)laurylsulfate | — | — | — | 2 | — | — | — | — |
| Dioctylsodium sulfosuccinate | — | — | — | — | 2 | — | — | — |
| Polyoxyethylene/methylpolysiloxane copolymer | — | — | — | — | — | 2 | — | — |
| Hydrogenated lecithin | — | — | — | — | — | — | 2 | — |
| Surfactin | — | — | — | — | — | — | — | 2 |
| Water | Balance | Balance | Balance | Balance | Balance | Balance | Balance | Balance |
| pH | 5.8 | 5.5 | 6.1 | 6.4 | 6.2 | 6.0 | 6.0 | 5.9 |
| Odor evaluation | CC | AA | CC | CC | BB | BB | BB | AA |
| MBL decomposition ratio after 10 days (40° C.) | 30% | 10% | 29% | 28% | 10% | 8% | 15% | 13% |
| Color tone change after 10 days at 40° C. | Yellowed | Yellowed | Yellowed | Yellowed | No change | No change | No change | No change |

| unit: g | Example | | | | | | | Comp. Ex. |
|---|---|---|---|---|---|---|---|---|
| | C9 | C10 | C11 | C12 | C13 | C14 | C15 | C1 |
| 2-Mercapto-4-butyrolactone (MBL) | 2.6 | 2.6 | 2.6 | 2.6 | 2.6 | 2.6 | 2.6 | 2.6 |
| Propylene glycol | 3 | 3 | 3 | 3 | 3 | 3 | 3 | 3 |
| $NaH_2PO_4$ | 0.2 | 0.2 | 0.2 | 0.2 | 0.2 | 0.2 | 0.2 | 0.2 |
| $Na_2HPO_4$ | 0.6 | 0.6 | 0.6 | 0.6 | 0.6 | 0.6 | 0.6 | 0.6 |
| Polyoxyethylene (23) lauryl ether | 2 | — | — | — | — | — | — | — |
| Polyoxyethylene (20) cetyl ether | — | 2 | — | — | — | — | — | — |
| Polyoxyethylene (16) nonyl phenyl ether | — | — | 2 | — | — | — | — | — |
| Polyoxyethylene (20) sorbitan monooleate | — | — | — | 2 | — | — | — | — |
| Polyoxyethylene (60) hardened castor oil | — | — | — | — | 2 | — | — | — |
| Polyoxyethylene (5) oleic acid amide | — | — | — | — | — | 2 | — | — |
| Polyoxyethylene (40) sorbit tetraoleate | — | — | — | — | — | — | 2 | — |
| Water | Balance | Balance | Balance | Balance | Balance | Balance | Balance | Balance |
| pH | 5.9 | 6.0 | 6.0 | 5.9 | 6.0 | 6.0 | 5.9 | 6.0 |
| Odor evaluation | AA | AA | BB | BB | AA | AA | AA | DD |
| MBL decomposition ratio after 10 days (40° C.) | 10% | 8% | 9% | 7% | 7% | 8% | 9% | 43% |
| Color tone change after 10 days at 40° C. | No change | No change | No change | No change | Yellowed | Yellowed | Yellowed | Yellowed |

The results shown in Table C1 prove that the test solutions of Examples C1 to C15 can prevent decomposition of 2-mercapto-4-butyrolactone even after 10 days at 40° C., can avoid coloration, and can improve the odor as compared with the test solution of Comparative Example C1.

Examples C16 to C30

65 g of purified water was weighed in a 300-ml glass tall beaker, and 3 g of propylene glycol, 0.3 g of monosodium dihydrogen phosphate and an amount shown in Table C2 of disodium hydrogen phosphate were added at room temperature, followed by stirring to achieve complete dissolution.

To the solution, a surfactant shown in Table C2 was added in an amount of 4 g, and stirring was performed to make the mixture substantially uniform. While vigorously stirring the solution with a homomixer, 2.6 g of 2-mercapto-4-butyrolactone synthesized in Synthetic Example 1 was gradually added. After the completion of the addition, stirring was performed with a homomixer for 5 minutes. Subsequently, purified water was added to achieve 100 g of liquid weight, and the mixture was stirred with a homomixer to give a test solution.

The test solution contained 2-mercapto-4-butyrolactone in an amount of 12.7% by mass in terms of thioglycolic acid.

The test solution obtained was a colorless transparent liquid or a milky white to slightly yellow emulsion.

Immediately after the test solution was prepared, it was placed in a 100-ml sample bottle with a lid, and the odor was checked. Improvement of odor was evaluated by the aforesaid criteria based on the odor immediately after preparation of a test solution of Comparative Example C2 described below. Thereafter, the lid of the sample bottle was closed, and the bottle was allowed to stand in a 40° C. thermostatic chamber.

After 10 days, the change of concentration of 2-mercapto-4-butyrolactone in the test solution was analyzed by high-performance liquid chromatography under the conditions described in Examples C1 to C15 to determine the decomposition ratio of 2-mercapto-4-butyrolactone. Further, the change of color tone of the test solution between immediately after preparation and after 10 days was visually evaluated.

The results and pH of the test solutions are shown in Table C2.

Comparative Example C2

70 g of purified water was weighed in a 300-ml glass tall beaker, and 3 g of propylene glycol, 0.3 g of monosodium dihydrogen phosphate and 0.8 g of disodium hydrogen phosphate were added at room temperature, followed by stirring to achieve complete dissolution.

While stirring the solution with a homomixer, 15 g of 2-mercapto-4-butyrolactone synthesized in Synthetic Example 1 was gradually added. After the completion of the addition, stirring was performed with a homomixer for 5 minutes. Subsequently, purified water was added to achieve 100 g of liquid weight, and the mixture was stirred with a homomixer to give a test solution.

The test solution obtained was a colorless liquid, but a slight amount of oily substances remained undissolved.

The test solution contained 2-mercapto-4-butyrolactone in an amount of 12.7% by mass in terms of thioglycolic acid.

Immediately after the test solution was prepared, it was placed in a 100-ml sample bottle with a lid, and the odor was checked. The odor was obtained as a comparative sample (odor of surfactant-free solution) based on which the above odor evaluation was carried out. Thereafter, the lid of the sample bottle was closed, and the bottle was allowed to stand in a 40° C. thermostatic chamber.

After 10 days, the change of concentration of 2-mercapto-4-butyrolactone in the test solution was analyzed by high-performance liquid chromatography under the conditions described in Examples C1 to C15 to determine the decomposition ratio of 2-mercapto-4-butyrolactone. Further, the change of color tone of the test solution between immediately after preparation and after 10 days was visually

TABLE C2

| unit: g | Example | | | | | | | |
|---|---|---|---|---|---|---|---|---|
| | C16 | C17 | C18 | C19 | C20 | C21 | C22 | C23 |
| 2-Mercapto-4-butyrolactone (MBL) | 15 | 15 | 15 | 15 | 15 | 15 | 15 | 15 |
| Propylene glycol | 3 | 3 | 3 | 3 | 3 | 3 | 3 | 3 |
| $NaH_2PO_4$ | 0.3 | 0.3 | 0.3 | 0.3 | 0.3 | 0.3 | 0.3 | 0.3 |
| $Na_2HPO_4$ | 0.9 | 0.9 | 0.4 | 0.4 | 0.4 | 0.8 | 0.8 | 0.8 |
| Cetyltrimethylammonium chloride | 4 | — | — | — | — | — | — | — |
| Acrylic acid/methacrylic acid copolymer | — | 4 | — | — | — | — | — | — |
| Sodium laurylsulfate | — | — | 4 | — | — | — | — | — |
| Sodium polyoxyethylene(2,5)laurylsulfate | — | — | — | 4 | — | — | — | — |
| Dioctylsodium sulfosuccinate | — | — | — | — | 4 | — | — | — |
| Polyoxyethylene/methylpolysiloxane copolymer | — | — | — | — | — | 4 | — | — |
| Hydrogenated lecithin | — | — | — | — | — | — | 4 | — |
| Surfactin | — | — | — | — | — | — | — | 4 |
| Water | Balance | Balance | Balance | Balance | Balance | Balance | Balance | Balance |
| pH | 6.1 | 6.1 | 5.9 | 5.9 | 5.9 | 6.0 | 6.1 | 6.0 |
| Odor evaluation | CC | BB | CC | CC | BB | BB | BB | BB |
| MBL decomposition ratio after 10 days (40° C.) | 22% | 2% | 21% | 19% | 3% | 5% | 6% | 8% |
| Color tone change after 10 days at 40° C. | Yellowed | No change | Yellowed | Yellowed | No change | No change | No change | No change |

| unit: g | Example | | | | | | | Comp. Ex. |
|---|---|---|---|---|---|---|---|---|
| | C24 | C25 | C26 | C27 | C28 | C29 | C30 | C2 |
| 2-Mercapto-4-butyrolactone (MBL) | 15 | 15 | 15 | 15 | 15 | 15 | 15 | 15 |
| Propylene glycol | 3 | 3 | 3 | 3 | 3 | 3 | 3 | 3 |
| $NaH_2PO_4$ | 0.3 | 0.3 | 0.3 | 0.3 | 0.3 | 0.3 | 0.3 | 0.3 |
| $Na_2HPO_4$ | 0.8 | 0.8 | 0.8 | 0.8 | 0.8 | 0.8 | 0.8 | 0.8 |
| Polyoxyethylene (23) lauryl ether | 4 | — | — | — | — | — | — | — |
| Polyoxyethylene (20) cetyl ether | — | 4 | — | — | — | — | — | — |
| Polyoxyethylene (16) nonyl phenyl ether | — | — | 4 | — | — | — | — | — |
| Polyoxyethylene (20) sorbitan monooleate | — | — | — | 4 | — | — | — | — |
| Polyoxyethylene (60) hardened castor oil | — | — | — | — | 4 | — | — | — |
| Polyoxyethylene (5) oleic acid amide | — | — | — | — | — | 4 | — | — |
| Polyoxyethylene (40) sorbit tetraoleate | — | — | — | — | — | — | 4 | — |
| Water | Balance | Balance | Balance | Balance | Balance | Balance | Balance | Balance |
| pH | 5.9 | 6.0 | 6.0 | 6.0 | 5.9 | 6.0 | 6.0 | 5.9 |

TABLE C2-continued

| | | | | | | | | |
|---|---|---|---|---|---|---|---|---|
| Odor evaluation | AA | BB | BB | AA | AA | BB | AA | DD |
| MBL decomposition ratio after 10 days (40° C.) | 3% | 3% | 5% | 4% | 5% | 5% | 7% | 34% |
| Color tone change after 10 days at 40° C. | No change | No change | No change | No change | No change | No change | No change | No change |

The results shown in Table C2 prove that even when 2-mercapto-4-butyrolactone is added in an increased amount, the test solutions of Examples C16 to C30 can prevent decomposition of 2-mercapto-4-butyrolactone even after 10 days at 40° C., can avoid coloration, and can improve the odor as compared with the test solution of Comparative Example C2.

Examples C31 to C34

The test solutions of Examples C1, C6, C9 and C10 that had been tested for decomposition ratio were used as a permanent waving first liquid. A permanent waving second liquid was prepared as described below. Hair was permanent waved with these first and second liquids by the following method to examine the influence of storage on the permanent waving performance.

Permanent Waving First Liquid

The test solutions of Examples C1, C6, C9 and C10 shown in Table C1 that had been tested for decomposition ratio were used as a permanent waving first liquid.

Preparation of Permanent Waving Second Liquid 5 g of sodium bromate and 95 g of purified water were mixed together to give a permanent waving second liquid.

Permanent Wave Processing

The waving efficiency was evaluated by a Kilby method as described in Fragrance Journal Extra Edition (1984, No. 5, P. 442). (For details, see the description given above.)

The waving efficiency evaluated above was obtained as X2 (for the test solutions of Examples C1, C6, C9 and C10 that had been tested for decomposition ratio). Separately, the waving efficiency was determined in the same manner as described above, except that the test solutions of Examples C1, C6, C9 and C10 were used immediately after preparation, and the results were obtained as X1.

The lowering rate of waving efficiency was calculated from X1 and X2 by the following equation. The results are shown in Table C3.

Lowering rate of waving efficiency (%)=[($X1-X2$)/$X1$]×100

Comparative Example C3

Hair was permanent waved and the waving efficiency X2 was determined in the same manner as in Examples C31 to C34, except that the test solution of Comparative Example C1 that had been tested for decomposition ratio was used as a permanent waving first liquid. The waving efficiency X1 was determined as described above, except that the test solution of Comparative Example C1 was used immediately after preparation.

The lowering rate of waving efficiency was calculated from X1 and X2 by the equation described in Examples C31 to C34. The results are shown in Table C3.

TABLE C3

Test of lowering rate of waving efficiency by Kilby method after storage at 40° C. for 10 days

| | Type of surfactant | Test solution composition | Lowering rate of waving efficiency |
|---|---|---|---|
| Ex. C31 | Cetyltrimethylammonium chloride | Ex. C1 | 19% |
| Ex. C32 | Polyoxyethylene/methylpolysiloxane copolymer | Ex. C6 | 5% |
| Ex. C33 | Polyoxyethylene (23) lauryl ether | Ex. C9 | 6% |
| Ex. C34 | Polyoxyethylene (20) cetyl ether | Ex. C10 | 4% |
| Comp. Ex. C3 | None | Comp. Ex. C1 | 38% |

The results shown in Table C3 prove that the test solutions of Examples C31 to C34 can prevent over-time decomposition of 2-mercapto-4-butyrolactone and therefore the lowering rate of hair waving efficiency is low as compared with the test solution immediately after preparation. Accordingly, these test solutions of Examples are valid as permanent waving agent for a longer term than the test solution of Comparative Example C3.

Examples D1 to D169

Permanent Waving First Agent

A permanent waving first agent was prepared according to a composition shown in Table D1. To the agent, perfumes described in Tables D2 to D5 were added each in an amount of 0.3% to give test solutions. 50 ml of each of the solutions was weighed in a wide-mouth bottle, and an organoleptic test was carried out by three panelists in a blind test system in which the panelists were not informed of the perfumes added. The organoleptic test graded the test solutions into 5 grades.

TABLE D1

Composition of permanent waving first agent for perfume testing

| | |
|---|---|
| 2-Mercapto-4-butyrolactone | 2.6% by mass |
| Polyethylene glycol (20) cetyl ether | 2.0% by mass |
| Propylene glycol | 3.0% by mass |
| Monosodium dihydrogen phosphate | 1.0% by mass |
| Disodium hydrogen phosphate | 1.5% by mass |
| Purified water | 89.6% by mass |

Evaluation Criteria
5: Very excellent
4: Excellent
3: satisfactory as product
2: Rather bad
1: Bad The evaluations by the three panelists were averaged and indicated as integer according to the following rules:
5: Average in the range of 5 to not less than 4.5
4: Average in the range of less than 4.5 to not less than 3.5
3: Average in the range of less than 3.5 to not less than 2.5

2: Average in the range of less than 2.5 to not less than 1.5
1: Average less than 1.5
The results are shown in Tables D2 to D5.

TABLE D2

| Ex. D No. | Perfume added | Evaluation |
|---|---|---|
| Ex. D1 | Acetyloctahydrotetramethylnaphthalene | 4 |
| Ex. D2 | Acetyldiisoamylene | 5 |
| Ex. D3 | Acetylhexamethylindane | 4 |
| Ex. D4 | Acetylhexamethyltetralin | 4 |
| Ex. D5 | Acetophenone | 3 |
| Ex. D6 | Anisyl formate | 4 |
| Ex. D7 | Anise alcohol | 5 |
| Ex. D8 | Anise aldehyde | 3 |
| Ex. D9 | Anethol | 4 |
| Ex. D10 | Isopropylcyclohexyl ethanol | 4 |
| Ex. D11 | Isopropylphenylacetaldehyde | 3 |
| Ex. D12 | Isohexenylcyclohexenecarboxaldehyde | 4 |
| Ex. D13 | Isomenthone | 4 |
| Ex. D14 | Phenoxyethyl isobutyrate | 4 |
| Ex. D15 | Undecanal | 4 |
| Ex. D16 | Undecalactone | 5 |
| Ex. D17 | Undecenal | 4 |
| Ex. D18 | Estragole | 4 |
| Ex. D19 | Ethyl trimethyl cyclopentene yl butene ol | 4 |
| Ex. D20 | Ethyl maltol | 5 |
| Ex. D21 | Ethoxyvinyltetramethylcyclohexanone | 4 |
| Ex. D22 | Octanol | 3 |
| Ex. D23 | Methyl octine carboxylate | 4 |
| Ex. D24 | Orange oil | 5 |
| Ex. D25 | Carvone | 4 |
| Ex. D26 | Camphor | 5 |
| Ex. D27 | Coumarin | 3 |
| Ex. D28 | Cuminaldehyde | 4 |
| Ex. D29 | Grape fruit oil | 4 |
| Ex. D30 | Cresol | 3 |
| Ex. D31 | Geraniol | 5 |
| Ex. D32 | Geranyl tiglate | 4 |
| Ex. D33 | Geranyl nitrile | 5 |
| Ex. D34 | Geranyl trityl | 4 |
| Ex. D35 | Cymene | 4 |
| Ex. D36 | Salicyclic acid | 3 |
| Ex. D37 | Phenyl ethyl salicylate | 4 |
| Ex. D38 | Sandalwood oil | 4 |
| Ex. D39 | Santalol | 4 |
| Ex. D40 | Cyclamen aldehyde | 4 |
| Ex. D41 | Cyclohexadecenolide | 4 |
| Ex. D42 | Allyl cyclohexylpropionate | 4 |
| Ex. D43 | Cyclohexylmethylpentanone | 4 |
| Ex. D44 | Cyclopentadecanolide | 5 |
| Ex. D45 | Cyclopentadecenone | 4 |
| Ex. D46 | Citral | 5 |
| Ex. D47 | Citronellal | 5 |
| Ex. D48 | Citronellyl formate | 4 |
| Ex. D49 | Citronellol | 4 |
| Ex. D50 | Dinitrodimethylbutylbenzene | 4 |

TABLE D3

| Ex. D No. | Perfume added | Evaluation |
|---|---|---|
| Ex. D51 | Cineol | 4 |
| Ex. D52 | Methyl dihydrojasmonate | 5 |
| Ex. D53 | Dihydromyrcenol | 5 |
| Ex. D54 | Diphenyl oxide | 4 |
| Ex. D55 | Diphenylmethane | 4 |
| Ex. D56 | Dimethyloctadienal | 4 |
| Ex. D57 | Dimethyloctanol | 5 |
| Ex. D58 | Dimethyloctenol | 5 |
| Ex. D59 | Dimethyltetrahydrobenzaldehyde | 4 |
| Ex. D60 | Dimethylheptenal | 4 |
| Ex. D61 | Dimethylbenzylcarbinol | 4 |
| Ex. D62 | Dimethoxybenzaldehyde | 3 |
| Ex. D63 | Jasmone | 4 |
| Ex. D64 | Sugar lactone | 4 |
| Ex. D65 | Cinnamic alcohol | 5 |
| Ex. D66 | Spearmint oil | 5 |

TABLE D3-continued

| Ex. D No. | Perfume added | Evaluation |
|---|---|---|
| Ex. D67 | Geranium oil | 4 |
| Ex. D68 | Damascene | 5 |
| Ex. D69 | Tansy oil | 5 |
| Ex. D70 | Decanal | 4 |
| Ex. D71 | γ-Decalactone | 5 |
| Ex. D72 | Terpineol | 4 |
| Ex. D73 | Terpinene | 4 |
| Ex. D74 | Triplal | 5 |
| Ex. D75 | Trimethylundecadienal | 5 |
| Ex. D76 | Trimethylundecanol | 4 |
| Ex. D77 | Trimethylcrotonylcyclohexane | 4 |
| Ex. D78 | Ethyl trimethylcyclohexanecarboxylate | 4 |
| Ex. D79 | Trimethylcyclohexanemethyl formate | 4 |
| Ex. D80 | Trimethylhexenal | 5 |
| Ex. D81 | Nerol | 5 |
| Ex. D82 | Nerolidol | 5 |
| Ex. D83 | Nonanol | 4 |
| Ex. D84 | γ-Nonalactone | 5 |
| Ex. D85 | Basil oil | 5 |
| Ex. D86 | Paramethoxyphenethyl alcohol | 3 |
| Ex. D87 | Hydroxycitronellal | 4 |
| Ex. D88 | Hydroxymethylpentylcyclohexenecarboxaldehyde | 4 |
| Ex. D89 | Pinene | 5 |
| Ex. D90 | Phenylacetaldehyde | 4 |
| Ex. D91 | Phenyl ethyl alcohol | 5 |
| Ex. D92 | Phenyl ethyl formate | 4 |
| Ex. D93 | Phenyl propanal | 5 |
| Ex. D94 | Phenyl formate | 4 |
| Ex. D95 | Fenchyl alcohol | 5 |
| Ex. D96 | Butylcyclohexanol | 4 |
| Ex. D97 | Butyl phenyl propanal | 4 |
| Ex. D98 | Butylmethylhydrocinnamicaldehyde | 4 |
| Ex. D99 | Propionic acid ester | 3 |
| Ex. D100 | Hexalactone | 4 |

TABLE D4

| Ex. D No. | Perfume added | Evaluation |
|---|---|---|
| Ex. D101 | Allyl hexanoate | 4 |
| Ex. D102 | Hexylcinnamic aldehyde | 4 |
| Ex. D103 | Hexyl tiglate | 4 |
| Ex. D104 | Hexenal | 5 |
| Ex. D105 | Hexenyl | 4 |
| Ex. D106 | Cis-3-hexenol | 5 |
| Ex. D107 | Peppermint oil | 5 |
| Ex. D108 | Bergamot oil | 5 |
| Ex. D109 | Benzyl alcohol | 3 |
| Ex. D110 | Benzyl ether | 4 |
| Ex. D111 | Benzyl formate | 4 |
| Ex. D112 | Benzaldehyde | 5 |
| Ex. D113 | Borneol | 5 |
| Ex. D114 | Mint oil | 4 |
| Ex. D115 | Methanoindane carboxaldehyde | 4 |
| Ex. D116 | Methylionone | 5 |
| Ex. D117 | Methylisoeugenol | 4 |
| Ex. D118 | Methylisopropylphenylpropionealdehyde | 4 |
| Ex. D119 | Methylundecanal | 4 |
| Ex. D120 | Methylcinnamic aldehyde | 5 |
| Ex. D121 | Methyltrimethylcyclohexenylbutenal | 4 |
| Ex. D122 | Methyltrimethylcyclopenteneylbutenol | 4 |
| Ex. D123 | Methyltrimethylcyclopenteneylpentanol | 4 |
| Ex. D124 | Methylmethoxyphenylpropanal | 4 |
| Ex. D125 | Methylionone | 4 |
| Ex. D126 | Methyleneoxybenzaldehyde | 4 |
| Ex. D127 | Methoxycitronellal | 5 |
| Ex. D128 | Methoxyphenethyl alcohol | 4 |
| Ex. D129 | Menthanol | 5 |
| Ex. D130 | Menthol | 5 |
| Ex. D131 | Menthone | 4 |
| Ex. D132 | Eucalyptus oil | 4 |
| Ex. D133 | Eucalypt oil | 4 |
| Ex. D134 | Ionone | 4 |
| Ex. D135 | Lime oil | 5 |
| Ex. D136 | Raspberry ketone | 5 |

TABLE D4-continued

| Ex. D No. | Perfume added | Evaluation |
|---|---|---|
| Ex. D137 | Lavandin oil | 4 |
| Ex. D138 | Lavender oil | 4 |
| Ex. D139 | Linalool | 5 |
| Ex. D140 | Linalyl formate | 4 |
| Ex. D141 | Linalool oxide | 5 |
| Ex. D142 | Limonene | 5 |
| Ex. D143 | Lemon oil | 5 |
| Ex. D144 | Rose oxide | 4 |
| Ex. D145 | Rosephenone | 5 |
| Ex. D146 | Rose oil | 4 |
| Ex. D147 | Phenyl ethyl benzoate | 4 |
| Ex. D148 | Isoamyl acetate | 4 |
| Ex. D149 | Isobornyl acetate | 5 |
| Ex. D150 | Acetic acid ester | 4 |

TABLE D5

| Ex. D No. | Perfume added | Evaluation |
|---|---|---|
| Ex. D151 | Ethyl acetate | 4 |
| Ex. D152 | Geranyl acetate | 4 |
| Ex. D153 | Dimethyloctadieneyl acetate | 4 |
| Ex. D154 | Dimethyl phenyl ethyl carbinyl acetate | 5 |
| Ex. D155 | Dimethyl benzyl carbinyl acetate | 5 |
| Ex. D156 | Cedrenyl acetate | 4 |
| Ex. D157 | Butylcyclohexyl acetate | 5 |
| Ex. D158 | Vetiveryl acetate | 4 |
| Ex. D159 | Heliotropyl acetate | 4 |
| Ex. D160 | Benzyl acetate | 4 |
| Ex. D161 | Menthenyl acetate | 4 |
| Ex. D162 | 2-Methyl-4-(2,2,3-trimethyl-3-cyclopentene-1-yl)-2-butene-1-ol | 5 |
| Ex. D163 | 3-Methyl-5-(2,2,3-trimethyl-3-cyclopentene-1-yl)-pentane-2-ol | 5 |
| Ex. D164 | 2-Ethyl-4-(2,2,3-trimethyl-3-cyclopentene-1-yl)-2-butene-1-ol | 5 |
| Ex. D165 | 4-(1-Ethoxyvinyl)-3,3,5,5-tetramethylcyclohexanone | 5 |
| Ex. D166 | Cis-p-menthane-7-ol | 5 |
| Ex. D167 | α,3,3,-Trimethylcyclohexanemethyl formate | 5 |
| Ex. D168 | Ethyl 2,2,6-trimethylcyclohexanecarboxylate | 5 |
| Ex. D169 | 2,6,6-Trimethyl-1-crotonylcyclohexane | 5 |

[Examples D201 to D276 and Comparative Example D1]

Permanent waving first agent (curling agent) and second agent having compositions shown in Tables D6 and D7, respectively, were prepared, and the following evaluation was performed using the perfumes described in Table D8. Comparative Example D1 employed a perfume-free agent. As the reducing agent, 2-mercapto-4-butyrolactone was used similarly in Example D1.

Evaluations (1) to (5)

The first liquids prepared were subjected to an organoleptic test by five perfumers on a scale on which 3 was perfection. The evaluations by the five perfumers were averaged and evaluated by the following criteria (Evaluation (1)).

A: 2.5≤(score)
B: 1.75≤(score)<2.5
C: 0.75≤(score)<1.75
D: (score)<0.75

Subsequently, 1 g of the first liquid was applied to 1 g of hair entirely, and the hair was allowed to stand at room temperature for 15 minutes. The odor during the standing was similarly evaluated (Evaluation (2)).

Further, the hair was rinsed with water and was entirely wetted with 1 g of the second liquid. The hair was allowed to stand at room temperature for 10 minutes. The second liquid was rinsed away with water, and the hair was lightly towel dried. The odor on the hair was evaluated in a similar manner (Evaluation (3)).

The odor was evaluated after the lapse of 30 minutes (Evaluation (4)) and after the lapse of 90 minutes (Evaluation (5)).

The results are shown in Table D8.

TABLE D6

| Composition of first liquid | |
|---|---|
| Material | (% by mass) |
| Monosodium dihydrogen phosphate | 0.20 |
| Disodium hydrogen phosphate | 0.80 |
| 3-Methyl-1,3-butanediol | 2.00 |
| POE (60) hydrogenated castor oil | 2.00 |
| Perfume | 0.20 |
| 4-Mercapto-4-butyrolactone | 2.50 |
| Purified water | Up to 100 |

TABLE D7

| Composition of second liquid | |
|---|---|
| Material | (% by mass) |
| Hydroxyethane disulfonic acid 4Na (30%) | 0.30 |
| Monosodium dihydrogen phosphate | 0.20 |
| Sodium bromate | 6.50 |
| POE (20) cetyl ether | 0.50 |
| Purified water (secondary addition water) | Up to 100 |

The liquids were pH adjusted to 6.0-6.5 with sodium hydrogen phosphate.

TABLE D8

| | Perfume name | Evaluation of single perfume | | | | |
|---|---|---|---|---|---|---|
| | | Evaluation (1) | Evaluation (2) | Evaluation (3) | Evaluation (4) | Evaluation (5) |
| Ex. D201 | 2,6,10-Trimethyl-9-undecenal | A | B | B | B | B |
| D202 | n-Decanal | A | A | A | A | A |
| D203 | n-Octanal | A | A | A | A | A |
| D204 | Allyl amylglycolate | A | A | A | A | B |
| D205 | Allyl heptanoate | A | A | B | C | C |
| D206 | alpha-Amylcinnamaldehyde | B | B | B | B | B |
| D207 | Anethol | B | B | B | B | B |
| D208 | p-Methoxybenzaldehyde | A | A | A | A | A |
| D209 | 6,7-Dihydro-1,1,2,3,3-pentamethyl- | A | A | A | B | B |
| D210 | Cinnamic alcohol | A | B | B | B | B |
| D211 | cis-3-Hexen-1-yl acetate | A | A | B | C | C |
| D212 | cis-6-Nonenol | B | A | B | B | B |
| D213 | Citral | A | A | B | B | C |

TABLE D8-continued

Evaluation of single perfume

| | Perfume name | Evaluation (1) | Evaluation (2) | Evaluation (3) | Evaluation (4) | Evaluation (5) |
|---|---|---|---|---|---|---|
| D214 | Citral diethyl acetal | A | A | B | B | B |
| D215 | Citronellal | A | A | A | A | B |
| D216 | Citronellol | B | B | B | B | B |
| D217 | Citronellyl nitrile | A | A | B | B | C |
| D218 | Tricyclodecenyl acetate | A | A | A | A | A |
| D219 | Tricyclodecenyl propionate | A | A | A | A | A |
| D220 | Acetic Acid(cyclohexyloxy)-2-propenylester | B | B | B | B | B |
| D221 | delta-Damascone | B | B | B | B | B |
| D222 | Dihydrojasmone | A | A | A | B | B |
| D223 | Diphenyl ether | A | B | A | B | B |
| D224 | Acetaldehyde ethyl phenylethyl acetal | A | A | A | A | B |
| D225 | Acetaldehyde ethyl linalyl acetal | A | B | B | B | B |
| D226 | Estragole | A | A | B | B | C |
| D227 | Ethyl 2-methylbutyrate | A | B | B | B | B |
| D228 | Ethyl maltol | A | A | A | B | B |
| D229 | Ethyl butyrate | A | B | B | B | C |
| D230 | Ethyl dehydrocyclogeranate | A | A | A | A | A |
| D231 | Ethyl vanillin | B | A | A | B | B |
| D232 | Eugenol | A | A | B | C | C |
| D233 | p-Ethyl alpha,alpha-dimethyl dihydrocinnamaldehyde | A | B | A | B | B |
| D234 | 2,4,6-Trimethyl-4-phenyl-1,3-dioxane | B | B | B | B | B |
| D235 | Ethyl octahydro-4,7-methano[3aH]-3a- | A | A | A | A | B |
| D236 | 2-Ethyl-4-hydroxy-5-methyl-3-(2H)furanone | A | A | A | A | A |
| D237 | alpha-Methylphenylacetaldehyde | A | B | A | B | B |
| D238 | Indole | A | A | A | B | B |
| D239 | alpha-Ionone | A | A | B | B | B |
| D240 | Isoamyl salicylate | A | A | B | C | C |
| D241 | Isobutyl quinoline | A | A | A | A | A |
| D242 | alpha-Isomethylionone | A | B | A | A | A |
| D243 | Phenylacetaldehyde | A | B | A | A | A |
| D244 | 6-(3-Pentenyl)tetrahydro[2H]pyran-2-one | A | A | B | B | B |
| D245 | 2-(2,4-Dimethyl-3-cyclohexyl)-5-methyl-5-(1-methylpropyl)-1,3-dioxane | B | B | B | A | A |
| D246 | cis-3-Hexenol | A | A | A | A | B |
| D247 | Geranyl nitrile | A | A | A | A | B |
| D248 | cis-3-Hexenyl methyl carbonate | A | A | B | B | C |
| D249 | Tetrahydro linalool | B | B | B | B | B |
| D250 | Linalool | B | B | A | B | A |
| D251 | cis-3-dodecenal | B | B | B | B | B |
| D252 | Ethyl 2-methylpentanoate | A | B | A | A | A |
| D253 | 2,6-Dimethyl-5-heptenal | A | A | A | A | B |
| D254 | Methyl anthranilate | A | B | A | A | A |
| D255 | Methyl benzoate | A | A | B | B | B |
| D256 | Methyl salicylate | A | A | A | B | B |
| D257 | 3-Methylcyclopentadecanolide | C | B | A | B | B |
| D258 | Nerol | A | B | B | B | C |
| D259 | p-Cresol | B | A | A | A | A |
| D260 | p-Methylanisole | A | A | A | B | B |
| D261 | Phenyl aceticacid | B | A | A | A | A |
| D262 | beta-Phenylethyl alcohol | A | B | B | B | A |
| D263 | Phenylethyl formate | A | A | B | B | B |
| D264 | Phenylethyl isoamyl ether | A | A | A | A | B |
| D265 | 4-(p-Hydroxyphenyl)-2-butanone | B | B | A | B | B |
| D266 | Tetrahydro-4-methyl-2-(2-methyl-1-propenyl)-(2H)pyran | A | A | B | C | C |
| D267 | 5-Methyl-3-heptanone oxime | A | A | A | A | B |
| D268 | trans-2-Hexen-1-ol | A | A | B | C | C |
| D269 | 2-Tridecenonitrile | A | A | A | A | A |
| D270 | 3-Cyclohexene-1-carboxaldehyde, dimethyl | A | B | B | B | B |
| D271 | Vanillin | A | A | A | B | C |
| D272 | o-t-Butylcyclohexyl acetate | A | A | B | C | C |
| D273 | Acetylcedrene | A | A | B | B | C |
| D274 | Vetiveryl acetate | B | B | B | B | B |
| D275 | Phenylacetaldehyde dimethyl acetal | A | A | B | B | B |
| D276 | Rhodinol | B | B | B | B | B |
| Comp. Ex. D1 | No perfume added | D | D | D | D | D |

Examples D277 to D278

A hair processing agent (curling first liquid) was prepared in the same manner as in Examples D201 to D276, except that perfume mixtures A (Example D277) and B (Example D278) having compositions shown in Tables D9 and D10, respectively, were used as perfumes. The evaluations were carried out similarly. The results are shown in Table D11.

TABLE D9

| Perfume mixture A | (% by mass) |
|---|---|
| Hexahydro-4,6,6,7,8,8-hexamethylcyclopenta-γ-2-benzopyran | 4.8 |
| Benzyl benzoate | 3.2 |
| Acetyl cedrene | 10.0 |
| 2-Ethyl-4-(2,3,3-trimethyl-3-cyclopentene-1-yl)-2-butene-1-ol | 1.0 |
| Vanillin | 0.3 |
| α-Isomethylionone | 12.0 |
| α-Ionone | 1.0 |
| β-Ionone | 12.0 |
| Methyl dihydrojasmonate | 8.0 |
| cis-Jasmone | 0.1 |
| 6-(3-Pentenyl)tetrahydro[2H]pyran-2-one | 0.1 |
| Citronellol | 5.0 |
| Nerol | 1.0 |
| β-Phenylethyl alcohol | 10.0 |
| Tricyclodecenyl acetate | 15.0 |
| n-Decanal | 1.0 |
| cis-3-Hexenol | 1.0 |
| cis-3-Hexene-1-yl acetate | 0.5 |
| Apple base (o-t-butylcyclohexyl acetate rich) | 7.0 |
| Citrus base (lemon fragrance) | 7.0 |

TABLE D10

| Perfume mixture B | (% by mass) |
|---|---|
| Acetyl cedrene | 10.0 |
| 6,7-Dihydro-1,1,2,3,3-pentamethyl-4(5H)indanone | 0.5 |
| 2-Ethyl-4-(2,3,3-trimethyl-3-cyclopentene-1-yl)-2-butene-1-ol | 0.5 |
| Vanillin | 0.5 |
| α-Isomethylionone | 20.0 |
| β-Ionone | 15.0 |
| Tricyclodecenyl acetate | 15.0 |
| Allyl hexanoate | 4.0 |
| Allyl heptanoate | 6.0 |
| Ethyl dehydrocyclogeranate | 1.0 |
| Maltol | 0.5 |
| 4-(p-Hydroxyphenyl)-2-butanone | 1.5 |
| Allyl amyl glycolate | 0.5 |
| cis-3-Hexenol | 1.0 |
| Apple base (o-t-butylcyclohexyl acetate rich) | 8.0 |
| Cassis base | 1.5 |
| Strawberry base | 3.0 |
| Dipropylene glycol | 11.5 |

TABLE D11

| Evaluation results of perfume mixtures | | |
|---|---|---|
| | Ex. D277 (Perfume mixture A) | Ex. D278 (Perfume mixture B) |
| Evaluation (1) | 2.8 | 3.0 |
| Evaluation (2) | 2.8 | 3.0 |
| Evaluation (3) | 2.8 | 2.8 |
| Evaluation (4) | 2.8 | 2.4 |
| Evaluation (5) | 2.4 | 2.2 |

The invention claimed is:

1. A hair processing agent comprising water as solvent and at at least one compound represented by the following formula (2):

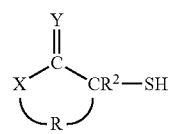

(2)

wherein X is a structure selected from the group consisting of —O—, —S—, —NH— and —NR$^1$—; R$^1$ is an alkyl group of 1 to 6 carbon atoms; Y is an oxygen atom or a sulfur atom; R$^2$ is a hydrogen atom or an alkyl group of 1 to 6 carbons atoms; and R is an alkylene group having a main chain which has 2 to 6 carbon atoms and optionally having one or more mercapto groups;

wherein the pH of the hair processing agent is in the range of 2.5 to 8.7.

2. The hair processing agent according to claim 1, wherein X in the formula (2) is —O—, —NH—, —NCH$_3$— or —S—.

3. The hair processing agent according to claim 1, wherein Y in the formula (2) is an oxygen atom.

4. The hair processing agent according to claim 1, wherein the compound represented by the formula (2) is at least one compound selected from the group consisting of 2-mercapto-4-butyrolactone (another name; 2-mercapto-4-butanolide), 2-mercapto-4-butyrothiolactone, 2-mercapto-4-butyrolactam, N-methyl-2-mercapto-4-butyrolactam, N-ethyl-2-mercapto-4-butyrolactam, N-(2-methoxy)ethyl-2-mercapto-4-butyrolactam, N-(2-ethoxy)ethyl-2-mercapto-4-butyrolactam, 2-mercapto-4-methyl-4-butyrolactone, 2-mercapto-4-ethyl-4-butyrolactone, 2-mercapto-5-valerolactone, 2-mercapto-5-valerolactam, N-methyl-2-mercapto-5-valerolactam, N-ethyl-2-mercapto-5-valerolactam, N-(2-methoxy)ethyl-2-mercapto-5-valerolactam, N-(2-ethoxy)ethyl-2-mercapto-5-valerolactam and 2-mercapto-6-hexanolactam.

5. The hair processing agent according to claim 1, wherein the content of the compound represented by the formula (2) is 0.2 to 30% by mass as a content of reducing substance in terms of thioglycolic acid.

6. A hair processing agent comprising:
(i) at least one compound represented by the following formula (2):

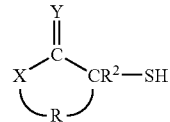

(2)

wherein X is a structure selected from the group consisting of —O—, —S—, —NH— and —NR¹—; R¹ is an alkyl group of 1 to 6 carbon atoms, methoxy ethyl group or ethoxy ethyl group; R² is a hydrogen atom or an alkyl group of 1 to 6 carbon atoms; Y is an oxygen atom or a sulfur atom; and R is a divalent organic residue optionally having a mercapto group, wherein the divalent organic residue is an alkylene group having a main chain which has 2 to 6 carbon atoms;

(ii) at least one compound selected from the group consisting of thioglycolic acid, thiolactic acid, cysteine, cysteamine, dithioglycol, sulfurous acid, salts thereof, ester derivatives thereof and amide derivatives thereof; and (iii) water as solvent, wherein in pH of the hair processing agent is in the range of 2.5 to 8.7.

7. The hair processing agent according to claim 6, wherein the content of the compound (ii) is 0.01 to 50% by mol relative to the compounds (i) and (ii) combined ((ii)/i+ii)).

8. The hair processing agent according to claim 6, wherein the compound (ii) is cysteamine, a salt thereof, or an ester derivative thereof.

9. The hair processing agent according to claim 6, wherein the total content of the compounds (i) and (ii) is 0.2 to 30% by mass as a content of reducing substance in terms of thioglycolic acid.

10. A hair processing agent comprising a compound represented by the following formula (2), a surfactant and water, said hair processing agent being emulsified;

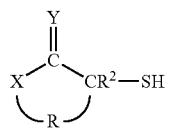

(2)

wherein X is a structure selected from the group consisting of —O—, —S—, —NH— and —NR¹—; R¹ is an alkyl group of 1 to 6 carbon atoms, methoxy ethyl group or ethoxy ethyl group; R² is a hydrogen atom or an alkyl group of 1 to 6 carbon atoms; Y is an oxygen atom or a sulfur atom; and R is a divalent organic residue optionally having a mercapto group, wherein the divalent organic residue is an alkylene group having a main chain which has 2 to 6 carbon atoms, wherein the pH of the hair processing agent is in the range of 2.5 to 8.7.

11. The hair processing agent according to claim 10, wherein the surfactant is at least one type selected from the group consisting of nonionic surfactant, cationic surfactant, anionic surfactant, amphoteric surfactant, polymeric surfactant and biosurfactant.

12. The hair processing agent according to claim 11, wherein the nonionic surfactant is at least one compound selected from the group consisting of polyoxyethylene alkyl ethers, polyoxyethylene alkenyl ethers and polyoxyethylene alkylphenyl ethers containing 10 to 100 moles of polyoxyethylene added.

13. The hair processing agent according to claim 11, wherein the nonionic surfactant is a silicone nonionic surfactant.

14. The hair processing agent according to claim 11, wherein the biosurfactant has a lipopeptide structure.

15. The hair processing agent according to claim 10, wherein the content of the compound represented by the formula (2) is 0.2 to 30% by mass as a content of reducing substance in thioglycolic acid.

16. The hair processing agent according to claim 10, wherein the surfactant is contained in an amount of 0.1 to 20% by mass.

17. A hair processing agent comprising:

(i) at least one compound represented by the following formula (2):

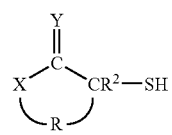

(2)

wherein X is a structure selected from the group consisting of —O—, —S—, —NH— and —NR¹—; R¹ is an alkyl group of 1 to 6 carbon atoms, methoxy ethyl group or ethoxy ethyl group; R² is a hydrogen atom or an alkyl group of 1 to 6 carbon atoms; Y is an oxygen atom or a sulfur atom; and R is a divalent organic residue optionally having a mercapto group, wherein the divalent organic residue is an alkylene group having a main chain which has 2 to 6 carbon atoms;

(ii) at least one perfume selected from the group consisting of (A) hydrocarbons, (B) alcohols, (C) phenols, (D) aldehydes and/or acetals, (E) ketones and/or ketals, (F) ethers, (G) synthetic musks, (H) acids, (I) lactones, (J) esters, (K) nitrogen-containing and/or sulfur-containing and/or halogen-containing compounds, and (L) natural perfumes; and (iii) water as solvent;

wherein the pH of the hair processing agent is in the range of 2.5 to 8.7.

18. The hair processing agent according to claim 17, wherein the perfume (ii) is at least one perfume selected from the group consisting of acetyl diisoamylene, anise alcohol, undecalactone, ethyl maltol, orange oil, camphor, geraniol, geranyl nitrile, dimethyl octanol, cyclopentadecanolide, citral, citronellal, dimethyl octenol, methyl dihydrojasmonate, dihydromyrcenol, cinnamic alcohol, spearmint oil, damascone, tansy oil, Triplal, trimethyl undecadienal, γ-decalactone, trimethyl hexenal, nerol, nerolidol, γ-nonalactone, basil oil, pinene, phenylethyl alcohol, phenyl propanal, fenchyl alcohol, hexenal, cis-3-hexenol, peppermint oil, bergamot oil, benzyl formate, benzaldehyde, borneol, methyl ionone, methyl cinnamic aldehyde, methoxy citronellal, menthanol, menthol, menthone, lime oil, raspberry ketone, linalool, linalool oxide, limonene, lemon oil, rosephenone, butylcyclohexyl acetate, isobornyl acetate, dimethyl phenyl ethyl carbinyl acetate, dimethyl benzyl carbinyl acetate, 4-(1-ethoxyvinyl)-3,3,5,5-tetramethylcyclohexanone, cis-p-menthane-7-ol, α,3,3-trimethylcyclohexanemethyl formate, ethyl 2,2,6-trimethylcyclohexanecarboxylate, 2,6,6-trimethyl-1-crotonylcyclohexane, 2-methyl-4-(2,2,3-trimethyl-3-cyclopentene-1-yl)-2-butene-1-ol, 3-methyl-5-(2,2,3-trimethyl-3-cyclopentene-1-yl)-pentane-2-ol and 2-ethyl-4-(2,2,3-trimethyl-3-cyclopentene-1-yl)-2-butene-1-ol.

19. The hair processing agent according to claim 17, wherein the content of the compound represented by the formula (2) is 0.2 to 30% by mass as a content of reducing substance in terms of thioglycolic acid.

* * * * *

UNITED STATES PATENT AND TRADEMARK OFFICE
CERTIFICATE OF CORRECTION

PATENT NO. : 8,961,946 B2
APPLICATION NO. : 11/792828
DATED : February 24, 2015
INVENTOR(S) : Akira Shibuya et al.

It is certified that error appears in the above-identified patent and that said Letters Patent is hereby corrected as shown below:

Title page, item (57), line 13, Abstract, please delete "perfume." and insert therefor --perfume,--.

Specification

In column 3, line 14, please delete "(1D) to (1D)" and insert therefor --(1D) to (11D)--.

In column 24, line 51, please delete "α,α,ß-trimethylphenylethyl alcohol," and insert therefor --α,α,p-trimethylphenylethyl alcohol,--.

In column 27, line 56, please delete "cedrilone" and insert therefor --cedrelone--.

In column 28, line 62, please delete "γ-hexylactone," and insert therefor --γ-hexalactone,--.

In column 28, line 65, please delete "δ-hexylactone," and insert therefor --δ-hexalactone,--.

In column 34, line 58, please delete "tetrahydropyrol," and insert therefor --tetrahydropyrrole,--.

In column 35, line 29, please delete "patuli" and insert therefor --patchouli--.

In column 35, line 52-53, please delete "dihydronyrcenol," and insert therefor --dihydromyrcenol,--.

In column 39, line 53, please delete "1 Hour" and insert therefor --1 hour--.

In column 39, line 67, please delete "mass)" and insert therefor --mass).--.

Signed and Sealed this
Twenty-third Day of February, 2016

Michelle K. Lee
*Director of the United States Patent and Trademark Office*

CERTIFICATE OF CORRECTION (continued)
U.S. Pat. No. 8,961,946 B2

Claims

In column 64, line 12, please delete "at at" and insert therefor --at--.

In column 64, line 27, please delete "carbons atoms;" and insert therefor --carbon atoms;--.

In column 65, line 15, please delete "wherein in" and insert therefor --wherein the--.

In column 66, line 2, please delete "in thioglycolic acid." and insert therefor --in terms of thioglycolic acid.--.